(12) United States Patent
Medoro et al.

(10) Patent No.: US 9,192,943 B2
(45) Date of Patent: Nov. 24, 2015

(54) MICROFLUIDIC DEVICE FOR ISOLATION OF CELLS

(75) Inventors: Gianni Medoro, Casalecchio di Reno (IT); Gerardo Perozziello, Bologna (IT); Alex Calanca, Mirandola (IT); Giuseppina Simone, Formicola (IT); Nicolò Manaresi, Bologna (IT)

(73) Assignee: SILICON BIOSYSTEMS S.P.A., Bologna (IT)

( * ) Notice: Subject to any disclaimer, the term of this patent is extended or adjusted under 35 U.S.C. 154(b) by 318 days.

(21) Appl. No.: 13/257,545

(22) PCT Filed: Mar. 17, 2010

(86) PCT No.: PCT/IB2010/000615
§ 371 (c)(1),
(2), (4) Date: Mar. 27, 2012

(87) PCT Pub. No.: WO2010/106434
PCT Pub. Date: Sep. 23, 2010

(65) Prior Publication Data
US 2012/0184010 A1  Jul. 19, 2012

(30) Foreign Application Priority Data

Mar. 17, 2009 (IT) .............................. BO2009A0152
Mar. 17, 2009 (IT) .............................. BO2009A0153

(51) Int. Cl.
*C12N 13/00* (2006.01)
*C12M 1/42* (2006.01)
(Continued)

(52) U.S. Cl.
CPC ............ *B03C 5/026* (2013.01); *B01L 3/502738* (2013.01); *B01L 3/567* (2013.01);
(Continued)

(58) Field of Classification Search
USPC .......... 422/68.1, 502–507; 435/283.1, 286.5, 435/173.9
See application file for complete search history.

(56) References Cited

U.S. PATENT DOCUMENTS 5,252,493 A  10/1993 Fujiwara et al.
5,279,493 A  1/1994 Halder
(Continued)

FOREIGN PATENT DOCUMENTS

DE  3931851  4/1992
DE  10203636  2/2004
(Continued)

OTHER PUBLICATIONS

Berthier et al., NSTI Nanotech 2005, vol. 1 (2005), www.nsti.org.
(Continued)

*Primary Examiner* — Lyle Alexander
*Assistant Examiner* — Jennifer Wecker
(74) *Attorney, Agent, or Firm* — Marshall, Gerstein & Borun LLP

(57) ABSTRACT

A microfluidic system (1) for the isolation of cells (C1) of at least one given type from a sample; the system (1) comprises a separation unit (3), for transferring at least part of the cells (C1) of the given type from a main chamber (4) to a recovery chamber (5) in a substantially selective way with respect to further cells (C2) of the sample; two valves (9, 10) are set upstream and downstream of the main chamber (4); two valves (11, 12) are set upstream and downstream of the recovery chamber (5); a control assembly (23) is designed to govern the aforementioned valves (9, 10, 11, 12); the system (1) proposed enables isolation of the cells with a high degree of reproducibility and precision.

79 Claims, 27 Drawing Sheets

(51) Int. Cl.
*F16K 99/00* (2006.01)
*B01L 3/00* (2006.01)
*B03C 5/02* (2006.01)
B03C 5/00 (2006.01)
G01N 15/10 (2006.01)
C12M 1/00 (2006.01)

(52) U.S. Cl.
CPC .... *B01L2200/0652* (2013.01); *B01L 2300/087* (2013.01); *B01L 2300/0877* (2013.01); *B01L 2400/0424* (2013.01); *B01L 2400/0622* (2013.01); *B03C 5/005* (2013.01); *B03C 2201/02* (2013.01); *B03C 2201/26* (2013.01); *C12M 47/04* (2013.01); *F16K 99/0001* (2013.01); *F16K 99/0015* (2013.01); *G01N 2015/1081* (2013.01)

(56) References Cited

U.S. PATENT DOCUMENTS

| | | | |
|---|---|---|---|
| 5,888,370 | A | 3/1999 | Becker et al. |
| 5,945,281 | A | 8/1999 | Prabhu |
| 6,149,789 | A | 11/2000 | Benecke et al. |
| 6,203,683 | B1 | 3/2001 | Austin et al. |
| 6,264,815 | B1 | 7/2001 | Pethig et al. |
| 6,294,063 | B1 | 9/2001 | Becker et al. |
| 6,824,664 | B1 | 11/2004 | Austin et al. |
| 6,830,729 | B1 | 12/2004 | Holl et al. |
| 6,875,329 | B2 | 4/2005 | Washizu et al. |
| 6,888,721 | B1 | 5/2005 | Moghaddam et al. |
| 6,911,132 | B2 | 6/2005 | Pamula et al. |
| 6,977,033 | B2 | 12/2005 | Becker et al. |
| 7,147,763 | B2 | 12/2006 | Elrod et al. |
| 7,250,933 | B2 | 7/2007 | De Boer et al. |
| 7,307,328 | B2 | 12/2007 | Meyer et al. |
| 7,488,406 | B2 | 2/2009 | Hughes et al. |
| 7,641,779 | B2 | 1/2010 | Becker et al. |
| 8,216,513 | B2 | 7/2012 | Becker et al. |
| 8,349,160 | B2 | 1/2013 | Medoro et al. |
| 8,388,823 | B2 | 3/2013 | Manaresi et al. |
| 2002/0031838 | A1 | 3/2002 | Meinhart et al. |
| 2002/0036139 | A1 | 3/2002 | Becker et al. |
| 2002/0070114 | A1 | 6/2002 | Miles |
| 2002/0125138 | A1 | 9/2002 | Medoro |
| 2002/0132316 | A1 | 9/2002 | Wang et al. |
| 2003/0044832 | A1 | 3/2003 | Blankenstein |
| 2003/0047456 | A1 | 3/2003 | Medoro |
| 2003/0073110 | A1 | 4/2003 | Aritomi et al. |
| 2004/0011652 | A1 | 1/2004 | Bressler |
| 2004/0055891 | A1 | 3/2004 | Pamula et al. |
| 2004/0058450 | A1 | 3/2004 | Pamula et al. |
| 2004/0063196 | A1 | 4/2004 | Muller et al. |
| 2004/0159546 | A1 | 8/2004 | Zhang et al. |
| 2004/0191789 | A1 | 9/2004 | Manaresi et al. |
| 2004/0209354 | A1* | 10/2004 | Mathies et al. ............. 435/287.2 |
| 2004/0229210 | A1 | 11/2004 | Sabry et al. |
| 2005/0014146 | A1 | 1/2005 | Manaresi et al. |
| 2005/0214736 | A1 | 9/2005 | Childers et al. |
| 2006/0051775 | A1 | 3/2006 | Bianchi |
| 2006/0086309 | A1 | 4/2006 | Manger et al. |
| 2006/0139638 | A1 | 6/2006 | Muller et al. |
| 2006/0177815 | A1* | 8/2006 | Soh et al. ..................... 435/4 |
| 2006/0223178 | A1 | 10/2006 | Barber et al. |
| 2006/0228749 | A1 | 10/2006 | Wang et al. |
| 2006/0290745 | A1* | 12/2006 | Feng et al. ..................... 347/65 |
| 2007/0026413 | A1 | 2/2007 | Toner et al. |
| 2007/0026415 | A1 | 2/2007 | Fuchs et al. |
| 2007/0051412 | A1* | 3/2007 | Heath et al. ............. 137/561 R |
| 2007/0059683 | A1 | 3/2007 | Barber et al. |
| 2007/0172903 | A1 | 7/2007 | Toner et al. |
| 2007/0250301 | A1 | 10/2007 | Vaisberg et al. |
| 2008/0057572 | A1* | 3/2008 | Petersen et al. ............. 435/306.1 |
| 2008/0058991 | A1* | 3/2008 | Lee et al. ..................... 700/266 |
| 2008/0246489 | A1 | 10/2008 | Coster et al. |
| 2008/0264068 | A1 | 10/2008 | Nakasuka et al. |
| 2009/0205963 | A1 | 8/2009 | Medoro et al. |
| 2009/0218223 | A1 | 9/2009 | Manaresi et al. |
| 2010/0035292 | A1* | 2/2010 | Levhenko et al. ............. 435/29 |
| 2010/0248285 | A1 | 9/2010 | Manaresi |
| 2010/0331205 | A1 | 12/2010 | Medoro |
| 2011/0003380 | A1* | 1/2011 | Miltenyi et al. ............. 435/325 |
| 2011/0193006 | A1 | 8/2011 | Simone et al. |
| 2012/0071335 | A1 | 3/2012 | Manaresi et al. |
| 2012/0091001 | A1 | 4/2012 | Manaresi et al. |
| 2013/0118903 | A1 | 5/2013 | Becker et al. |

FOREIGN PATENT DOCUMENTS

| | | |
|---|---|---|
| DE | 19500660 | 12/2007 |
| EP | 1179585 A2 | 2/2002 |
| EP | 1304388 A2 | 4/2003 |
| EP | 1145766 | 8/2007 |
| JP | 58211272 | 12/1983 |
| JP | 2002503334 A | 1/2002 |
| JP | 2002311461 A | 10/2002 |
| JP | 2002536167 A | 10/2002 |
| JP | 2003121886 A | 4/2003 |
| JP | 2003202604 A | 7/2003 |
| JP | 2004000935 A | 1/2004 |
| JP | 2005501296 A | 1/2005 |
| JP | 2005507997 A | 3/2005 |
| JP | 2006504974 A | 2/2006 |
| JP | 2006512092 A | 4/2006 |
| JP | 2006517024 A | 7/2006 |
| JP | 2007017163 | 1/2007 |
| JP | 2008533487 A | 8/2008 |
| WO | WO-91/07660 | 5/1991 |
| WO | WO-91/08284 | 6/1991 |
| WO | WO-98/04355 | 2/1998 |
| WO | WO-99/17883 | 4/1999 |
| WO | WO-00/28313 | 5/2000 |
| WO | WO-00/47322 A2 | 8/2000 |
| WO | WO-00/69565 A1 | 11/2000 |
| WO | WO-02/12896 | 2/2002 |
| WO | WO-03/014739 | 2/2003 |
| WO | WO-03/035895 A2 | 5/2003 |
| WO | WO-03/045556 | 4/2004 |
| WO | WO-2004/030820 A2 | 4/2004 |
| WO | WO-2004/071668 | 8/2004 |
| WO | WO-2005060432 A2 | 7/2005 |
| WO | WO-2005/098395 | 10/2005 |
| WO | WO-2006/003214 | 1/2006 |
| WO | WO-2006008602 A2 | 1/2006 |
| WO | WO-2006/018849 | 2/2006 |
| WO | WO-2007/010367 A2 | 1/2007 |
| WO | WO-2007/049103 | 5/2007 |
| WO | WO-2007/049120 A2 | 5/2007 |
| WO | WO-2007/110739 | 10/2007 |
| WO | WO-2007/116312 | 10/2007 |
| WO | WO-2007/147018 | 12/2007 |
| WO | WO-2007147076 | 12/2007 |
| WO | WO-2008/112274 | 9/2008 |
| WO | WO-2008/131035 | 10/2008 |
| WO | WO-2009/022222 A2 | 2/2009 |

OTHER PUBLICATIONS

Cheung et al., Impedance spectroscopy flow cytometry: on-chip label-free cell differentiation, Cytometry Part A, 65A(2):124-32 (2005).

Fiedler et al., Electrocasting formation and structuring of suspended microbodies using A.C. generated field cages, Microsystem Technologies, Berlin, Germany, pp. 1-7 (Dec. 1, 1995).

Final office action, U.S. Appl. No. 12/091,367, mail date Nov. 1, 2011.

Fuhr et al., Positioning and manipulation of cells and microparticles using miniturized electric field traps and travelling waves, Sensors and Materials, 7(2):131-46 (1995).

Gascoyne et al., Dielectrophoresis-based programmable fluidic processors, Lab Chip, 4:299-304 (2004).

Gascoyne et al., Particle separation by dielectrophoresis, Electrophoresis, 23(13): 1973-83 (2002).

(56) References Cited

OTHER PUBLICATIONS

Green et al., Ac Electrokinetics: a survey of sub-micrometre particle dynamics, J. Phys. D: Appl. Phys., 33:632-41 (Dec. 10, 1999).
Hughes, Strategies for dielectrophoretic separation in laboratory-on-a-chip systems, Electrophoresis, 23(16): 2569-82 (2002).
International Preliminary Report on Patentability for corresponding International application No. PCT/EP2005/053235, dated Jan. 9, 2007.
International Preliminary Report on Patentability for PCT/IB2006/000636, dated Apr. 29, 2008.
International Preliminary Report on Patentability for PCT/IB2006/001984, dated Dec. 3, 2007.
International Preliminary Report on Patentability for PCT/IB2006/002965, dated Apr. 29, 2008.
International Preliminary Report on Patentability for PCT/IB2007/000751, dated Sep. 30, 2008.
International Search Report and Written Opinion for corresponding International Application No. PCT/EP2005/053235, mailing date May 2, 2006.
International Search Report and Written Opinion for PCT/IB2006/000636, dated Sep. 8, 2006.
International Search Report and Written Opinion for PCT/IB2006/001984, dated Feb. 27, 2007.
International Search Report and Written Opinion for PCT/IB2006/002965, dated Jun. 15, 2007.
International Search Report and Written Opinion for PCT/IB2007/000751, dated Nov. 16, 2007.
Jones, An electromechanical interpretation of electrowetting, J. Micromech. Microeng., 15(6):1184-7 (2005).
Milner et al., Dielectrophoretic classification of bacteria using differential impedance measurements, Electronics Letters, 34(1):66-8 (1998).
Nieuwenhuis et al., Near-field optical sensors for particle shape measurements, Sensors Journal IEEE, 3(5):646-51 (2003).
Nonfinal office action, U.S. Appl. No. 12/091,367, mail date Mar. 25, 2011.
Nonfinal office action, U.S. Appl. No. 12/294,860, mail date Jan. 27, 2012.
Ohta et al., Tech. Dig. of the Solid State Sensor, Actuator and Microsystems, Workshop, pp. 216-219 (2004).
Petersson et al., Carrier medium exchange through ultrasonic particle switching in microfluidic channels, Anal. Chem., 77:1216-21 (2005).
Schnelle et al., Three-dimensional electric field traps for manipulation of cells—calculation and experimental verfication, Biochem. Biophys. Acta, 1157(2):127-40 (1993).
Suehiro, The dielectrophoretic movement and positioning of a biological cell using a three-dimensional grid electrode system, J. Phys. D: Appl. Phys., 31:3298-305 (1998).
Altomare et al., Levitation and movement of human tumor cells using a printed circuit board device based on software-controlled dielectrophoresis, Biotechnol. Bioeng., 82(4):474-9 (2003).
Manaresi et al., A CMOS chip for individual cell manipulation and detection, IEEE Journal of Solid-State Circuits, 38 (12):2297-305 (2003).
Medoro et al., A lab-on-a-chip for cell detection and manipulation, IEEE Sensors Journal, 3(3):317-25 (2003).
Medoro et al., A lab-on-a-chip for cell separation based on the moving-cages approach, Proceedings of the 16th Conference on Solid State Transducers, pp. 500-501 (Sep. 15, 2002).

Medoro et al., Dielectrophoretic cage-speed separation of bio-particles, Sensors, Proceedings of the IEEE Vienna, Austria, Oct. 24-27, 2004, pp. 76-79.
O'Hara et al., Ratcheting electrophoresis microchip (REM) for programmable transport and separation of macromolecules, Proceedings of the International Mechanical Engineering Congress and Exposition, 3:619-28 (2001).
Pethig et al., Enhancing traveling-wave dielectrophoresis with signal superposition, IEEE Eng. Med. Biol. Mag., 22(6):43-50 (2003).
Rousselet et al., Directional motion of brownian particles induced by a periodic asymmetric potential, Nature, 370(6489):446-8 (1994).
Bonci et al., The *miR-15a-miR-16-1* cluster controls prostate cancer by targeting multiple oncogenic activities, Nat. Med., 14:1271-7 (2008).
Final office action, U.S. Appl. No. 11/724,697, mail date Jan. 27, 2012.
Fuchs et al., Electronic sorting and recovery of single live cells from microlitre sized samples, Lab Chip, 6:121-6 (2006).
International Preliminary Report on Patentability for corresponding International Application No. PCT/IB2009/007316, Jan. 21, 2011.
ISR in PCT/IB2008/002873, dated Aug. 3, 2009.
Klein et al., Comparative genomic hybridization, loss of heterozygosity, and DNA sequence analysis of single cells, Proc. Natl. Acad. Sci. USA, 96(8):4494-9 (1999).
Nagrath et al., Isolation of rare circulating tumour cells in cancer patients by microchip technology, Nature, 450(7173):1235-9 (2007).
Nonfinal office action, U.S. Appl. No. 11/724,697, notification date Jun. 7, 2011.
Nonfinal office action, U.S. Appl. No. 11/724,697, notification date Sep. 23, 2010.
Nonfinal office action, U.S. Appl. No. 11/996,068, mail date Jan. 4, 2013.
Nonfinal office action, U.S. Appl. No. 12/091,438, mail date Jul. 25, 2013.
Nonfinal office action, U.S. Appl. No. 12/740,170, mail date Jun. 5, 2013.
Reichle et al., Combined laser tweezers and dielectric field cage for the analysis of receptor-ligand interactions on single cells, Electrophoresis, 22(2):272-82 (2001).
Romani et al., Capacitive sensor array for localization of bioparticles in CMOS lab-on-a-chip, Proc. Int. Solid State Circuit Conference, 1:224-5 (2004).
Stoecklein et al., Direct genetic analysis of single disseminated cancer cells for prediction of outcome and therapy selection in esophageal cancer, Cancer Cell, 13:441-53 (2008).
Zieglschmid et al., Detection of disseminated tumor cells in peripheral blood, Crit. Rev. Clin. Lab. Sci., 42(2):155-96 (2005).
English translation of Office Action, Japanese patent application No. 2012-167396 (Aug. 2, 2013).
International Search Report and Written Opinion for corresponding International Application No. PCT/IB2010/000615, mailing date Aug. 26, 2010.
International Preliminary Report on Patentability for corresponding International Application No. PCT/IB2010/000615, dated Sep. 20, 2011.
de Bono et al., Circulating tumor cells predict survival benefit from treatment in metastatic castration-resistant prostate cancer, Clin. Cancer Res., 14(19):6302-9 (2008).
Office Action, corresponding Japanese patent application No. 2012-500332, dated Aug. 5, 2014.

* cited by examiner

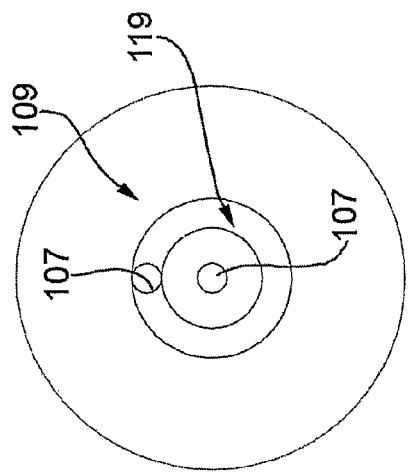
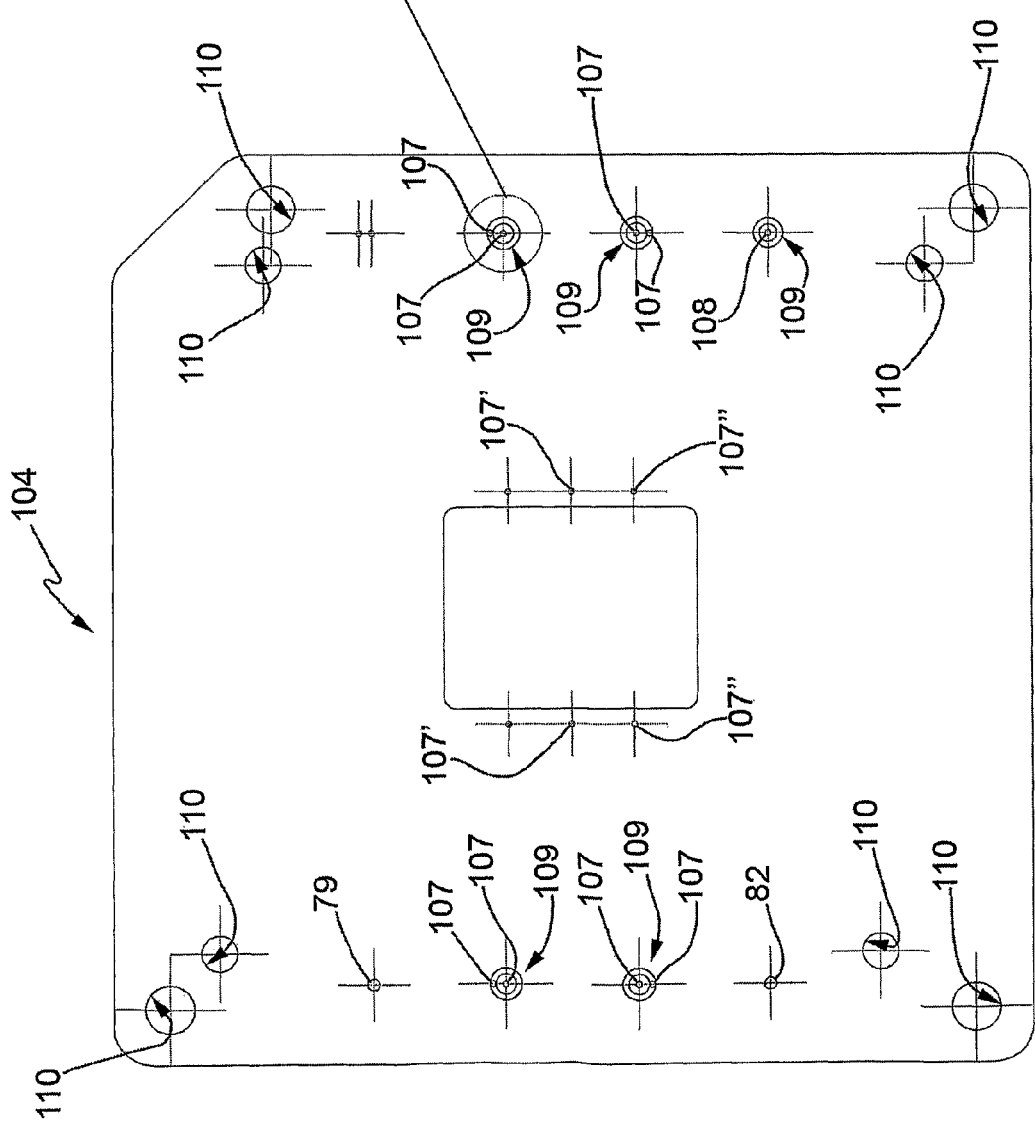
FIG.33
FIG.32

MICROFLUIDIC DEVICE FOR ISOLATION OF CELLS

CROSS-REFERENCE TO RELATED APPLICATIONS

This is the U.S. national phase application of International Application No. PCT/IB2010/000615, filed Mar. 17, 2010, which claims the benefit of Italian Patent Application Nos. BO2009A 000152, filed Mar. 17, 2009, and BO2009A 000153, filed Mar. 17, 2009.

TECHNICAL FIELD

The present invention relates to a microfluidic system, an apparatus for isolation of particles, a microfluidic device, and a method for isolation of particles.

BACKGROUND ART

Known to the art is a device for isolation of particles of a given type, which comprises a main chamber, in which an operator, using a pipette, introduces a sample through a hole of the main chamber, and a recovery chamber, from which the operator, once again using a pipette, draws the particles of the given type through a hole of the recovery chamber.

The documents Nos. US2003/0073110 and EP1179585 disclose complex devices for the manipulation of samples, which comprise a plurality of valves completely contained in the devices themselves.

The document No. US2004/0209354 discloses only some aspects of a system for the manipulation of particles, details of the structure of the device and of its operation are not specified.

Known devices have various problems of precision during the steps of separation, introduction, and recovery. Furthermore, the results are not always reproducible, at times contamination of the sample occurs during the various steps, and the intervention of operators with particular manual skills is frequently necessary.

DISCLOSURE OF INVENTION

The aim of the present invention is to provide a microfluidic system, an apparatus for isolation of particles, a microfluidic device, and a method for isolation of particles, which will enable the drawbacks of the current art to be overcome, at least partially, and will at the same time be easy and economically advantageous to produce.

According to the present invention, a microfluidic system is provided in accordance with what is specified in the ensuing independent claims and, preferably, in any one of the claims that depend directly or indirectly upon the independent claims.

Unless otherwise explicitly specified, in the present text the following terms have the meaning indicated hereinafter.

By "equivalent diameter" of a cross section is understood the diameter of a circle having the same area as the cross section.

By "cross section" of a channel or of a duct is understood the section substantially perpendicular to the longitudinal extension of the channel (or duct) i.e., to the direction of advance of the fluid in the channel (or duct).

By "equivalent diameter" of a hole is understood the diameter of a circle having the same area as the cross section of smallest dimensions of the hole itself.

By "microfluidic system (or device)" is understood a system (or device) comprising at least one microfluidic channel (or duct).

By "microfluidic channel (or duct)" is understood a channel (or duct) having a cross section with equivalent diameter of less than 1 mm.

The dimensions of the channels or ducts can be measured in a standard way using profilometers.

In the present text, by "particle" is understood a corpuscle having its largest dimension of less than 500 μm (advantageously less than 150 μm). Non-limiting examples of particles are: cells, cellular detritus (in particular, cell fragments), cellular aggregates (such as, for example, small clusters of cells deriving from stem cells, such as neurospheres or mammospheres), bacteria, lipospheres, (polystyrene and/or magnetic) microspheres, and complex nanospheres (for example, nanospheres of up to 100 nm) formed by microspheres linked to cells. Advantageously, the particles are cells.

According to some embodiments, the particles (advantageously cells and/or cellular detritus) have a largest dimension of less than 60 μm.

The dimensions of the particles can be measured in a standard way using microscopes with graduated scale or normal microscopes used with graduated-scale slides (on which the particles are deposited).

In the present text, by "dimensions" of a particle is understood the length, the width, and the thickness of the particle.

The term "substantially selective" is used for identifying a displacement (or other analogous terms indicating a movement and/or a separation) of particles, in which the particles that are displaced and/or separated are particles for the vast majority of one or more given types. Advantageously, a substantially selective displacement (or other analogous terms indicating a movement and/or a separation) envisages displacement of particles with at least 90% (advantageously 95%) of particles of the given type or types (percentage given by the number of particles of the given type or types with respect to the total number of particles).

BRIEF DESCRIPTION OF THE DRAWINGS

The invention is described hereinafter with reference to the annexed drawings, which illustrate some non-limiting examples of embodiments thereof and in which:

FIG. 32 is a plan view from beneath of a variant of the component of FIG. 6 and, in particular, a component of the device of FIG. 31; and FIG. 33 illustrates at an enlarged scale a detail of FIG. 32.

BEST MODE FOR CARRYING OUT THE INVENTION

Microfluidic System

Figure 20:
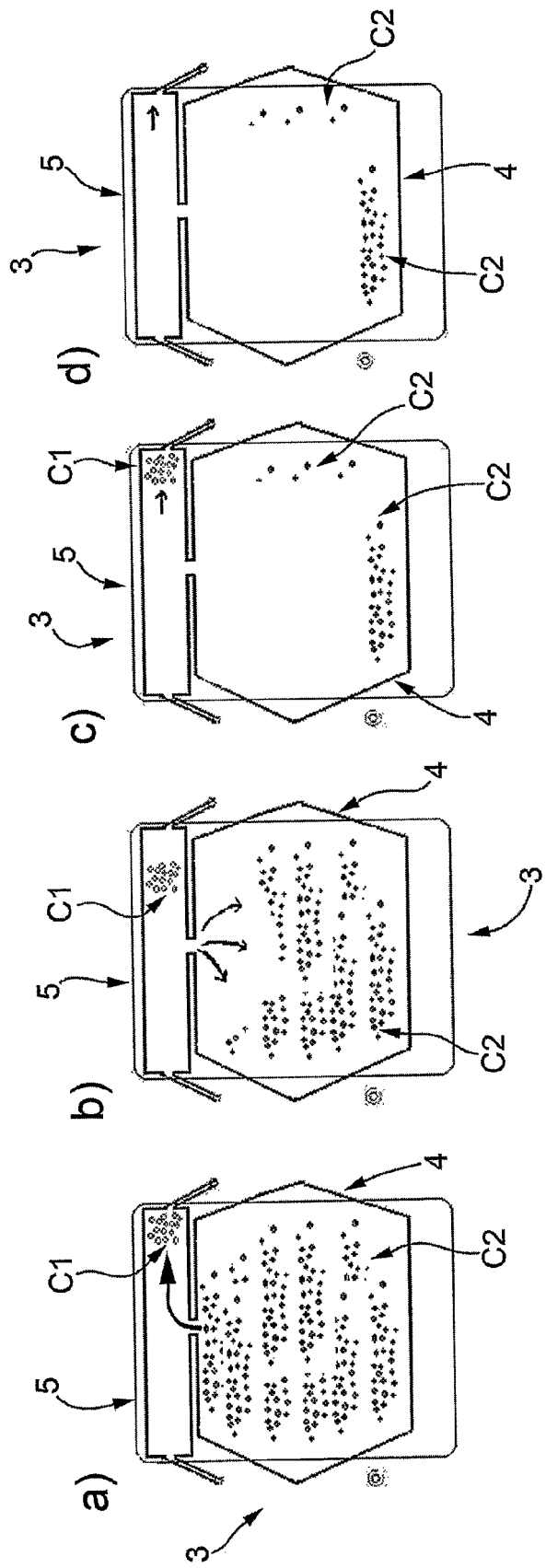

Provided according to a first aspect of the present invention is a microfluidic system 1 for the substantial isolation of particles C1 (schematically illustrated in FIG. 20) of at least one given type from a sample. The system 1 (FIG. 1) comprises: an inlet 2, through which, in use, the sample is introduced into the system 1; a separation unit 3, which is designed to separate in a substantially selective way at least a part of the particles C1 of the given type from further particles C2 of the sample (schematically illustrated in FIG. 20); and an outlet 8, which is connected to the separation unit 3 and, in particular, through which, in use, at least part of the particles C1 of the given type separated in a substantially selective way exit from the system 1. The separation unit 3 is connected to the inlet 2.

According to some embodiments, the system 1 comprises: a valve 9, set between the inlet 2 and the separation unit 3 (in particular, between the inlet 2 and the main chamber 4); and a valve 12, set between the outlet 8 and the separation unit 3. In particular, the system 1 comprises a valve set between the separation unit 3 and each opening of the system 1 towards the outside.

According to some embodiments, the separation unit 3 comprises a main chamber 4 and a recovery chamber 5 and is designed to transfer at least part of the particles C1 of the given type from the main chamber 4 to the recovery chamber 5 in a substantially selective way with respect to the further particles C2 of the sample.

The separation unit 3 further comprises a channel 5, which connects (i.e., enables passage of fluid between) the chambers 4 and 5 and has dimensions (in particular, width and length) much smaller than those of both of the chambers 4 and 5 themselves.

The system 1 is equipped with: an outlet 7, connected to the main chamber 4 to enable the sample to enter freely within the main chamber 4, thus functioning as breather; and the outlet 8, which is connected to the recovery chamber 5 and through which, in use, at least part of the particles C1 of the given type collected in the recovery chamber 5 exit from the system 1.

The system 1 further comprises: the valve 9, set upstream of the main chamber 4; a valve 10, set between the main chamber 4 and the outlet 7; a valve 11, connected to the recovery chamber 5; and the valve 12, set between the recovery chamber 5 and the outlet 8. In particular, the valve 11 is set between the recovery chamber 5 and a source of a carrier liquid.

More precisely, the recovery chamber 5 is set between the main chamber 4 on one side and the valves 11 and 12 on the other side; the main chamber 4 is set between the recovery chamber 5 on one side and the valves 9 and 10 on the other side.

The valves 9 and 10 are designed to regulate inflow of the sample to the main chamber 4.

The valves 11 and 12 are designed to regulate inflow of a carrier liquid to the recovery chamber 5 and outflow of the carrier liquid together with the particles C1 of the given type from the recovery chamber 5 through the outlet 8.

If, in use, the valves 9 and 12 are closed and the valves 11 and 10 are opened, a flushing of the main chamber 4 is carried out; in other words, the further particles C2 of the sample are discharged (i.e., made to flow away) from the main chamber 4.

According to specific embodiments, the carrier liquid is a buffer solution, in particular phosphate-buffered saline (PBS).

Figure 1:
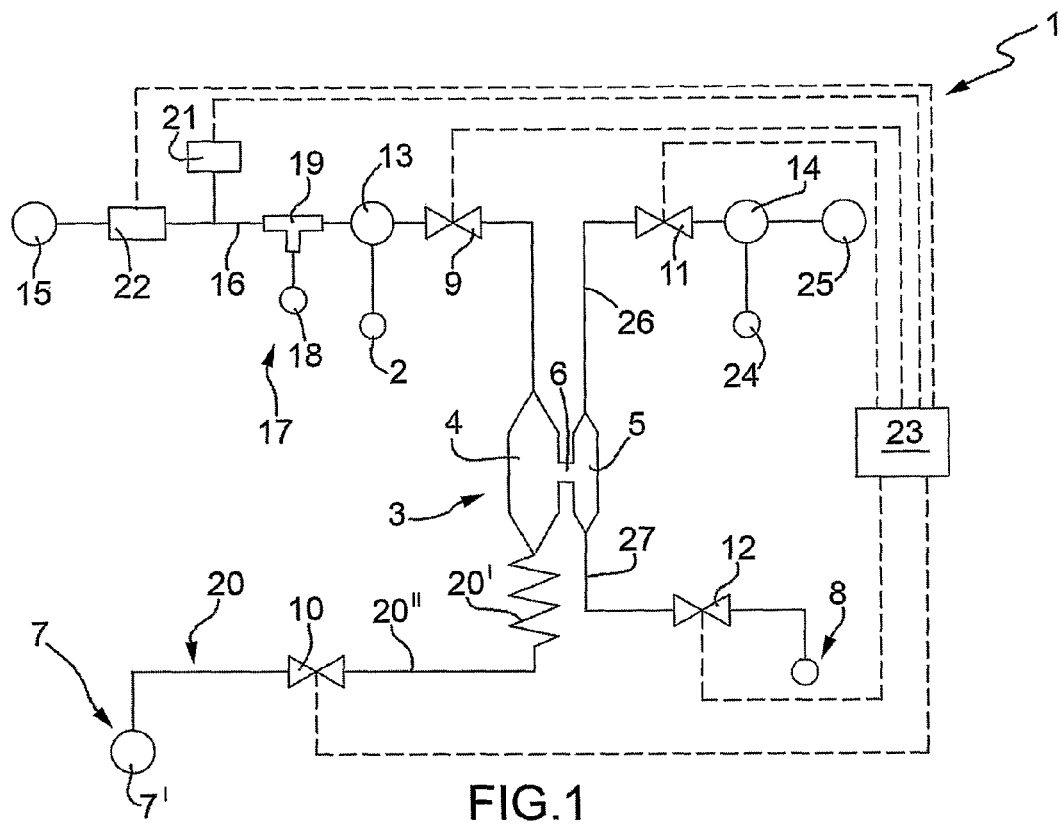
FIG. 1 is a schematic illustration of a system built in accordance with the present invention.

According to the embodiment illustrated in FIG. 1, the system 1 comprises: a reservoir 13, which is set between the inlet 2 and the valve 9 and is designed to collect the sample introduced through the inlet 1 itself; and a reservoir 14 for containing the carrier liquid, which is designed to fill the recovery chamber 5. In other words, the reservoir 14 functions as source of the carrier liquid. The system 1 further comprises a reservoir 7', which is set at the outlet 7 and is designed to collect the fluids coming from the main chamber 4.

The valve 9 is set between the inlet 2 and the main chamber 4, in particular between the reservoir 13 and the main chamber 4, and is designed to connect or isolate the inlet 2 and the main chamber 4 with respect to one another.

Advantageously, the system 1 further comprises a pressure source 15 for imposing a pressure difference between the reservoir 13 and the main chamber 5 in a direction of supply of the given pressure. In particular, the pressure source 15 is designed to impose a pressure from the reservoir 13 towards the main chamber 5 in a direction of supply of the given pressure. According to some embodiments, the reservoir 13 is set between the pressure source 15 and the valve 9.

In particular, the reservoir 13 is set between the pressure source 15 and the main chamber 4.

According to specific embodiments, the system 1 comprises a duct 16, which connects. (i.e., enables passage of fluid between) the pressure source 15 and the main chamber 4 and along which the reservoir 13 and the valve 9 are set. The duct 16 has a cross section of equivalent diameter of less than or equal to 2 mm; advantageously, the duct 16 has a cross section of equivalent diameter greater than or equal to 50 µm. The duct 16 comprises at least one stretch, which has a cross section with equivalent diameter of less than or equal to 0.9 mm.

The system 1 further comprises a vibration device 17, which is designed to cause variation in an oscillating way of the pressure exerted on the sample at least in an area from the inlet 2 to the main chamber 4 and is set between the pressure source 15 and the reservoir 13. In this way, the particles C1 and C2 of the sample present in the reservoir 13 and/or in the duct 16 and/or in the main chamber 4 are made to vibrate; inflow of the particles C1 and C2 of the sample from the reservoir 13 to the main chamber 4 is improved. The particles C1 and C2 have a smaller tendency to cluster or adhere to the walls of the reservoir 13 and/or of the duct 16 and/or of the main chamber 4. The homogeneity of the distribution of the particles C1 and C2 within the main chamber 4 is improved.

Advantageously, the vibration device 17 comprises an oscillating diaphragm 18, connected, in particular by means of a T-joint 19, to the duct 16. According to specific embodiments, the oscillating diaphragm is a micropump (Thinxxs® MDP2205) with inlet and outlet short-circuited.

According to some embodiments (not illustrated in FIG. 1), the inlet 2 is set along the duct 16, between the pressure source 15 (in particular, the joint 19) and the reservoir 13.

According to some embodiments, the system 1 comprises a duct 20, which is set between the main chamber 4 and the outlet 7 and has at least one stretch 20' having a cross section smaller than the cross section of the duct 16. In particular, the cross section of the stretch 20' is smaller by at least 100 μm than the cross section of the duct 16. Advantageously, the stretch 20' is set immediately downstream (i.e., without interposition of further stretches or elements) of the main chamber 4.

The stretch 20' has a width of less than 150 μm, a depth of less than 110 μm, and a length greater than 2 mm. Advantageously, the stretch 20' has a width greater than 100 μm, a depth greater than 30 μm, and, in particular, a length of less than 6 mm.

According to some embodiments, the duct 20 comprises a stretch 20", which is set between the stretch 20' and the outlet 7 and has a cross section of equivalent, diameter greater than that of the stretch 20' (in particular, substantially equal to that of the duct 16).

In general, according to different embodiments, the system 1 comprises: a sensor for detecting directly or indirectly when the sample starts to enter the duct 20; a blocking device for blocking inflow of the sample towards the main chamber; and a control assembly connected to the sensor and to the blocking device for actuating the blocking device according to what is detected by the sensor (in particular, when the sample starts to enter the duct 20).

According to some specific embodiments, the system 1 comprises: a pressure sensor 21 for detecting pressure variations along the duct 16 and/or at the main chamber 4; and a blocking device 22 for blocking inflow of the sample towards the main chamber 4. The system 1 further comprises a control assembly 23 connected to the pressure sensor 21 and to the blocking device 22 for actuating the blocking device 22 as a function of the variation of pressure detected. In particular, in use, the control assembly 23 actuates the blocking device 22 when the pressure sensor 21 detects a pressure greater than a given threshold pressure.

According to further specific embodiments, the system 1 comprises, in addition or as an alternative to the pressure sensor 21, one or more from among the following elements: an optical sensor, set at the entrance of the stretch 20'; a detector of electrical conductivity, which is set at the entrance of the stretch 20' for detecting variations. of conductivity due to the start of the passage of the sample; a detector of electrical permittivity, which is set at the entrance of the stretch 20' for detecting variations of permittivity due to the start of the passage of the sample; a detector of thermal resistance, which is set at the entrance of the stretch 20' for detecting variations of thermal resistance due to the start of the passage of the sample; and a detector of thermal capacity, which is set at the entrance of the stretch 20' for detecting variations of thermal capacity due to the start of the passage of the sample. In all these cases, the control assembly 23 is connected to the detector/detectors and is designed to actuate the blocking device 20 as a function of the variations detected by the detector/detectors.

According to some embodiments, the optical sensor is an integrated photodiode or else an external video camera (possibly with a system for image enlargement).

With particular reference to FIG. 23, the blocking device 22 comprises a relief valve 22' and is, advantageously, set between the pressure source 15 and the reservoir 13; when the blocking device 22 is operated, the relief valve 22' is opened, and the jet of air coming from the pressure source 15 is released towards the outside, and the pressure along the duct 16 drops. The relief valve 22' is hydraulically connected to the duct 16 by means of a T-joint 22".

In particular, the blocking device 22 is set between the joint 19 and the pressure source 15, specifically upstream of the pressure sensor 21 with respect to the direction of supply of the pressure to the main chamber 4.

From what has been set forth above, it may be inferred that introduction of the sample into the separation unit 3 is improved, so reducing the risk of a significant part of the sample passing beyond the separation unit 3 itself.

According to alternative embodiments, the blocking device 22 is not present, the blocking function being performed by the valve 9, which is connected to the control assembly 23. In other words, the control assembly 23, in use, closes the valve 9 when the pressure sensor 21 detects a pressure higher than the given threshold pressure.

Advantageously, the control assembly 23 is connected to the valves 9, 10, 11, and 12.

The connection between the control assembly and other elements (devices, valve units, etc.) can be provided via traditional electrical connections (conductor cables) or else via electromagnetic waves (for example, by means of radio waves, microwaves, etc.).

According to some embodiments, the system 1 comprises an inlet 24. The reservoir 14 is set between the inlet 24 and the valve 11 and is designed to collect the carrier liquid introduced through the inlet 24.

The valve 11 is set between the inlet 24 and the recovery chamber 5 and is designed to connect or isolate the inlet 24 and the recovery chamber 5 with respect to one another. In particular, the valve 11 is set between the reservoir 14 and the recovery chamber 5 and is designed to connect or isolate the reservoir 14 and the recovery chamber 5 with respect to one another.

According to some embodiments, the system 1 comprises a pressure source 25 for imposing a pressure difference between the reservoir 14 and the recovery chamber 5. In particular, the pressure source 25 imposes a pressure from the reservoir 14 towards the recovery chamber 5.

Advantageously, the reservoir 14 is set between the pressure source 25 and the valve 11. In particular, the system 1 comprises a duct 26, which connects (i.e., enables passage of fluid between) the pressure source 25 and the recovery chamber 5 and along which the reservoir 14 and the valve 13 are set.

According to some embodiments, the inlet 24 is set along the duct 26, in particular between the pressure source 25 and the reservoir 14.

Figure 3:
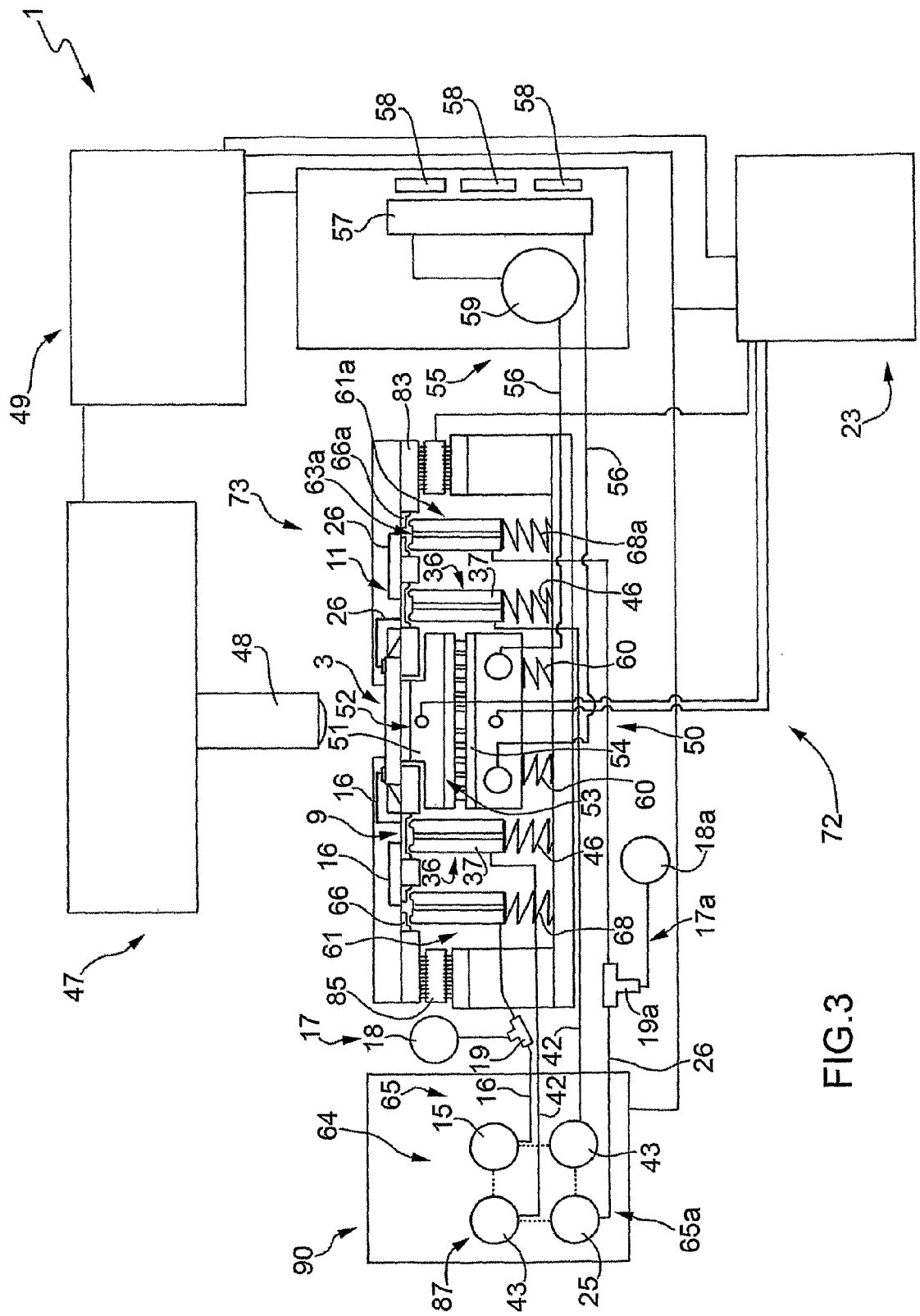
FIG. 3 is a schematic lateral view of the system of FIG. 1.

With particular reference to FIG. 3, the system 1 comprises a vibration device 17a, which is similar to the vibration device 17 and is designed to cause a variation in an oscillating way of the pressure at least in an area of the recovery chamber 5. In this way, the particles C1 of the given type present within the recovery chamber 5 are made to vibrate, and the outflow of the particles C1 of the given type itself from the recovery chamber 5 towards the outlet is improved. The particles C1 have a reduced tendency to cluster or adhere to the walls of the recovery chamber 5 and/or of a duct 27 that connects (i.e., enables passage of fluid between) the recovery chamber 5 to the outlet 8. The valve 12 is set between the recovery chamber 5 and the outlet 8.

Advantageously, the vibration device 17a comprises a diaphragm pump 18a connected, in particular by means of a T-joint 19a, to the duct 26.

According to embodiments (not illustrated), the system for filling of the chamber 5 is similar to that for the chamber 4.

Consequently, in said cases, a blocking device (not illustrated) is set between the pressure source 25 and the reservoir 14; moreover, one or more sensors and/or detectors (not illustrated) analogous to the ones described above with reference to the main chamber 4 are arranged at the entrance of the duct 27 or in other appropriate positions.

According to embodiments (not illustrated), the system 1 comprises a detector (in particular, an optical or impedentiometric or ultrasound detector), which is set at the outlet 8, is connected to the control assembly 23, and is designed to detect a liquid that exits from the outlet 8. The control assembly 23 is designed to regulate the opening of the valve 11 and/or 12 as a function of what is detected by the optical sensor. In particular, in use, when the optical sensor detects at least one drop of carrier liquid (in which at least part of the particles C1 of the given type is present) the control assembly 23 actuates a relief valve, which brings the actuation pressure to zero, thus blocking the flow of the liquid.

In addition or as an alternative, when the optical sensor detects at least one drop of carrier liquid (in which at least part of the particles C1 of the given type is present) the control assembly 23 closes the valve 12 and/or the valve 11.

In this way, it is possible to obtain the particles C1 in a very small volume of liquid. This facilitates the subsequent steps of analysis.

Figure 2:
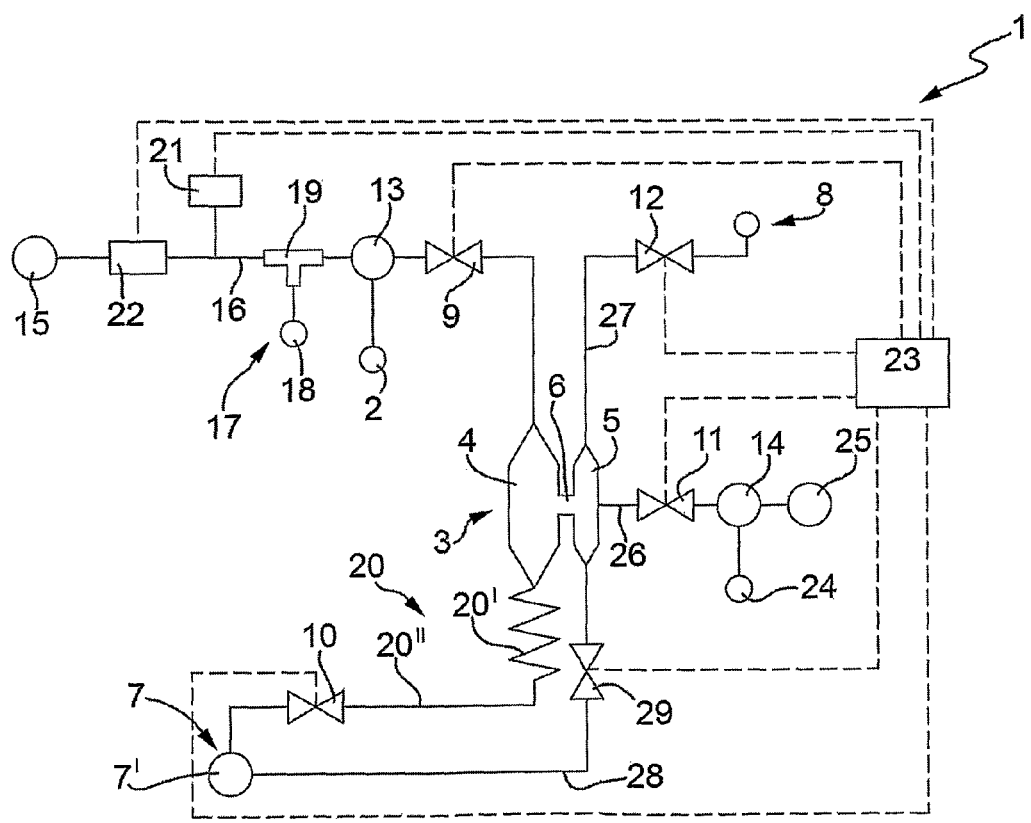
FIG. 2 is a schematic illustration of an alternative embodiment of a system built in accordance with the present invention.

FIG. 2 illustrates an embodiment of the system 1 that differs from the system 1 of FIG. 1 for the position of the duct 26 with respect to the recovery chamber 5 and in that it comprises a duct 28, which connects the recovery chamber 5 to the outlet 7 (or to a further outlet, not illustrated) and along which a valve 29 is set, connected to the control assembly 23. The duct 26 connects up to the recovery chamber 5 between the ducts 27 and 28. In particular, the duct 26 connects up to the recovery chamber 5 substantially in front of the channel 6.

Figure 15:
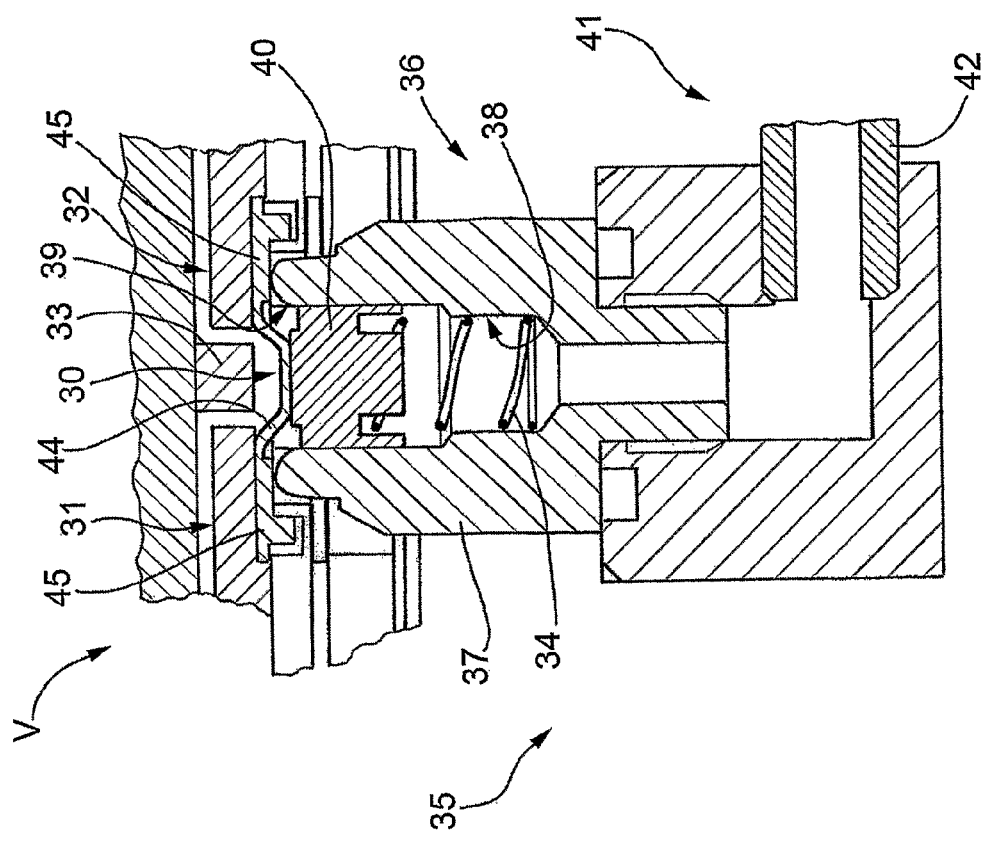
FIGS. 14 and 15 illustrate in partial cross section a detail of the systems of FIGS. 1 to 3 in two different operating positions.
Figure 14:
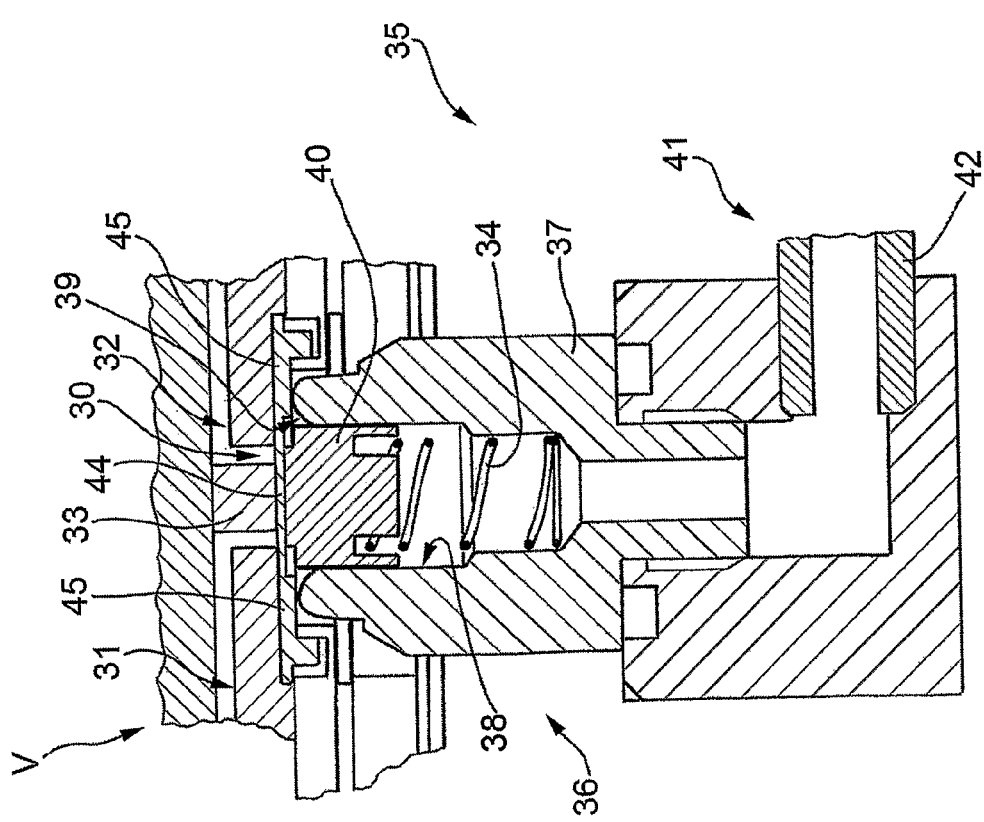
Figure 16:
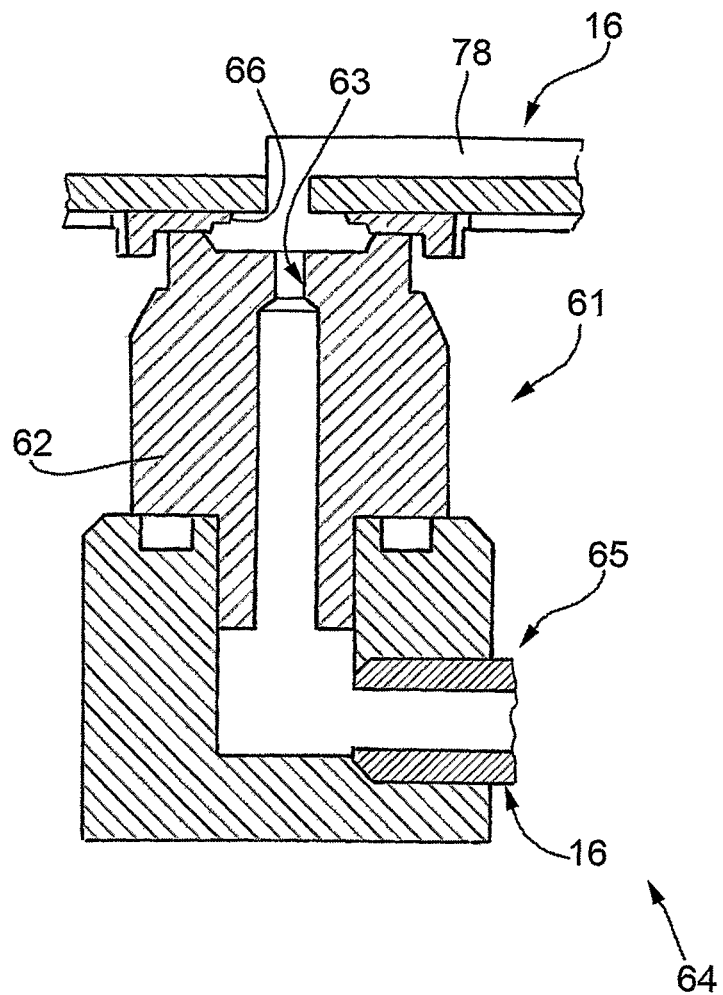
FIG. 16 illustrates in partial cross section a detail of the systems of FIGS. 1 to 3.
Figure 17:
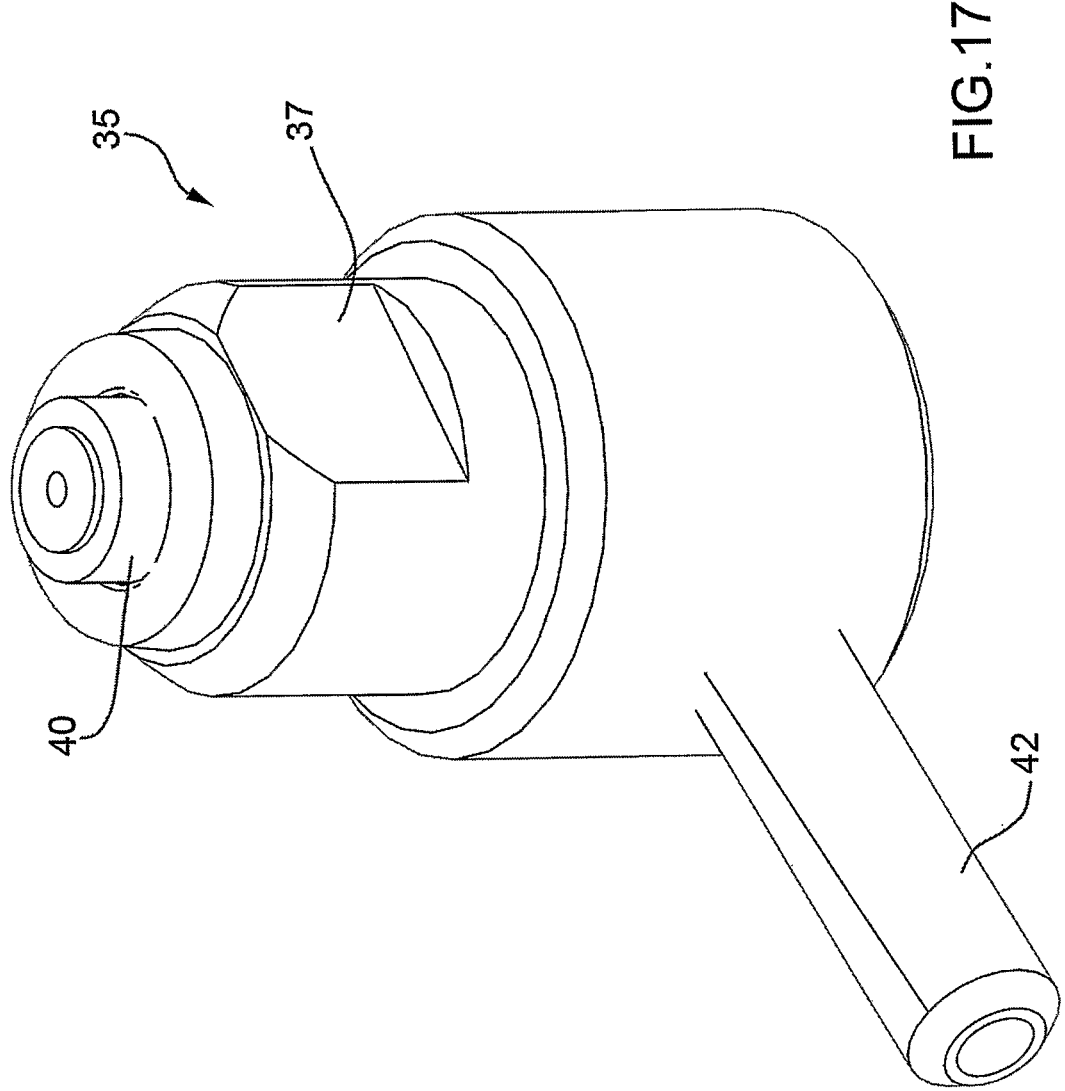
FIG. 17 is a perspective view of a part of the detail illustrated in FIGS. 14 and 15.
Figure 18:
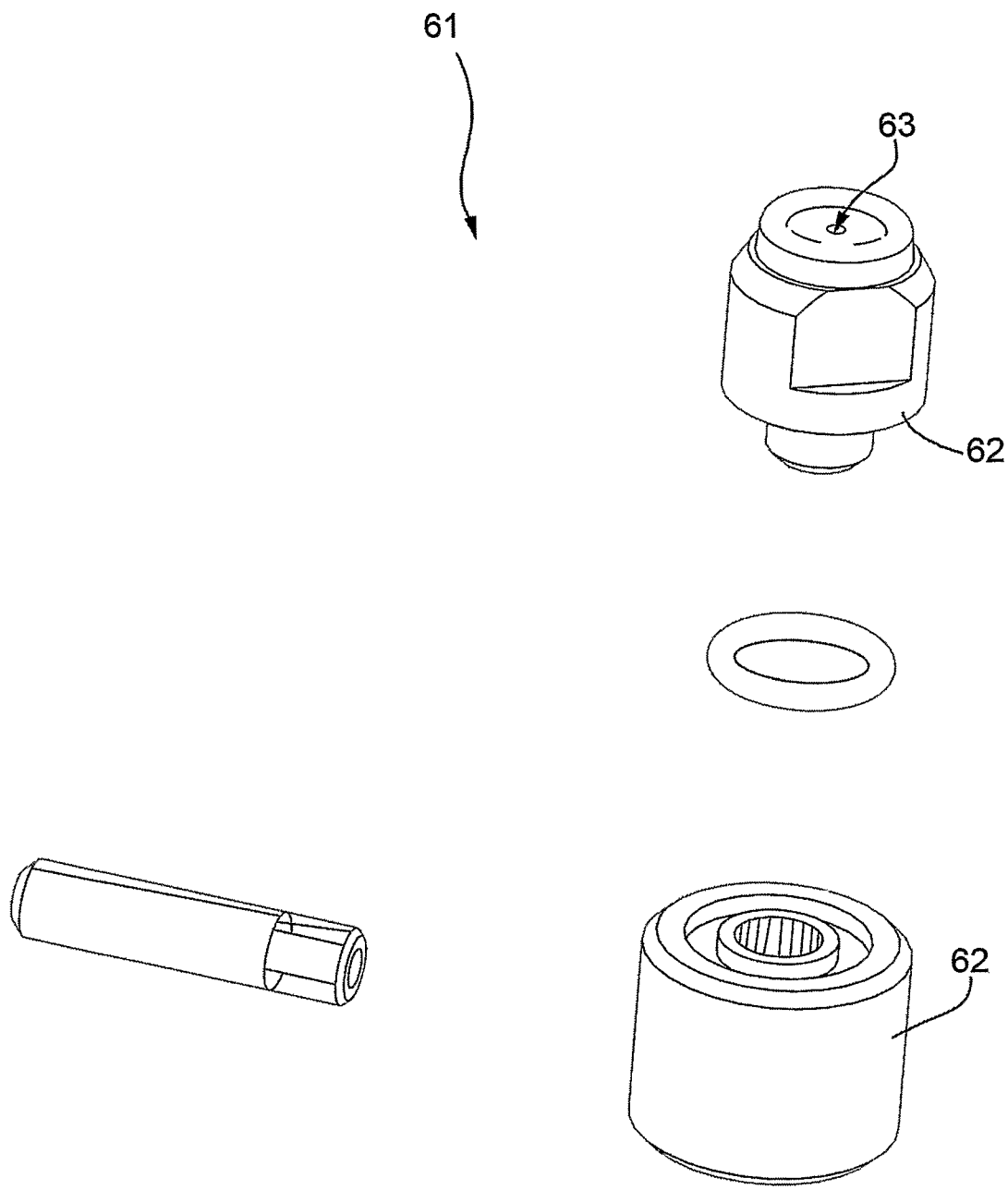
FIG. 18 is an exploded perspective view of the detail of FIG. 17.
Figure 19:
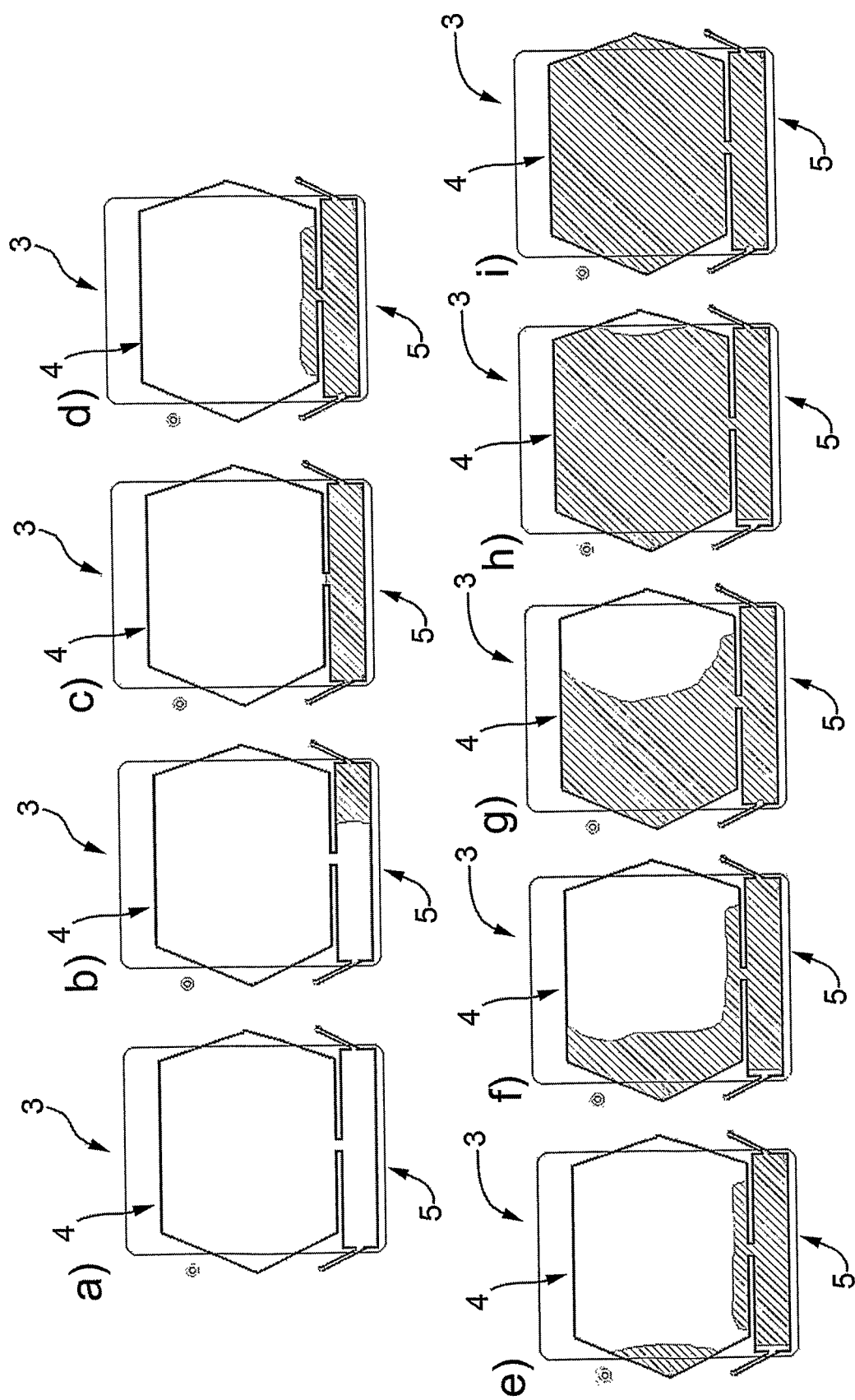
FIGS. 19 and 20 illustrate a detail of the device of FIG. 4 in various operating steps.

With particular reference to FIGS. 14 and 15, according to some embodiments, at least one from among the valves 9, 10, 11 and 12 (in particular, each valve 9, 10, 11 and 12) has a particular structure described below with reference to a particular valve V (in other words, one or more of the valves 9, 10, 11 and 12 has the structure of the valve V described below).

According to one aspect of the present invention, a valve V is provided.

The valve V is equipped with a closing element 30, which comprises (in particular, is made of) a substantially elastic material, and is designed to pass between a blocking position (illustrated in FIG. 14), in which the closing element 30 separates two stretches 31 and 32 of a respective duct, and an opening position (illustrated in FIG. 15), in which the closing element 30 is set in such a way that the passage of fluid between the stretches 31 and 32 is allowed.

The valve V comprises a diaphragm 33, which is set between the two stretches 31 and 32. When the closing element 30 is set in the blocking position, the closing element 30 itself is in contact with the diaphragm 33 so as to separate the stretches 31 and 32. When the closing element 30 is set in the opening position, the closing element 30 itself is set at a distance from the diaphragm 33 so as to enable the passage of fluid between the stretches 31 and 32.

The valve V further comprises a respective mechanical pressure element 34, which pushes the closing element 30 towards the stretches 31 and 32 (in particular, towards the diaphragm 33) so as to keep the closing element 30 itself in the blocking position. Advantageously, the mechanical pressure element 34 comprises (in particular, is) a spring, which is compressed when the closing element 34 passes from the blocking position to the opening position and extends when the closing element 34 passes from the opening position to the blocking position.

The valve V comprises a fluid-dynamic actuator 35, which in turn comprises an actuator nozzle 36 equipped with a hollow element 37, which houses the mechanical pressure element 34. The hollow element 37 has an internal channel 38 and an open end (in particular, provided with an actuator hole 39) set in contact with the closing element 34.

The fluid-dynamic actuator 35 comprises a sealing element 40, which is designed to slide in a fluid-tight way along the internal channel 38 and is set in a position corresponding to the actuator hole 39 in contact with the mechanical pressure element.

The fluid-dynamic actuator 35 further comprises a suction unit 41, which, in turn, comprises a duct 42 that connects the actuator nozzle 36 to a suction source 43 (illustrated in FIG. 3).

In use, when the suction unit 41 is operated, the sealing element 30 is sucked back and pushes the sealing element 40, which slides within the internal channel 38 so as to compress the mechanical pressure element 34. Said negative pressure moves the closing element 30 away from the diaphragm 33 in such a way that the closing element 30 reaches the opening position. When the suction unit is deactivated, the mechanical pressure element 34 pushes the sealing element 40 towards the outside through the actuator hole 39. The sealing element 40 in turn pushes the closing element 30 against the diaphragm 33 in such a way that the closing element 30 itself reaches the blocking position.

Figure 7:
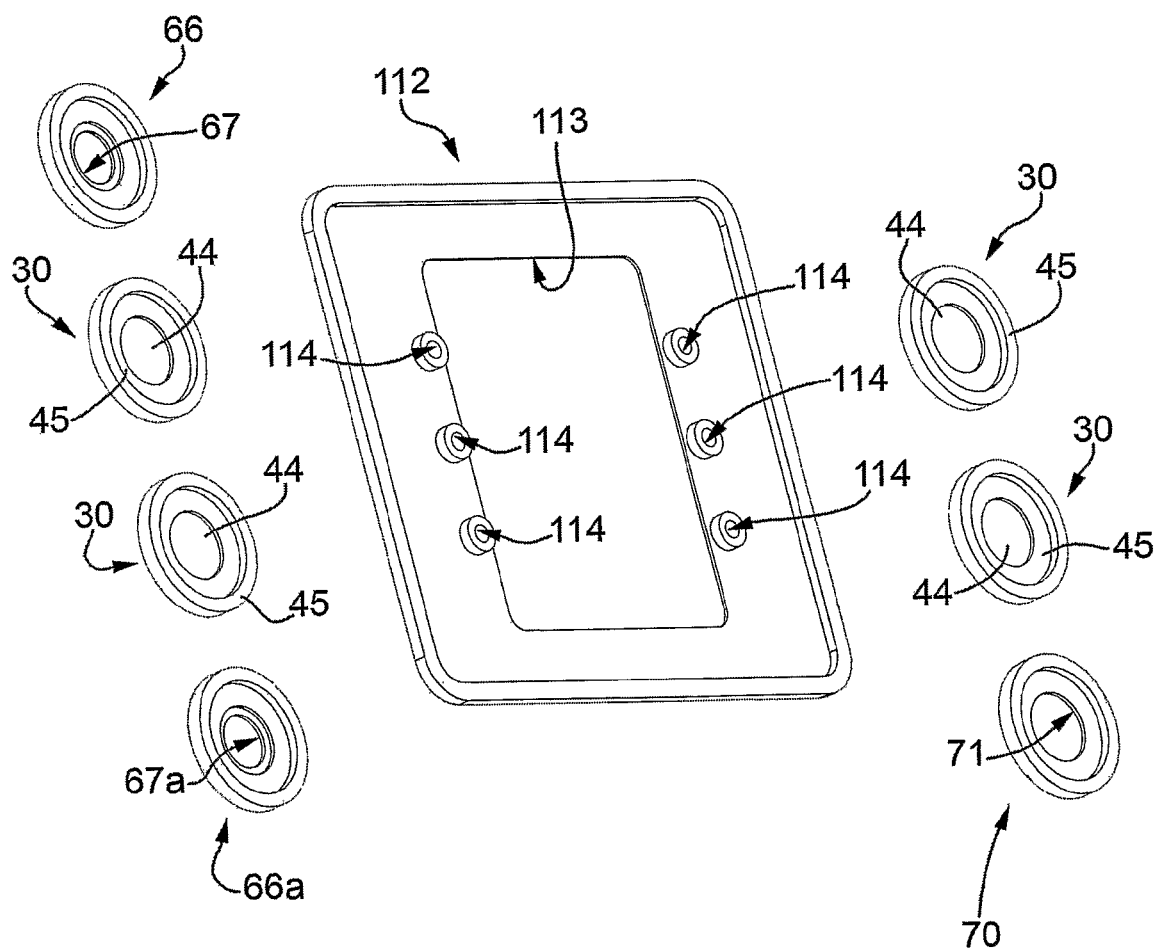
FIG. 7 is a perspective view of components of the device of FIG. 4.

The closing element 30 (also illustrated in FIG. 7) has a membrane pbrtion 44 and a projection 45 that extends along a perimetral edge of the membrane portion 44. In other words, the closing element 30 has a larger thickness at the perimetral edge. This enables improvement of the mechanical resistance of the membrane and fluid tightness between the closing element 30 and the actuator nozzle 36 (in particular, the hollow element 37). The projection 45 has an annular shape.

According to specific embodiments, the membrane portion 44 has a substantially cylindrical shape; in this case, the projection 45 has the shape of a circular ring.

According to some embodiments, the closing element 30 is made up of a single elastomeric material (i.e., an elastomer) or else by a combination (for example, a mixture) of a number of elastomeric materials that are different from one another.

Advantageously, the elastomer comprises (in particular, consists of) a silicone, in particular a silicone rubber. According to some embodiments, the silicone has the following formula:

$$[R_2SiO]_n$$

where n is an integer greater than 4, each R is chosen, independently of the others, in the group consisting of: methyl, ethyl, propyl.

According to some embodiments, the elastomer comprises (i.e., is constituted by) just one silicone or, alternatively, a number of silicones that are different from one another.

According to some embodiments, set underneath the actuator nozzle 36 is a mechanical pressure element 46 (in particular, a spring) for pushing the actuator nozzle 36 itself against the closing element 30.

Figure 24:
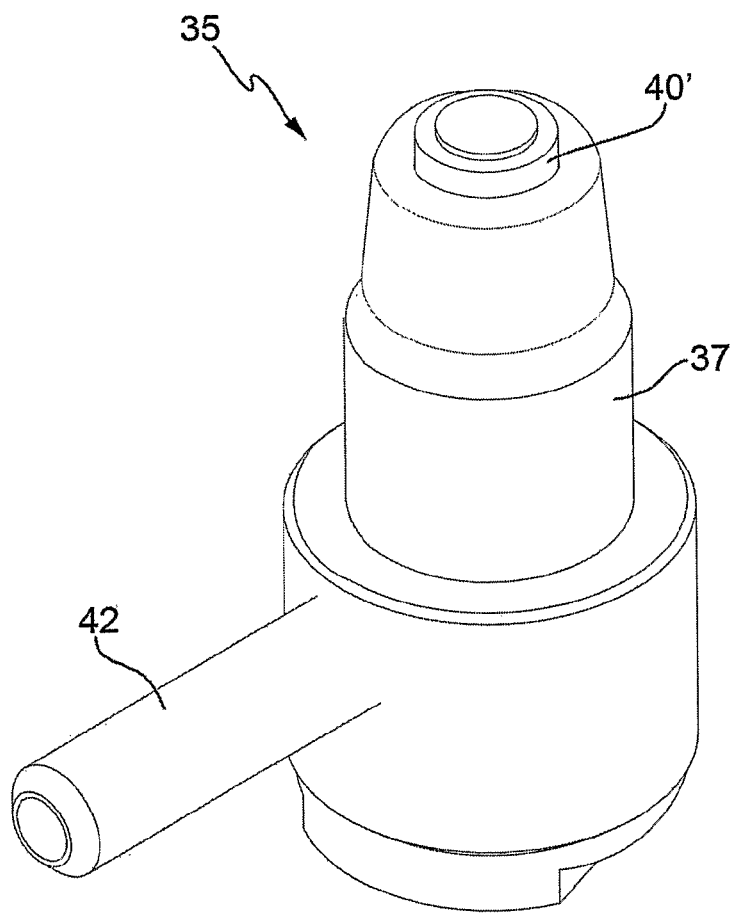
FIG. 24 is a perspective view of a variant of the part illustrated in FIG. 17.
Figure 26:
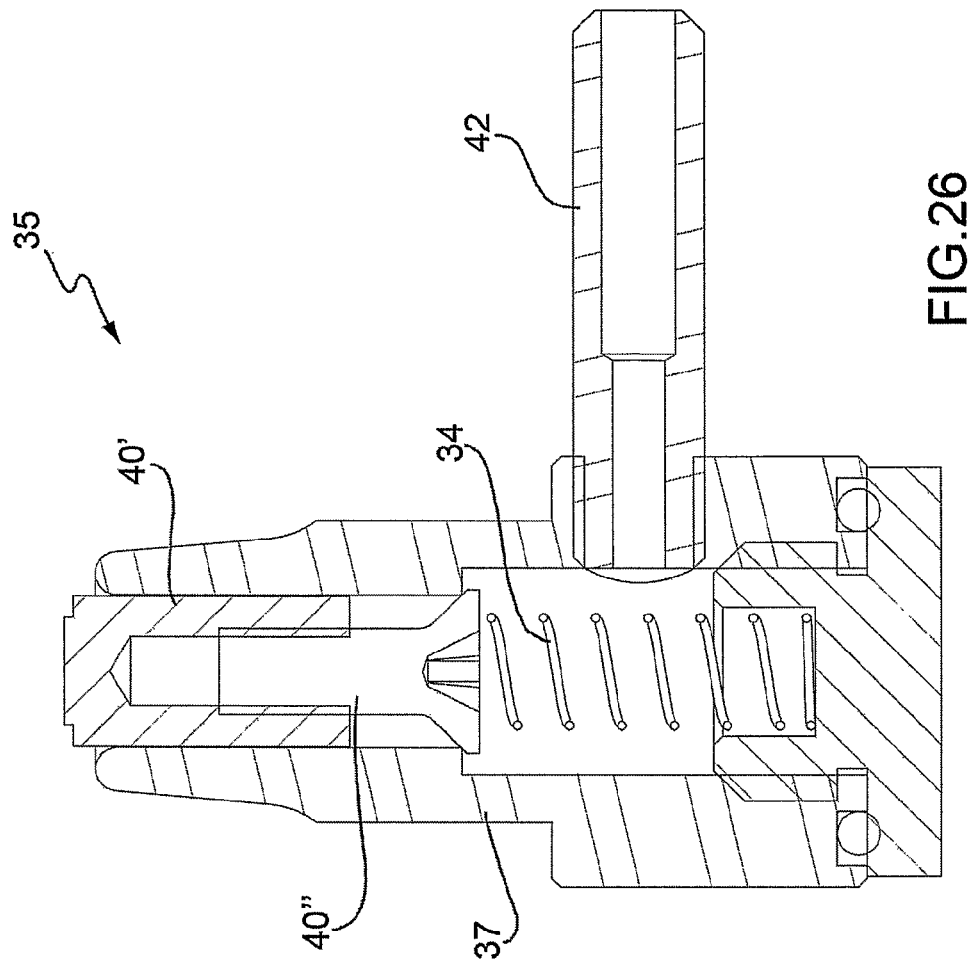
FIG. 26 is a lateral cross-sectional view of the variant of FIG. 24.
Figure 25:
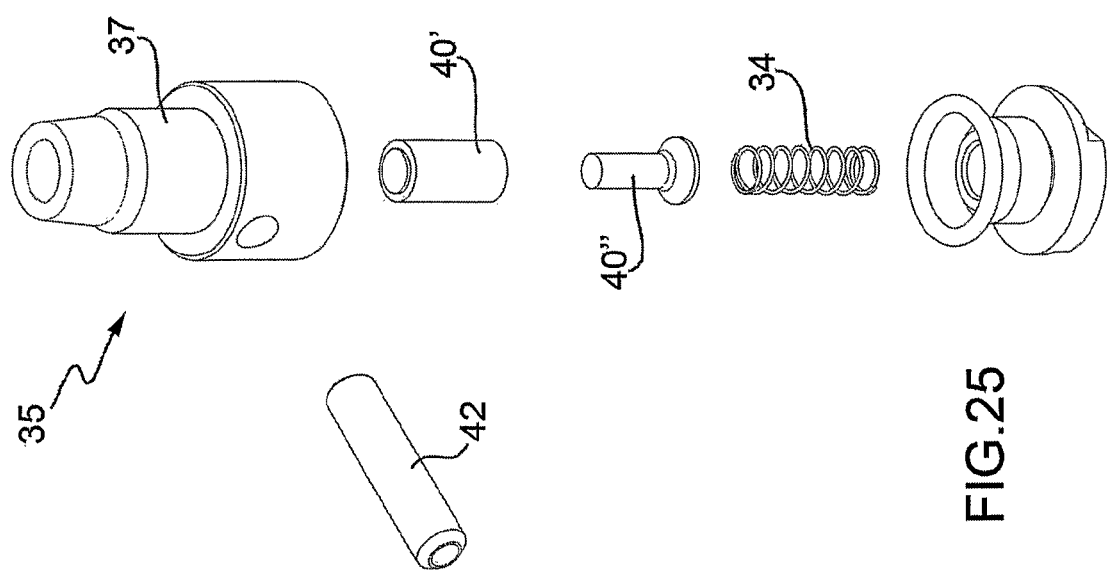
FIG. 25 is an exploded perspective view of the variant of FIG. 24.

According to a variant, the fluid-dynamic actuator 35 has the structure illustrated in FIGS. 24 to 26, in which the sealing element 40 comprises two components 40' and 40", which can be dismantled.

It should be emphasized that the particular structure of the valve V has significant advantages over the prior art.

A first advantage consists in the lower risk of gas contamination (in particular, air) of the sample. In this regard, it should be noted that usually the closing element 30 is partially permeable to gas and that in the solution proposed it is not necessary to supply a jet of air to keep the closing element 30 in the blocking position (by supplying the jet of air, part of the jet of air would enter the duct).

A second advantage consists in the reduction of the head losses when the suction source is functioning (the parts are fitted together so as to present a high fluid tightness).

In the embodiment of FIG. 3, the valves 9 and 11 are illustrated schematically and substantially have the same structure as the valve V described above. In this case, advantageously, the valves 9 and 11 are each connected to a respective suction source 43.

According to some embodiments (not illustrated), the system 1 does not comprise the pressure sources 15 and 25. In this case, the valves 9 and/or 11, instead of being single valves comprise a plurality of valves arranged in succession along the duct 16 and/or 26. In use, the valves arranged in succession are opened and closed in sequence to supply the sample and/or the carrier liquid to the separation unit 3. In this way, the valves arranged in succession work in a way similar to a peristaltic pump.

It should be noted that to work as a peristaltic pump at least three valves arranged in succession are normally necessary.

According to some embodiments, however, the valves 9 and/or 11 each comprise (in particular, consist of) two valves arranged in succession. In these cases, said valves are operated in combination with the valves 10 and/or 12 to work as a peristaltic pump.

These embodiments present some advantages: they do not require integration of cumbersome pressure sources; and they enable in a very precise way regulation of the amount of fluid that is fed to the separation unit 3.

In accordance with the embodiment illustrated in FIG. 3, the system 1 comprises a dielectrophoresis system. The separation unit 3 comprises at least one part of the dielectrophoresis system. According to some embodiments, the separation unit 3 comprises the dielectrophoresis system (in its entirety).

In particular, the system 1 (specifically the dielectrophoresis system) comprises an optical sensor 47. The control assembly 23 is connected to the optical sensor 47 and to the separation unit 3. Advantageously, the optical sensor 46 comprises a video camera 48. In use, the control assembly 23 actuates different active components of the chambers 4 and 5 as a function of what is detected by the optical sensor 47.

According to some embodiments, the separation unit 3 further comprises an operator interface 49 (human/machine interface). Advantageously, the operator interface 49 comprises a personal computer.

According to some embodiments, the dielectrophoresis system and/or its operation are/is as described in at least one of the patent applications Nos. WO0069565, WO2007010367, WO2007049120, the contents of which are integrally recalled herein for completeness of description (and incorporated herein for reference).

According to some embodiments, the system 1 (FIG. 2) comprises a cooling assembly 50, which is designed to cool at least part of the separation unit 3, in particular the main chamber 4 and the recovery chamber 5.

The cooling assembly 50, according to some embodiments, is a Peltier assembly and comprises: a cooling plate 51 having an active surface 52, designed to absorb the heat from the separation unit 3; and a discharging surface 53 for yielding heat. Advantageously, the active surface 52 has a smaller extension than the discharging surface 53.

According to some embodiments, set between the active surface 52 and the separation unit 3 is a mat (in itself known) made of a heat-conductive polymeric material.

The cooling assembly 50 further comprises a heat-transfer plate 54 connected to a conditioning circuit 55, which functions as heat-exchanger device.

The circuit 55 comprises: two ducts 56; a radiator 57, which is set between the two ducts 56; a plurality of fans 58 for cooling a conditioning liquid whilst it flows within the radiator 57; and a pump 59 to cause the conditioning liquid to flow along the ducts 56 and through the radiator 57.

According to the embodiment illustrated in FIG. 3, the system 1 comprises at least one (in the case in point, four) mechanical pressure element 60 (in particular, a spring) for pushing the cooling assembly 50 towards the main chamber 4 and the recovery chamber 5.

With particular reference to FIGS. 16, 18, 13, and 3, the system 1 further comprises two pressure-supply nozzles 61 and 61a arranged between two stretches of the duct 16 and of the duct 26, respectively.

The pressure-supply nozzle 61 comprises a hollow body 62, which is connected to a pressure device 64, and has a pressure-supply hole 63 set at an opposite end with respect to the pressure device 64.

The pressure device 64 comprises a pressure unit 65, which, in turn, comprises the pressure source 15 and a duct (in particular, a first stretch of the duct 16), which connects the pressure source 15 to the pressure-supply nozzle 61.

Set between the pressure-supply hole 63 and a second stretch of the duct 16 is a seal ring 66 (illustrated in FIGS. 7, 16) comprising (in particular, consisting of) a substantially elastic material.

Advantageously, the substantially elastic material is defined as described above with reference to the closing element 30.

According to some embodiments, the seal ring 66 is substantially circular and has: a substantially central hole 67; an internal portion that delimits the hole 67; and a peripheral portion having a larger thickness than an internal portion.

According to some embodiments, the system 1 further comprises at least one mechanical pressure element 68 (in particular, a spring), which is set so as to push the pressure-supply nozzle 63 towards (in particular, against) the seal ring 66. In this way, a smaller dispersion of the pressure (i.e., a better seal) is obtained between the pressure-supply nozzle 63, the seal ring 66 and the second stretch of the duct 16. The mechanical pressure element 68 has the important function of compensating for any possible lack of planarity of the device and regulating the forces of contact applied.

According to advantageous embodiments, the pressure-supply nozzle 61a has the same structure as the pressure-supply nozzle 61, is connected to the pressure device 64 and is pushed towards a respective seal ring 66a by a corresponding mechanical pressure element 68a.

The system 1 further comprises a seat 69 (partially illustrated in FIG. 13), which is designed to house a removable collector (for example, a test tube), of a type in itself known and not illustrated, and is set at the outlet 8.

Set between the duct 27 and the seat 69 is a seal ring 70, which is designed to guarantee a smaller dispersion (i.e., a better seal) between the duct 27 and the seat 69. The seal ring 70 comprises (in particular, consists of) a substantially elastic material.

Advantageously, the substantially elastic material is defined as described above with reference to the closing element 30.

According to some embodiments, the seal ring 70 is substantially circular and has: a substantially central hole 71; an internal portion that delimits the hole 71; and a peripheral portion having a larger thickness than an internal portion.

Figure 4:
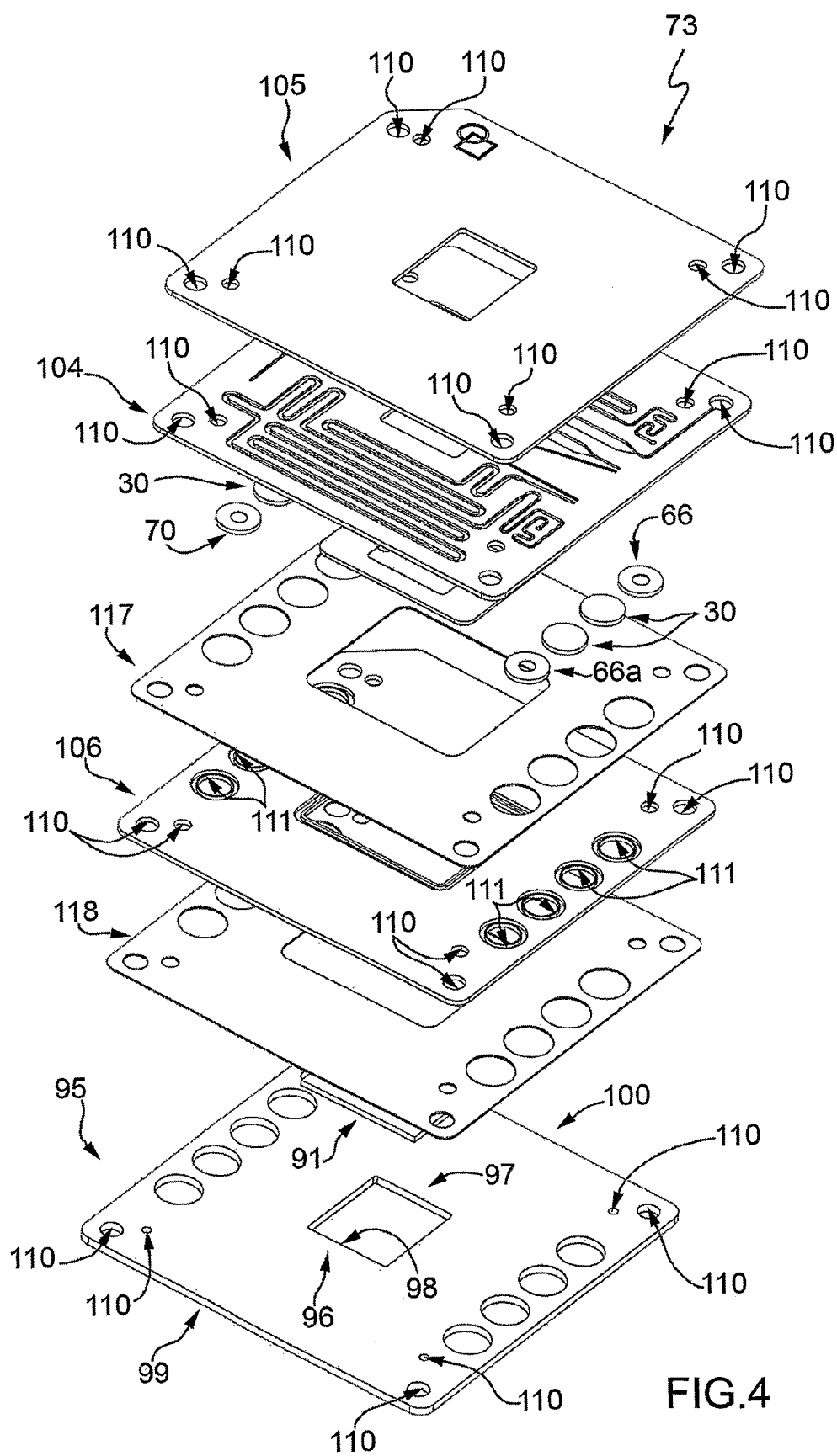
FIG. 4 is an exploded perspective view of a device built in accordance with the present invention.
Figure 10:
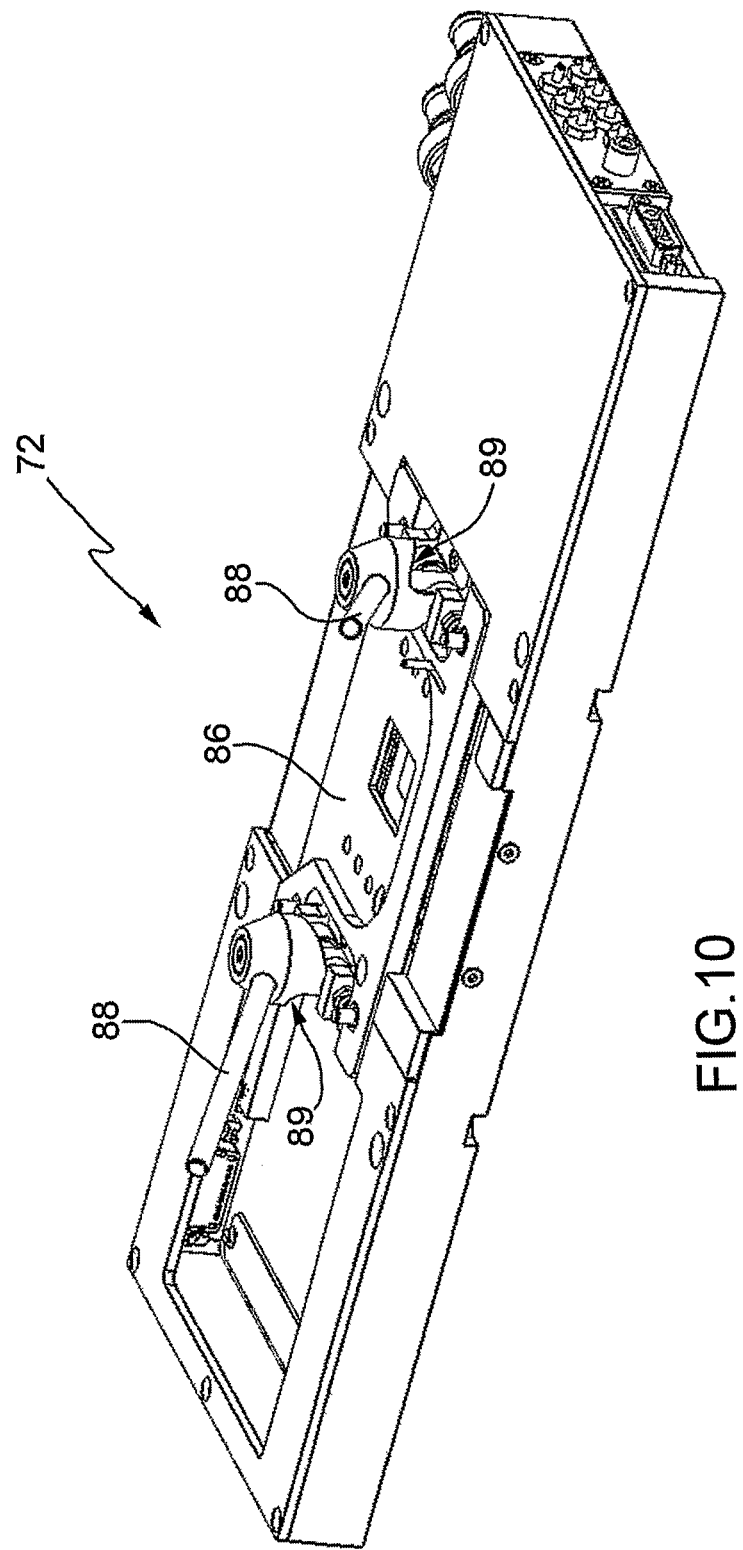
FIG. 10 is a partial perspective view with items removed for reasons of clarity of an apparatus built in accordance with the present invention.
Figure 11:
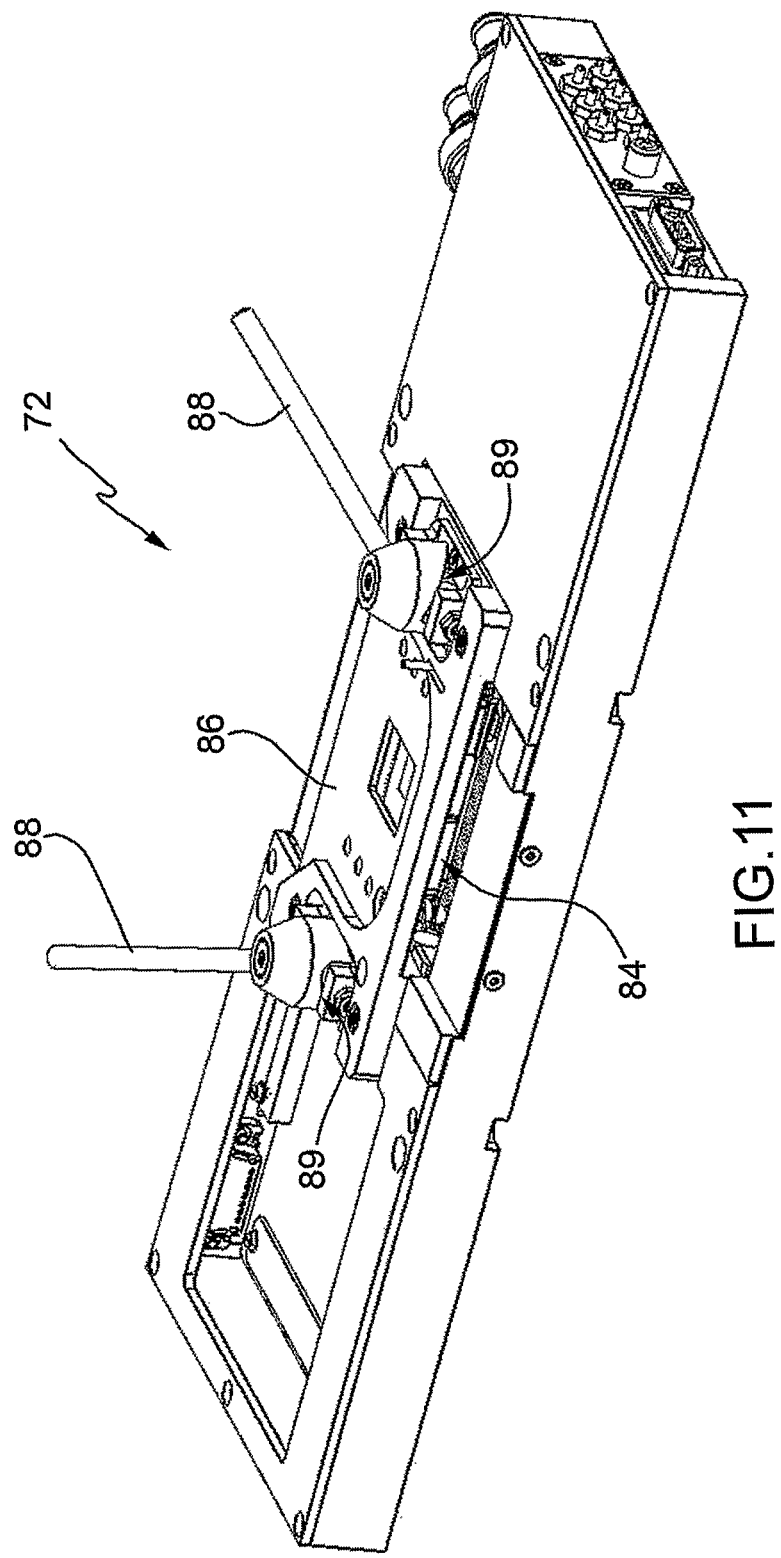
FIG. 11 is a partial perspective view with items removed for reasons of clarity of the apparatus of FIG. 10 in a different operating position.
Figure 21:
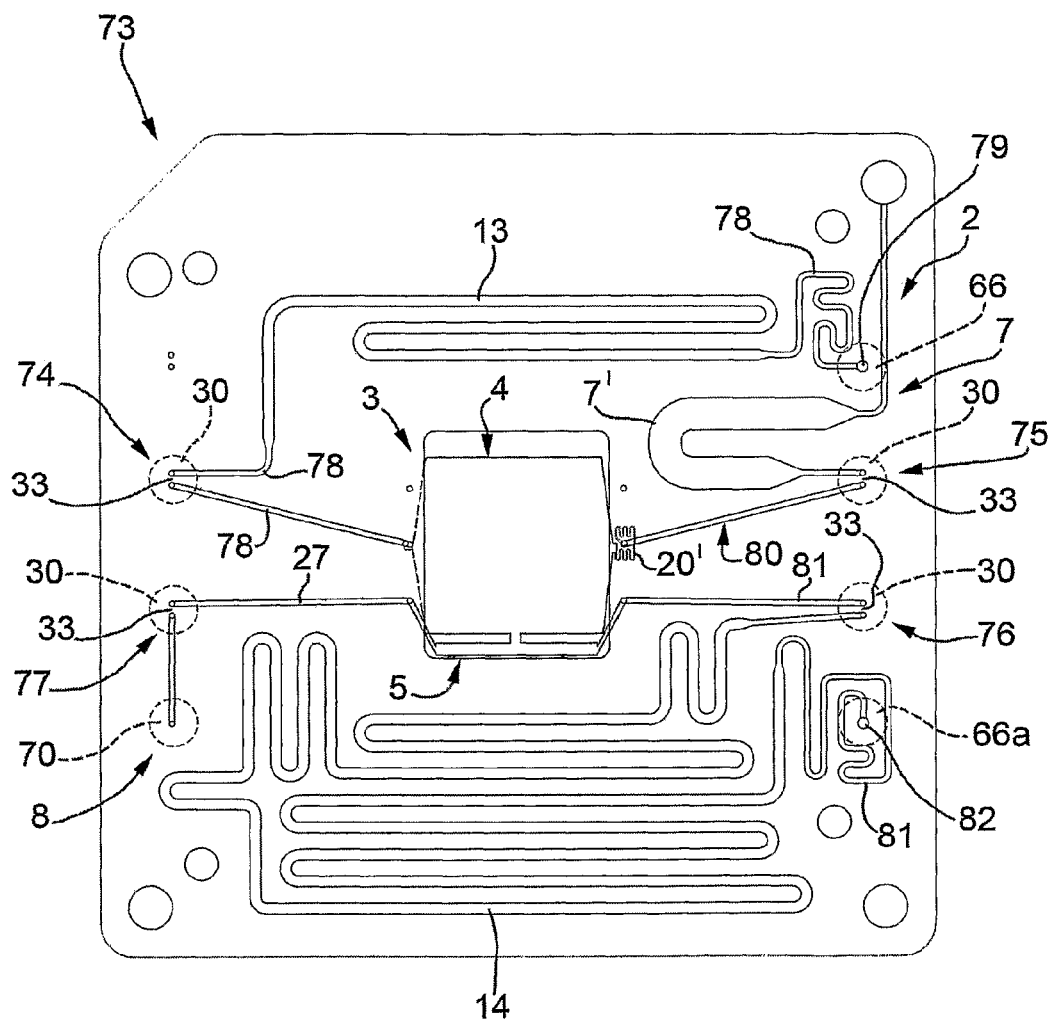
FIG. 21 is a top plan view of a device of FIG. 4.

According to some embodiments, the system 1 comprises two separable portions: a substantially fixed apparatus 72 (an embodiment of the apparatus 72 is partially illustrated in FIGS. 10 and 11) and a device 73 (an embodiment of the device 73 is illustrated in top plan view in FIG. 21 and in exploded view in FIG. 4).

According to a particular aspect of the present invention, a microfluidic system is provided for isolation of particles C1 of at least one given type from a sample, the system 1 comprising: a first inlet 2, through which, in use, the sample is introduced into the system 1; a separation unit 3, which comprises a main chamber 4 and a recovery chamber 5 and is designed to transfer at least part of the particles C1 of the given type from the main chamber 4 to the recovery chamber 5 in a substantially selective way with respect to further particles C2 of the sample; a first outlet 7, connected to the main chamber 4; and a second outlet 8, which is connected to the recovery chamber 5, through which, in use, at least part of the particles C1 of the given type collected in the recovery chamber 5 exit from the system 1; the system 1 being characterized in that it comprises: a first valve 9, set upstream of the main chamber 4; a second valve 10, set between the main chamber 4 and the first outlet 7; a third valve 11, set upstream of the recovery chamber 5; and a fourth valve 12, set between the recovery chamber 5 and the second outlet 8.

According to some embodiments, the system comprises one or more of the characteristics described above in accordance with the first and second aspects of the present invention.

In use, the system 1 (in accordance with one or more of the aspects of the invention referred to above) is used according to the method described hereinafter.

Method

Provided according to a third aspect of the present invention is a method for isolation of particles C1 of at least one given type from a sample by means of a microfluidic system. The microfluidic system is the system 1 or a microfluidic system similar to the system 1. Advantageously, the microfluidic system is the system 1 as described above in accordance with one of the preceding aspects of the present invention. In any case, for reasons of simplicity in the ensuing description of the method the microfluidic system and its parts will be identified with the reference numbers used above for identifying the system 1 and similar or identical parts, respectively.

The method comprises: a step of introduction of the sample into a system 1 through an inlet 2 of the system 1; a separation step, during which at least part of the particles C1 of the given type are separated from further particles C2 within a separation unit 3 of the system 1; a first supply step, which at least partially precedes the separation step and during which at least part of the sample is fed to the separation unit 3 (the first supply step is schematically illustrated in FIGS. 19e-19i); and a recovery step, which is at least partially subsequent to the separation step and during which at least part of the particles C1 of the given type separated in a substantially selective way flow away from the separation unit 3 through an outlet 8 of the system 1 (the recovery step is schematically illustrated in FIGS. 20c and 20d).

According to some embodiments, the system 1 comprises: a valve 9 set between the inlet 2 and the separation unit 3; and a valve 12 set between the outlet 8 and the separation unit 3. During the separation step, the valves 9 and 12 are kept closed.

In particular, the system 1 comprises a valve set between each opening (for example, inlets and/or outlets) of the system 1 towards the outside and the separation unit 3. During the separation step, each of these valves is kept closed.

According to some embodiments, the recovery step is completely subsequent to the separation step.

According to some embodiments, the separation step is completely subsequent to the first supply step.

According to some embodiments, during the separation step, the particles C1 of the given type are transferred from a main chamber 4 to a recovery chamber 5 of the separation unit 3 in a substantially selective way with respect to further particles C2 of the sample (the end of the separation step is illustrated in FIG. 20a).

According to some embodiments, during the separation step, using a system as described in FIG. 2, the particles C1 of a number of given types are transferred from a main chamber 4 to a particular area of the recovery chamber 5 isolated via fluid resistance from the rest of the recovery chamber.

An outlet 7 and an outlet 8 of the system 1 are connected to the main chamber 4 and to the recovery chamber 5, respectively.

Advantageously, the system 1 comprises: the valve 9, which is set upstream of the main chamber 4; a valve 10, set downstream of the main chamber 4; a valve 11, set upstream of the recovery chamber 5; the valve 12, set downstream of the recovery chamber 5. During the separation step, the valves 9, 10, 11, 12 are closed, in particular so as to isolate the main chamber 4 and the recovery chamber 5 with respect to the outside.

The method further comprises: the first supply step, which at least partially precedes the separation step and during which at least part of the sample is fed into the main chamber 4 (the first supply step is schematically illustrated in FIGS. 19e-19i); and a second supply step, which at least partially precedes the separation step and during which the carrier liquid is fed to the recovery chamber 5 (the second supply step is illustrated in FIGS. 19a-19d).

The method further comprises the recovery step, during which the carrier liquid, together with at least part of the particles C1 of the given type, flow away from the recovery chamber 5 through the outlet 8 (the recovery step is schematically illustrated in FIGS. 20*c* and 20*d*).

According to some embodiments, during the step of introduction at least part of the sample is introduced into a reservoir 13 of the system 1.

Advantageously, the separation step occurs by dielectrophoresis. At least during the separation step, the separation unit 3 is cooled.

According to some embodiments, at least one or both of the first and the second supply steps are completely prior to the separation step.

According to some embodiments, the second supply step at least partially precedes the first supply step. Advantageously, the second supply step is completely prior to the first supply step.

According to some embodiments, a first pressure is set to supply the sample to the main chamber 4.

In particular, the first pressure pushes the sample from the reservoir 13 towards the main chamber 4.

According to some embodiments, the first pressure is exerted at least prior to and during the first supply step.

Advantageously, during the recovery step, at least part of the particles C1 of the given type are subjected to vibration; in particular, they are subjected to a pressure that varies in an oscillating way (the frequency of vibration is between 2 Hz and 80 Hz, advantageously from 5 Hz to 40 Hz).

Advantageously, during the first supply step a valve 9 of the system 1, said valve 9 being set upstream of the main chamber 4, and a valve 10 of the system 1, said valve 10 being set between the main chamber 4 and the outlet 7, are open. In particular, during the first supply step, the sample passes through the valve 9.

According to some embodiments, during the first supply step, the sample is subjected to vibration; in particular, it is subjected to a pressure that varies in an oscillating way (the frequency of vibration is between 2 Hz and 80 Hz, advantageously from 5 Hz to 40 Hz).

According to particular embodiments, the system 1 comprises: a duct 16 for connecting the inlet 2 to the main chamber 4; and a duct 20, which is set between the main chamber 4 and the outlet 7 and has a cross section smaller, in particular by at least 100 μm, than the cross section of the duct 16; during the first supply step, the pressure of the sample being detected; supply of the sample being blocked according to the pressure detected, in particular when a pressure higher than a given value is detected.

According to further embodiments, in addition or as an alternative to the detection of pressure one or more of the following detections is made: optical detection of the passage of the sample between the chamber 4 and the duct 20; detection of the variation of the electrical conductivity in an area of connection between the chamber 4 and the duct 20 due to the start of the passage of the sample; detection of the variation of the electrical permittivity in an area of connection between the chamber 4 and the duct 20 due to the start of the passage of the sample; detection of the variation of the thermal resistance in an area of connection between the chamber 4 and the duct 20 due to the start of the passage of the sample; and detection of the variation of the thermal capacity in an area of connection between the chamber 4 and the duct 20 due to the start of the passage of the sample.

In all the above cases, inflow of the sample 40 is blocked when it is found that the sample starts to enter the duct 20.

According to some embodiments, during the second supply step, a valve 11 of the system 1, said valve 11 being set upstream of the recovery chamber 5, and a valve 12, said valve 12 being set between the recovery chamber 5 and the outlet 8, are open.

Advantageously, a second pressure is set to supply the carrier liquid to the recovery chamber 5. In particular, the second pressure pushes the carrier liquid from a reservoir 14 of the system 1 towards the recovery chamber 5. During the second supply step, the carrier liquid passes through the valve 11.

According to some embodiments, the second pressure is exerted at least before and during the second supply step.

During the recovery step the valves 11 and 12 are open.

According to some embodiments, the method comprises a step of discharge, which is at least partially subsequent to the separation step and at least partially prior to the recovery step and during which at least part of the further particles C2 of the sample are made to flow away from the main chamber 4 through the outlet 7; the discharge step is schematically illustrated in FIGS. 20*b* and 20*c*. Advantageously, the discharge step is completely subsequent to the separation step and/or completely prior to the recovery step.

During the discharge step, the valves 10 and 11 are open so as to supply the carrier liquid to the main chamber 4.

Carrying-out of the discharge step enables reduction of the risks of part of the further particles C2 that are recalled from the main chamber 4 by the flow of the carrier liquid through the recovery chamber 5 from passing, during the recovery step, through the outlet 8.

In practice, according to some embodiments, the valves 11 and 12 are opened so as to fill the recovery chamber 5 with the carrier liquid. At this point, the valves 9 and 10 are opened, in such a way that the sample will fill the main chamber 4. The valves 9, 10, 11 and 12 are, then, closed, and the particles C1 of the given type are brought in a substantially selective way from the main chamber 4 to the recovery chamber 5. At this point, the valves 11 and 10 are opened so as to cause at least part of the further particles C2 to flow away from the chamber 4.

According to some embodiments, the particles C1 of the given type are arranged within the recovery chamber 5 in such a way that, during the discharge step, they remain at least in part inside the recovery chamber 5 itself. In particular, the particles C1 of the given type are arranged laterally with respect to (i.e., not in front of) a channel 6 for connection between the main chamber 4 and the recovery chamber 5. Specifically, the particles C2 are arranged between the channel 6 and a duct 26 for connection to the outlet 8.

According to some embodiments, the system 1 comprises a valve (FIGS. 2 and 27), which is set between the recovery chamber and the outlet 7 (or a further outlet not illustrated). The chamber 5 comprises: a first area 5' which is hydraulically connected to the duct 27 (and hence to the valve 12); a second area 5", hydraulically connected to the duct 28 (and hence to the valve 29); and a further area, which defines a terminal stretch of the duct 26 (and is hence connected to the valve 11).

During the second filling step, the valves 12 and 11 are open so as to fill the first area 5' of the recovery chamber 5, which connects the valves 12 and 11; the valves 11 and 29 are open for filling the second area 5" of the recovery chamber 5 that connects the valves 11 and 29.

According to specific embodiments, the valves 12, 11 and 29 are opened so as to fill the first area 5' (FIGS. 27*b* and 27*c*); at this point, the valve 12 is closed and the second area 5" is filled (FIG. 27*d*).

During the separation step, at least part of the particles C1 of the given type and at least part of the particles C3 of at least one second given type are transferred into the recovery chamber 5 (FIGS. 28a and 28b) (in particular, into the second area 5"). The recovery step comprises a first recovery substep, during which at least part of the particles C1 of the given type is brought in a substantially selective way into the first area 5' (FIG. 28d) and, subsequently, at least part of the particles C1 of the given type is made to flow away from the first area 5' through the outlet 8 by supplying to the recovery chamber 5 further carrier liquid (FIG. 28e).

The recovery step comprises a second recovery substep, during which at least part of the particles C3 is made to exit from the recovery chamber 5 through the outlet 8 by supplying to the recovery chamber 5 further carrier liquid.

Advantageously, during the second recovery substep, at least part of the particles C3 is brought into the first area 5' (FIGS. 28e and 28f) and, subsequently, at least part of the particles C3 is made to flow away from the first area 5' through the outlet 8 (FIG. 28g).

According to some embodiments, the method comprises a flushing step, during which further particles C2 present in the main chamber 4 are removed from the channel 6. During the flushing step, the valves 11 and 10 are opened (FIG. 28c). Advantageously, during the flushing step, the valve 29 is closed and the particles C1 and C3 are arranged in the second area 5". Advantageously, during the flushing step, the valve 12 is closed. Advantageously, during the flushing step, the valve 9 is closed.

Advantageously, the flushing step is at least partially (in particular, completely) subsequent to the recovery step and at least partially (in particular, completely) prior to the recovery step.

According to some embodiments, during the recovery step, the first drop of carrier liquid that exits from the outlet 8 is detected; when the first drop is detected, outflow from the recovery chamber 5 is blocked.

According to some embodiments, a number of recovery steps succeed one another, changing the containers arranged in the proximity of the outlet 8 whenever at least one drop is detected.

According to some embodiments, carbon dioxide is fed into the system 1. In this way, the presence of oxygen inside the system 1 is reduced or eliminated. The presence of oxygen inside the system can lead to formation of bubbles during the various steps of the method.

According to alternative embodiments, the carrier liquid (and/or possibly the sample) is degassed by means of ultrasound before introduction into the system 1 (or into the separation unit 3).

Advantageously, the sample and the carrier liquid are used at a temperature higher than 20° C., in particular higher than 25° C. Also this reduces the risk of formation of bubbles.

According to some embodiments, the method is applied using a system 1 defined in accordance with the first aspect of the present invention.

According to some embodiments, the system 1 comprises two separable portions: a substantially fixed apparatus 72 (an embodiment of the apparatus 72 is partially illustrated in FIGS. 10 and 11) and a device 73 (an embodiment of the device 73 is illustrated in top plan view in FIG. 21 and in exploded view in FIG. 4). The device 73 is advantageously disposable and designed to be connected to the apparatus 72.

According to some embodiments, only part of the sample is brought into the main chamber 4. In practice, the sample is subjected to a plurality of successive partial separations.

Microfluidic Device

Provided according to a fourth aspect of the present invention is the device 73 for isolation of particles C1 of at least one given type from a sample. The device 73 comprises: the inlet 2, through which, in use, the sample is introduced into the device 73; and the separation unit 3, which comprises a main chamber 4 and a recovery chamber 5. The separation chamber 3 (in particular, the main chamber 4) is connected to the inlet 2. In particular, the separation unit 3 comprises part of the dielectrophoresis system.

In use, when the device 73 is mounted within the apparatus 72, the separation unit 3 is designed to transfer at least part of the particles C1 of the given type from the main chamber 4 to the recovery chamber 5 in a substantially selective way with respect to further particles C2 of the sample.

According to some embodiments, the device 73 comprises the outlet 7 connected to the main chamber 4; the outlet 8 is connected to the recovery chamber 5.

Through the outlet 8, in use, at least part of the particles C1 of the given type collected in the recovery chamber 5 exit from the device 73.

The outlet 7 is designed to enable the sample to enter freely within the main chamber 4, thus functioning as breather.

The device 73 further comprises: a valve portion 74, which is set upstream of the main chamber 4 (in particular, between the main chamber 4 and the inlet 2); and a valve portion 75, which is set between the main chamber 4 and the outlet 7.

The valve portion 74 is designed to form part of the valve 9. The valve portion 75 is designed to form part of the valve 10.

The device also comprises: a valve portion 76, which is connected to the recovery chamber 5; and a valve portion 77, which is set between the recovery chamber 5 and the outlet 8.

In particular, the recovery chamber 5 is set between the main chamber 4 on one side and the third and fourth valve portions 76, 77 on the other side; the main chamber 4 is set between the recovery chamber 5 on one side and the first and second valve portions 74 and 75 on the other side.

The valve portion 75 is designed to form part of the valve 11. The valve portion 76 is designed to form part of the valve 12.

According to some embodiments, at least one of the valve portions 74, 75, 76 and 77 comprises the closing element 30, which is designed to pass between a blocking position, in which the closing element 30 is set so as to separate two stretches of a respective channel of the device 73, and an opening position, in which the closing element 30 is set in such a way that the two stretches are connected to one another. Advantageously, each valve portion 74, 75, 76 and 77 comprises a respective closing element 30.

Advantageously, the closing element 30 is defined as described above in relation to the system 1. In particular, the closing element 30 has a membrane part, which comprises, in particular is made of, a substantially elastic material.

According to some embodiments, at least one, in particular each, of the valve portions 74, 75, 76 and 77, comprises the diaphragm 33, which is set between the two stretches of the duct of the device 73. In the blocking position the closing element 30 is in contact with the diaphragm 33; in the opening position the closing element 30 is set at a distance from the diaphragm 33.

At least one, in particular each, of the valve portions 74, 75, 76 and 77 comprises at least one hole in a channel of the device 73. In particular, each closing element 30 is set in a point corresponding to two respective holes of a corresponding channel, said holes being separated from one another by a respective diaphragm 33. Each of these holes has a diameter ranging from 0.1 to 0.7 mm. According to specific embodiments, each hole has a diameter of approximately 0.5 mm.

According to some embodiments, each valve portion 74, 75, 76 and 77 corresponds to a part of the valve V described above without the fluid-dynamic actuator 35.

At least one of the closing elements 30 can be actuated by an actuator external to the device 73; in particular, the external actuator forms part of the apparatus 72. More specifically, each of the closing elements 30 can be actuated by a respective actuator external to the device 73; in particular, the external actuators form part of the apparatus 72.

At least one, in particular each, of the closing elements 30 is at least partially exposed and set facing outwards. In this way, the possibility of coupling of the closing element 30 with the respective external actuator and an interaction thereof is rendered more convenient.

According to some embodiments, the device 73 further comprises: the reservoir 13, which is set between the inlet 2 and the valve portion 74 and is designed to collect the sample introduced through the inlet 2; and a channel 78, which connects the reservoir 13 to the main chamber 4 and along which the valve portion 74 is set. In particular, the channel 78 constitutes a part of the duct 16.

Advantageously, the channel 78 has a cross section of equivalent diameter ranging from 0.9 mm to 50 µm. In particular, the channel 78 has a width ranging from 0.7 to 0.1 mm and a depth ranging from 1.00 to 0.15 mm. According to specific embodiments, the channel 78 has a width of approximately 0.5 mm and a depth of from approximately 0.25 to approximately 0.5 mm. The particular paths of the channel 78 contribute to reduction of the risk of the air entering the device 73.

Advantageously, the reservoir 13 has a volume of from 5 µL to 100 µL, in particular a width ranging from 3 to 0.8 mm and a depth ranging from 1.5 to 0.25 mm.

According to specific embodiments, the reservoir 13 has a volume of approximately 35 µL, a width of approximately 1 mm, and a depth of approximately 0.5 mm.

Advantageously, the valve portion 74 is set between the reservoir 13 and the main chamber 4.

According to some embodiments, the device 73 comprises a supply hole 79. In particular, the supply hole 79 is set at the inlet 2. The reservoir 13 is set between the supply hole 79 and the main chamber 4. The channel 78 connects the supply hole 79 to the main chamber 4.

According to some embodiments, the device 73 comprises the seal ring 66, which surrounds the supply hole 79 outwards.

Advantageously, the seal ring 66 is defined as described above in relation to the system 1 and, in particular, is designed to couple with a respective pressure-supply nozzle 61.

According to some embodiments, the device 73 comprises a channel 80 (corresponding to part of the duct 20), which is set between the main chamber 4 and the outlet 7 and comprises the stretch 20'. The stretch 20' has a cross section smaller, in particular by at least 100 µm, than the cross section of the channel 78 (the stretch 20' is more clearly illustrated in FIG. 9).

Advantageously, the stretch 20' has a width of less than 150 µm, a depth of less than 110 µm, and a length greater than 2 mm. Advantageously, the stretch 20' has a width greater than 100 µm, a depth greater than 30 µm, and, in particular, a length of less than 6 mm.

According to some embodiments, the device 73 comprises the reservoir 14, which is designed to contain the carrier liquid.

Advantageously, the reservoir 14 has a volume ranging from 10 mL to 100 µL, a width ranging from 5 to 0.8 mm, and a depth ranging from 1.5 to 0.25 mm.

According to specific embodiments, the reservoir 14 has a volume of approximately 150 µL, a width of approximately 1 mm, and a depth of approximately 0.5 mm.

The device 73 comprises a channel 81, which connects the reservoir 14 to the recovery chamber 5 and along which the valve portion 76 is set.

In particular, the channel 81 constitutes a part of the duct 26.

Advantageously, the channel 81 has a cross section of equivalent diameter ranging from 0.9 mm to 200 µm. In particular, the channel 81 has a width ranging from 0.7 to 0.25 mm and a depth ranging from 0.7 to 0.15 mm. According to specific embodiments, the channel 81 has a width of approximately 0.5 mm and a depth of approximately 0.25 mm.

The particular paths of the channel 81 contribute to reduction of the risk of the air entering the device 73.

According to some embodiments, the valve portion 76 is set between the reservoir 14 and the recovery chamber 5. According to some embodiments, the device 73 comprises a supply hole 82. The reservoir 14 is set between the supply hole 82 and the recovery chamber 5, the channel 81 connecting the supply hole 82 to the recovery chamber 5.

According to some embodiments, the device 73 comprises the seal ring 66a, which surrounds the supply hole 82 outwards.

Advantageously, the seal ring 66a is defined as described above in relation to the system 1 and, in particular, is designed to couple with a respective pressure-supply nozzle 61a.

The device 73 comprises electrical connectors 83 (illustrated in FIG. 3) for electrical connection of the device 73 itself to the apparatus 72. Advantageously, the electrical connectors comprise (in particular, consist of) at least one electrical circuit, in particular a connection electrical printed circuit (PCB).

Figure 31:
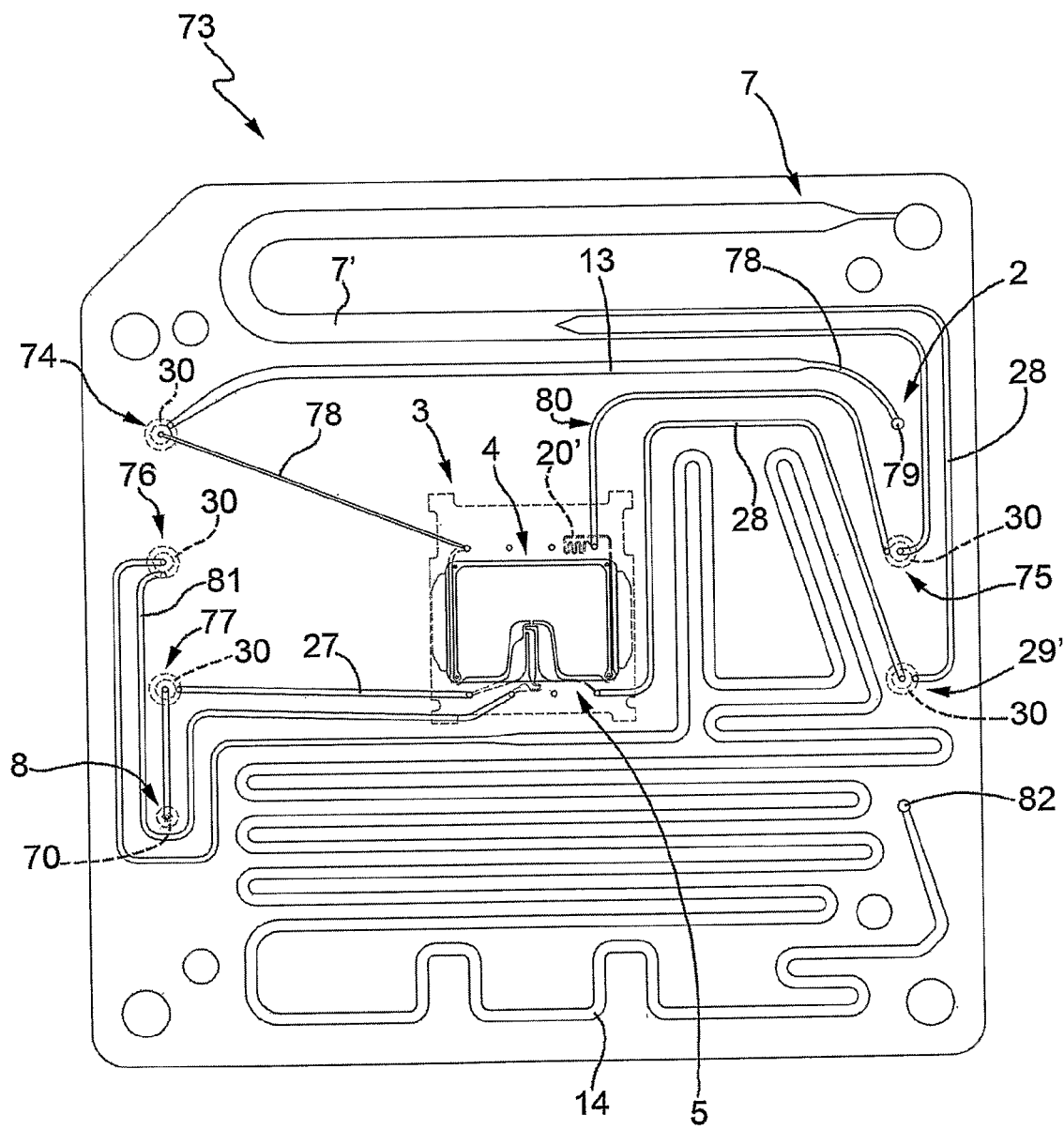
FIG. 31 is a top plan view of a device built in accordance with the present invention.

According to the embodiment illustrated in FIG. 31, the device 73 comprises a further valve portion 29' designed to form a part of the valve 29. In this case, the valve portion 29' is set between the recovery chamber 5 and an outlet of the device 73 (i.e., of the system 1). Said outlet can be a further outlet with respect to the outlets 7 and 8 described above or can coincide with the outlet 7 or the outlet 8 (in the embodiment illustrated in FIG. 31, said outlet corresponds with the outlet 7).

Consequently, according to some embodiments, the device 73 comprises a further outlet; the valve portion 29' is set between the recovery chamber 5 and the further outlet; optionally, the further outlet corresponds to the outlet 7.

The device 73 further comprises the duct 28, which hydraulically connects the chamber 5 (in particular, the second area 5") to the further outlet. The valve portion 29' is set in a position corresponding to the duct 28.

In these cases, the chamber 5 comprises: the first area 5', which is hydraulically connected to the duct 27 (and hence to the valve portion 77); the second area 5", which is hydraulically connected to the duct 28 (and hence to the valve portion 29'); and the further area, which defines a terminal stretch of the channel 81 (i.e., of the duct 26) (and is hence connected to the valve portion 76).

The duct 28 has a cross section of equivalent diameter ranging from 0.9 mm to 200 µm. In particular, the duct 28 has a width ranging from 0.7 to 0.25 mm and a depth ranging from 0.7 to 0.15 mm. According to specific embodiments, the duct 28 has a width of approximately 0.5 mm and a depth of approximately 0.25 mm.

Figure 27:
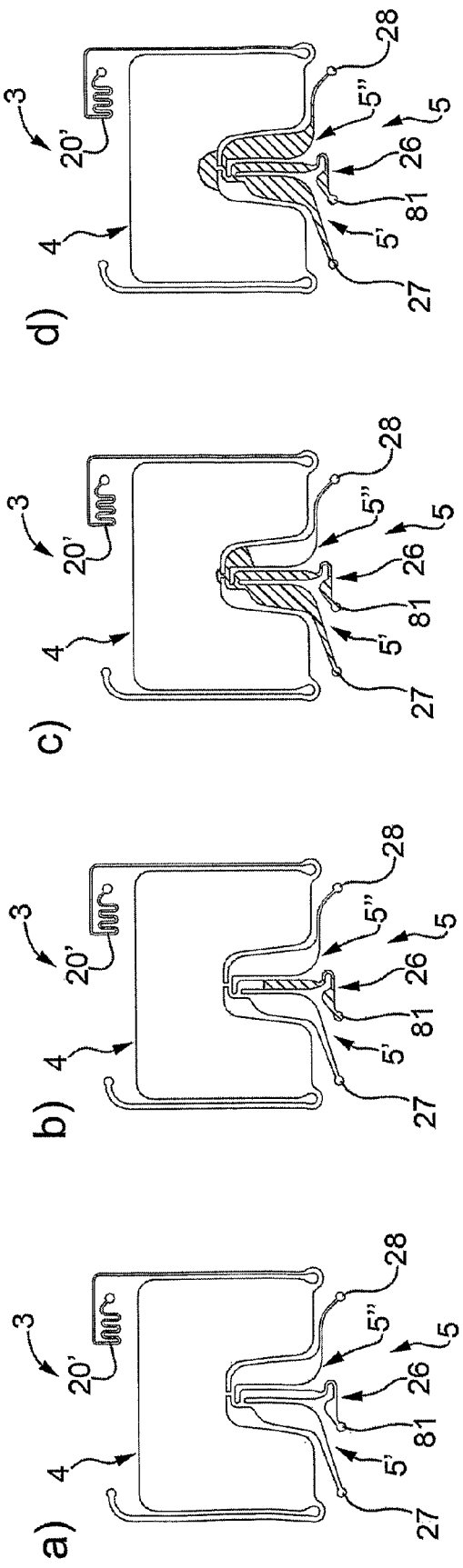
FIG. 27 (*a-h*) and FIG. 28 (*a-g*) illustrate a detail of the device of FIG. 31 in various operating steps.
Figure 27:
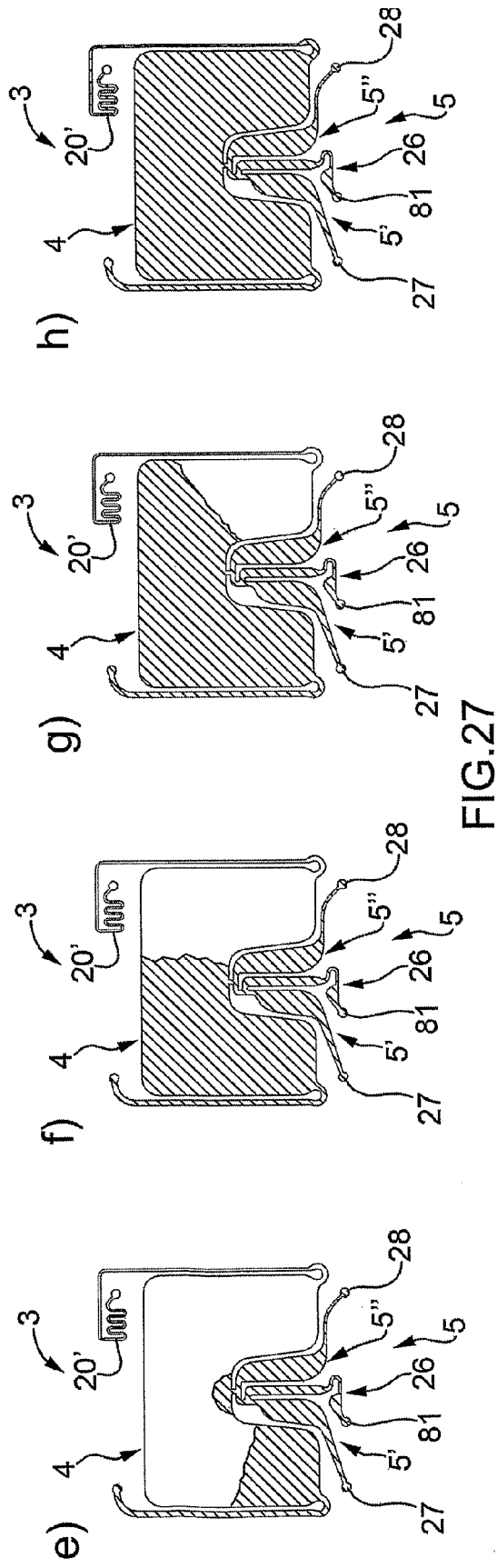
Figure 28:
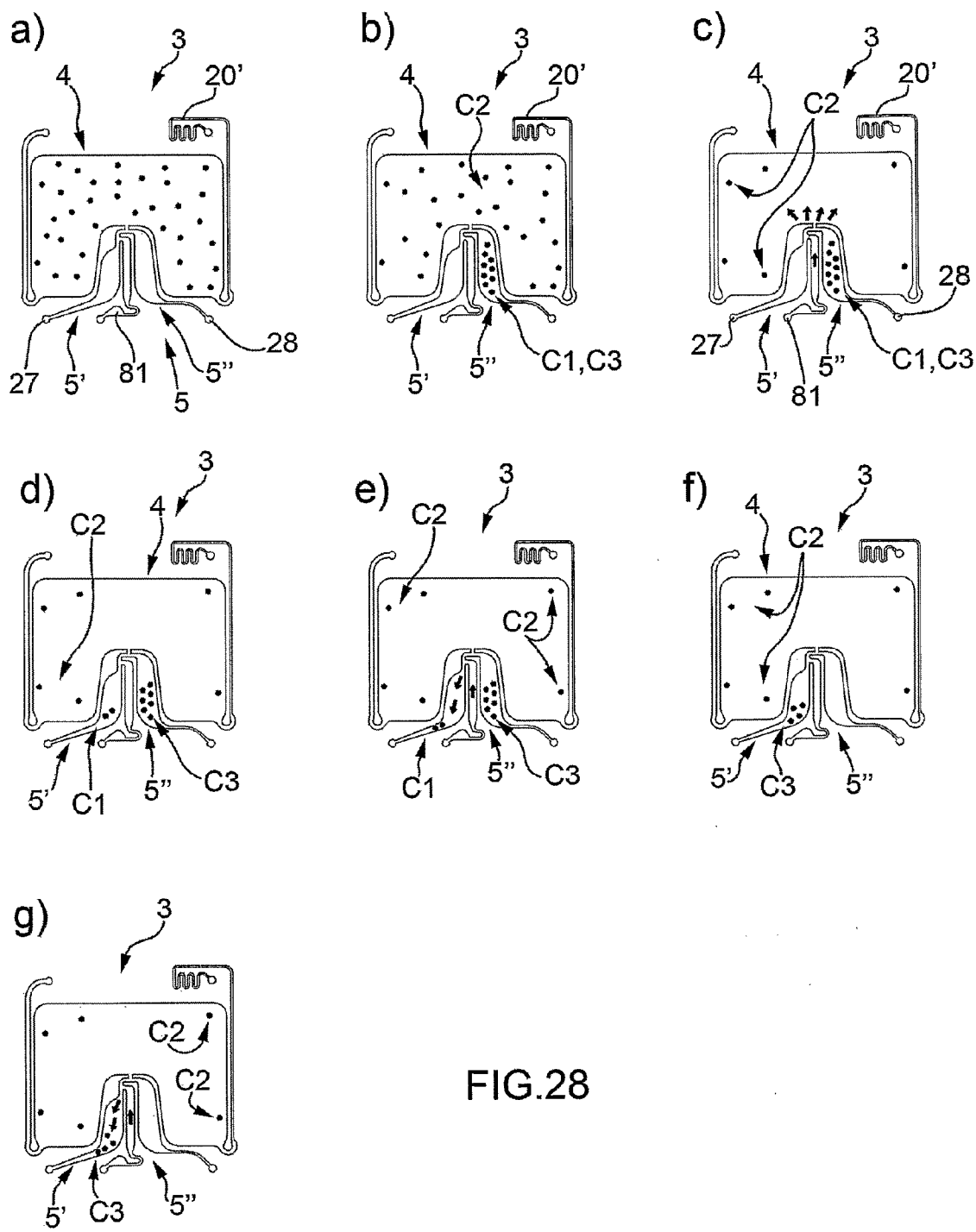

The device 73 of FIG. 31 is designed to form part of the system 1 illustrated in FIG. 2 and to function according to what is illustrated in FIGS. 27 and 28.

Apparatus

According to a fifth aspect of the present invention, an apparatus 72 for isolation of particles C2 of at least one given type from a sample is provided.

The apparatus 72 comprises: a seat 84 (illustrated open in FIG. 11 and closed in FIG. 10) for housing a microfluidic device (in particular, the device 73) for isolation of the particles C1 of the given type from the sample; electrical connectors 85 (illustrated in FIGS. 3 and 13) for electrical connection of the apparatus 1 to the microfluidic device; and the control assembly 23, connected to the electrical connectors 85. According to some embodiments, the apparatus 72 comprises part of the dielectrophoresis system.

Figure 12:
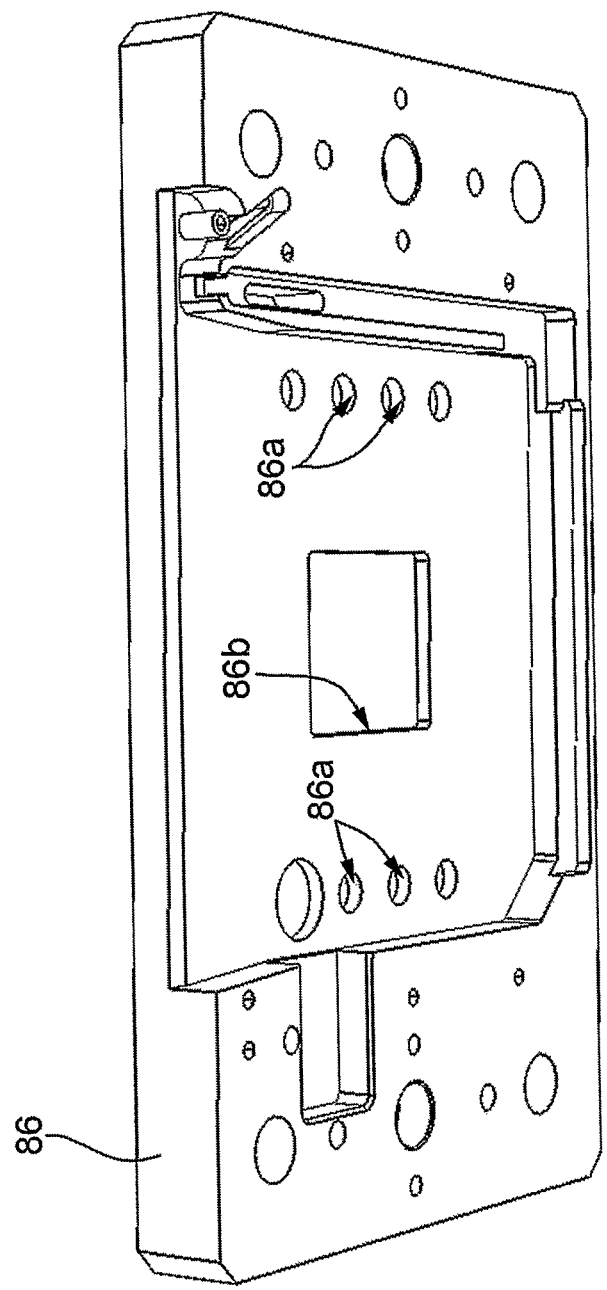
FIG. 12 is a perspective view from beneath of a detail of the apparatus of FIGS. 10 and 11.
Figure 13:
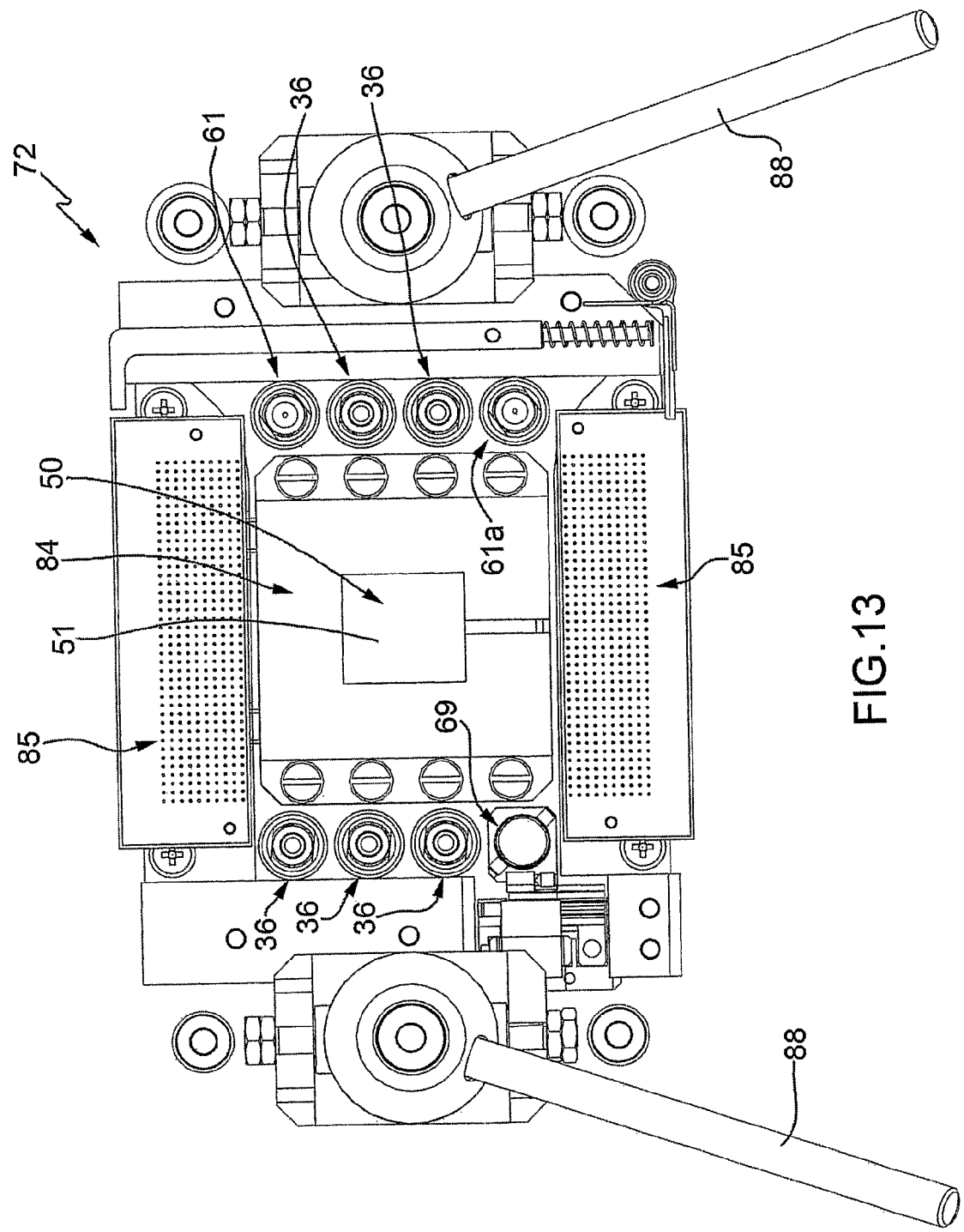
FIG. 13 is a top plan view of a part of the apparatus of FIGS. 10 and 11, with items removed for reasons of clarity.

According to some embodiments, the apparatus 72 comprises a hatch 86, which is illustrated in a raised position in FIG. 11 and in a lowered position in FIG. 10. The bottom face of the hatch 86 is illustrated in FIG. 12.

The apparatus 72 comprises: at least four fluid-dynamic actuators 35, each of which is designed to form a part of a respective valve and comprises a respective actuator nozzle 36 (see, in particular, FIG. 13), which has a respective actuator hole 39; and at least two pressure-supply nozzles 61 and 61a, which each have a respective pressure-supply hole 63 and 63a.

Each fluid-dynamic actuator 35 is designed to move a respective closing element 30 external to the apparatus 72, in particular belonging to said microfluidic device 73. In particular, each fluid-dynamic actuator 35 is designed to couple (coming into contact) with a respective closing element 30.

The apparatus comprises: at least the pressure device 64, connected to the pressure-supply nozzles 61 to determine a pressure at the pressure-supply holes 63 and 63a; and at least one pressure device 87, which is connected to the actuator nozzles 36 (FIG. 3) and is designed to cause suction in a region corresponding to at least one of the actuator holes (FIGS. 14 and 15).

When the hatch 86 is in a raised position, the seat 84 is open and accessible from outside (FIG. 11); in particular, when the hatch 86 is in a raised position, the microfluidic device (in particular, the device 73) can be inserted underneath the hatch 86 itself. In use, once the microfluidic device has been inserted under the hatch 86, the hatch 86 is lowered (FIG. 10) and the microfluidic device is brought into the seat 84. This is done by turning the handles 88, which have at one end thereof cam profiles 89. The cam profiles 89, by turning, push the hatch 86 downwards, overcoming the resistance of springs (which are in themselves known and are not illustrated), which tend to keep the hatch 86 in a raised position.

According to what is illustrated in FIG. 12, the hatch 86 comprises holes 86a for inspecting the valves 9, 10, 11 and 12 and an opening 86b for rendering the chambers 4 and 5 visible.

According to some embodiments, the apparatus 72 comprises a pressure assembly 90 (FIG. 3), comprising the pressure devices 64 and 87. The pressure assembly 90 comprises at least one pump.

According to some embodiments, the pressure device 64 comprises the pressure unit 65 and at least one pressure unit 65a, each of which is connected to the respective pressure-supply nozzle 61 and 61a. The pressure units 65 and 65a can be operated separately and are each designed to define a pressure at (in particular, a jet of air through) the corresponding pressure-supply hole 63 and 63a.

According to some embodiments, the pressure device 64 comprises at least one pressure source 15 (and/or 25) (FIGS. 1, 2 and 3). At least one between the pressure unit 65 and the pressure unit 65a comprises a corresponding duct (in particular, for the pressure unit 65, a first stretch of the duct 16; for the pressure unit 65a, a first stretch of the duct 26), which connects the pressure source 15 and/or 25 to the respective pressure-supply nozzle 61 and/or 61a.

The apparatus 72 comprises: the pressure sensor 21 for detecting the pressure along the aforesaid duct; and the blocking device 22, which is designed to interrupt the transmission of pressure to the respective pressure-supply nozzle 61 and/or 61a. The control assembly 23 is connected to the pressure sensor 21 and to the blocking device 22 for actuating the blocking device 22 as a function of the pressure detected.

According to some embodiments, the pressure sensor 21 is set in a position corresponding to the pressure device 64.

Advantageously, the blocking device 22 comprises a relief valve, which is, in particular, set along the aforesaid duct (a first stretch of the duct 16 and/or a first stretch of the duct 26).

According to the embodiments illustrated in FIGS. 1 and 2, the blocking device 22 is set along a first stretch of the duct 16, and the pressure sensor 21 is designed to detect the pressure within the duct 16 itself.

According to some embodiments (not illustrated), the apparatus 72 comprises a pressure sensor for detecting the pressure at the duct 26 and a blocking device. The pressure sensor and the blocking device are defined and arranged in a way similar to what has been described above with reference to the pressure sensor 21 and to the blocking device 22.

According to some embodiments, the apparatus 72 comprises at least one vibration device 17 and/or 17a, which is set along the aforesaid duct (a first stretch of the duct 16 and/or a first stretch of the duct 26) and is designed to cause variation in an oscillating way of the pressure defined by the pressure source 15 and/or 25 at the respective pressure-supply hole 63 and/or 63a (FIG. 3).

Advantageously, the vibration device 17 and/or 17a comprises a diaphragm pump.

Advantageously, the apparatus 72 comprises two vibration devices 17 and 17a, which are arranged along a first stretch of the duct 16 and a first stretch of the duct 26, respectively. The vibration devices 17 and 17a are designed to cause variation in an oscillating way of the pressure defined by the corresponding pressure sources 15 and 25 at the pressure-supply holes 63 and 63a, respectively.

According to some embodiments, the pressure device 87 comprises at least four suction units 41, each connected to a respective actuator nozzle 36. The suction units 41 can be operated separately from one another and are each designed to carry out at least one operation of suction at a corresponding actuator hole 39.

Advantageously, the pressure device 87 comprises at least one suction source 43. At least one of the suction units 41 comprises: a respective duct 42, which connects the suction source 43 to the respective actuator nozzle 36; and a blocking device (in itself known and not illustrated), which is designed to interrupt the transmission of the suction to said respective actuator nozzle 36.

Advantageously, the aforesaid blocking device comprises an element chosen in a group consisting of: a valve set along the duct 42, and an actuation of the pressure source 43, said actuation being designed to activate or deactivate the pressure source 43 itself.

According to some embodiments, at least one of the actuator nozzles 36 comprises (FIGS. 14 and 15) a corresponding mechanical pressure element 34, which is designed to exert a pressure through the respective actuator hole 39 towards the outside.

Advantageously, the mechanical pressure element 34 comprises a spring, at an external end of which the sealing element 40 is set.

Advantageously, one or more of the actuator nozzles 36 comprises a hollow element 37 for housing the mechanical pressure element 34 and for connecting the respective suction unit 41 to the corresponding actuator hole 39. The hollow element 37 is equipped with one end having the corresponding actuator hole 39.

According to some embodiments, the apparatus 72 comprises at least one mechanical pressure element 46 for pushing one or more of the actuator nozzles 36 towards the microfluidic device. Advantageously, the mechanical pressure element 46 comprises (in particular, is constituted by) a spring.

Advantageously, the apparatus 72 comprises a plurality of mechanical pressure elements 46, each for pushing a respective actuator nozzle 36 towards the microfluidic device. In particular, each mechanical pressure element 46 is designed to push a respective actuator nozzle towards (against) a corresponding closing element 30.

According to some embodiments, one or more (in particular, all) of the fluid-dynamic actuators 35 is defined as described above in relation to the system 1.

According to some embodiments, the apparatus 72 comprises at least one mechanical pressure element 68 and/or 68a for pushing at least one respective pressure-supply nozzle 61 and/or 61a towards (in particular, against) the microfluidic device.

According to some embodiments, the apparatus 72 comprises the cooling assembly 50, which is designed to cool at least part of the microfluidic device. In particular, the part of the microfluidic device from which heat is absorbed is the separation unit 3.

Advantageously, the cooling assembly 50 is defined in accordance with what has been described in relation to the system 1.

In particular, the cooling assembly 50 comprises: a cooling plate 51 having an active surface 52 designed to absorb heat from the microfluidic device; and a discharging surface 53 for yielding heat. The active surface 52 is of dimensions smaller than the discharging surface 53.

Advantageously, the cooling assembly 50 comprises a Peltier and a heat-exchanger device (in particular, the conditioning circuit 55) connected to the Peltier.

Advantageously, the apparatus 72 comprises at least one mechanical pressure element 60 (in particular, a plurality thereof) for pushing the cooling assembly 50 towards the microfluidic device.

According to one embodiment (not illustrated), the apparatus 72 comprises at least one further actuator nozzle 36 and one further corresponding suction unit 41.

According to some embodiments, the control assembly 23 is connected to the pressure devices 64 and 87 for regulating the pressure and/or the suction at each actuator nozzle 36 and/or each pressure-supply nozzle 61 independently of one another.

According to some embodiments, the apparatus 72 comprises a collection unit for collecting a carrier liquid containing at least part of the particles C1 of the given type. In particular, the collection unit comprises a seat 69 (FIG. 13), which is designed to house a removable collector (for example, a test tube), of a type in itself known and not illustrated, and is set at the outlet 8.

Advantageously, the apparatus 72 comprises a detector (for example, a video camera in itself known and not illustrated) for detecting when a drop of said carrier liquid enters the collection unit.

Said detector is connected to the control assembly 23. In use, when the detector notices the passage of a drop, the control assembly interrupts the outflow of the carrier liquid from the recovery chamber 5.

According to some embodiments, parts of the device 73 and/or of the apparatus 72 are defined, even only as regards some aspects taken separately from the others, as the similar parts of the system 1 and/or vice versa.

Microfluidic Device

Provided according to a further aspect of the present invention is a device 73 for substantial isolation of particles C1 of at least one given type from a sample. The device 73 comprises: the inlet 2, through which, in use, the sample is introduced into the device 73; a separation unit 3, which is designed to separate in a substantially selective way at least a part of the particles C1 of the given type from further particles C2 of the sample; and an outlet 8, which is connected to the separation unit 3 and through which, in use, at least part of the particles C1 of the given type separated in a substantially selective way exit from the device 73.

The device 73 comprises: a valve portion 74, set between the inlet 2 and the separation unit 3; and a valve portion 77, set between the outlet 8 and the separation unit 3. In particular, the device 73 comprises a valve portion set between each opening of the device 73 towards the outside and the separation unit 3.

According to some embodiments, the device 73 is defined, even only as regards some aspects taken separately from the others, as in accordance with the fourth aspect of the present invention.

Advantages

It should be emphasized that the present invention has various advantages, in addition to the ones referred to above, as compared to the state of the art. Amongst these we mention the following.

The particles C1 of the given type can be brought into the recovery chamber 5 whilst the separation unit 3 is isolated from the outside (the valves 9-10 are closed). In this way, evaporation both of the part liquid of the sample and of the carrier liquid is substantially prevented. By avoiding evaporation, there do not occur return currents from the recovery chamber 5 to the main chamber 4 (or vice versa), thus reducing the risk of the particles C1 and/or C2 moving in a non-controlled way (specifically, particles C1 brought into the recovery chamber 5 do not return into the main chamber 4; likewise, further cells C2 are not recalled into the recovery chamber 5). Furthermore, by avoiding evaporation, there does not occur an increase in the concentration of the salts in the separation unit 3. The increase of the concentrations of the salts can cause increases in conductivity and local power dissipation with corresponding problems (damage to possible electrodes present in the chambers 4 and 5).

The various steps are controlled by the control assembly 23. This determines a higher degree of reproducibility (according to the prior art, an operator had to introduce the sample and the recovery liquid by means of a pipette).

The presence of carbon dioxide within the device 73 before loading the sample reduces the risk of formation of bubbles inside the chambers 4 and 5. The bubbles reduce the volume of the sample analysed and can prevent recovery of the particles C1 of the given type above all if they occupy a region corresponding to the channel 6.

The sample comes into contact only with the device 73, which is advantageously disposable. In this way, it is not necessary to wash the various parts of the system 1, and the risks of contamination between successive samples are drastically reduced. In this regard, it should also be emphasized that the majority of the active components, which are more complex and costly, are set in the apparatus 72, which is not disposable.

The system 1 presents extremely small unused volumes thanks to the fact that the sample is kept in the reservoir 13 very close to the separation unit 3. The reservoirs 13 and 14 form both part of the device 73.

The present patent application claims the priority of two Italian patent applications (specifically, BO2009A000152, BO2009A000153), the contents of which are integrally recalled herein. In particular, the Italian patent applications are incorporated herein by reference.

Further characteristics of the present invention will emerge from the ensuing description of some merely illustrative and non-limiting examples of embodiment of the device 73 and of operation of the system 1.

EXAMPLE 1

This example describes production of a silicon-based chip 91 of the separation unit 3. The chip is more clearly represented in FIG. 9 and in exploded view in FIG. 8.

The chip has a width of 19.9 mm, a length of 24.5 mm, and a thickness of 1.2 mm and comprises: a silicon substrate 92 (thickness: 600 μm); a spacer element 93, which delimits the chambers 4 and 5 and the channel 6 (thickness: 90 μm); and a transparent lid 94, in particular made of borosilicate or quartz (500 μm).

The substrate 92 was obtained using CMOS (complementary metal-oxide semiconductor) standard technologies. Laminated at 90° on the substrate 92 was a layer of photo-polymer (Dryresist® in particular Ordyl SY300, Elga Europe) (thickness: 90 μm). The layer of photo-polymer was then partially protected by a photo-lithographic mask (a transparent slide printed with a resolution of 24000 DPI) and subjected to UV radiation (150 W) for 15 seconds so as to polymerize the areas of the layer of photo-polymer exposed (i.e., not covered by the dark parts of the mask). Once selective polymerization was completed, the non-polymerized part was removed by immersing the laminated substrate in a developer (BMR developer—mixture of xylene, 2-butoxy-ethyl acetate, mixture of isomers).

At this point, the substrate 91 with the corresponding spacer element 93 thus obtained was put in an oven at 50° C. for one hour to obtain drying.

The lid 94 (made of glass and having a thickness of 500 μm) was obtained by milling. The holes of the lid 94 presented a frusto-conical shape with the bottom part having a diameter of 700 μm and the top part having a diameter of 1200 μm.

The lid 94 was pressed against the spacer element 8 for 80 minutes at a temperature of 95° C. to obtain a thermal bond.

EXAMPLE 2

This example describes a PCB (printed circuit board) 95 partially illustrated in perspective in FIG. 4.

The PCB 95 comprised four layers of copper prepared using photo-lithographic techniques of a known type (see, for example, the previous example).

The PCB 95 had a main structure made of composite material of epoxy polymer and glass fibre. The shape of the PCB 95 illustrated in FIG. 4 was obtained by milling the main structure.

The copper layers were embedded in the main structure and were exposed outwards with four hundred pads oriented (in FIG. 4) upwards (i.e., towards the chip 91) and arranged (two hundred, in the area indicated by the arrow 96 and, two hundred, in the area indicated by the arrow 97) on opposite sides of an opening 98 of the PCB 95 itself.

These pads were electrically connected to further four hundred pads oriented (in FIG. 4) downwards; two hundred of the further pads were arranged at one edge of the PCB in the area indicated by the arrow 99; two hundred of the further pads were arranged in a position corresponding to one edge of the PCB 95 in the area indicated by the arrow 100.

The pads arranged in the areas 96 and 97 were coated with gold designed to connect electrically the PCB 95 to the chip 91.

The pads arranged in the areas 98 and 99 were coated with gold and functioned as electrical connectors for electrical connection of the device 73 to the apparatus 72 and, in particular, to the control assembly 23.

The PCB 95 had a thickness of approximately 1.6 mm.

EXAMPLE 3

This example describes the connection between the chip 91 and the PCB 95.

The chip 91 was aligned to the centre of the PCB 95 using a "pick & place" device and glued on the PCB 95 itself with an adhesive.

The four hundred pads of the PCB 95 arranged in the areas 96 and 97 were connected to the chip 91 by means of known wire-bonding techniques with aluminium wires, each of which connected a respective pad to one side 101 or 101a of the chip 95. The wires were then coated with an epoxy resin that was made to polymerize so as to protect the wires themselves.

Figure 8:
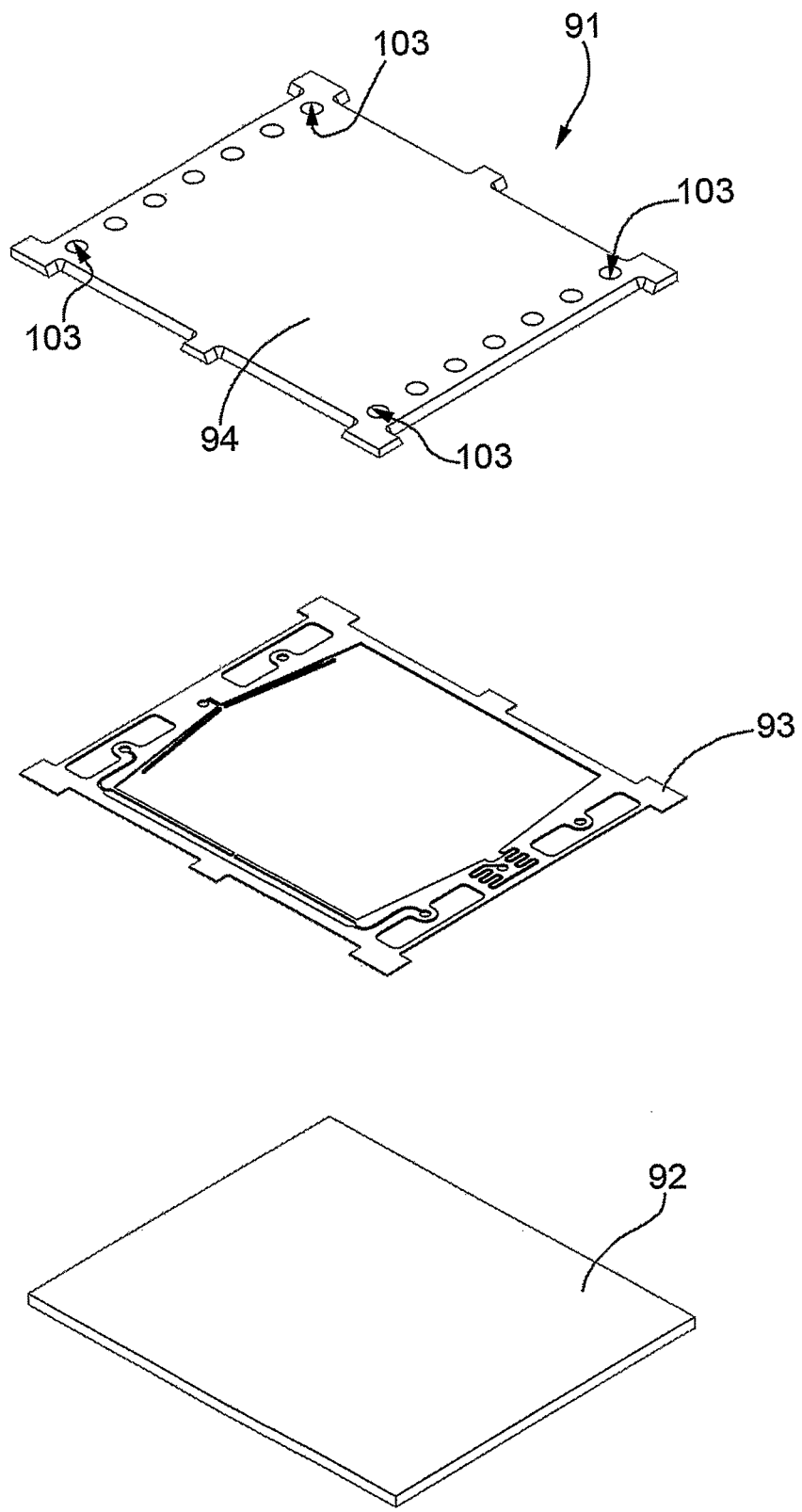
FIG. 8 is an exploded perspective view of a component of the device of FIG. 4.
Figure 9:
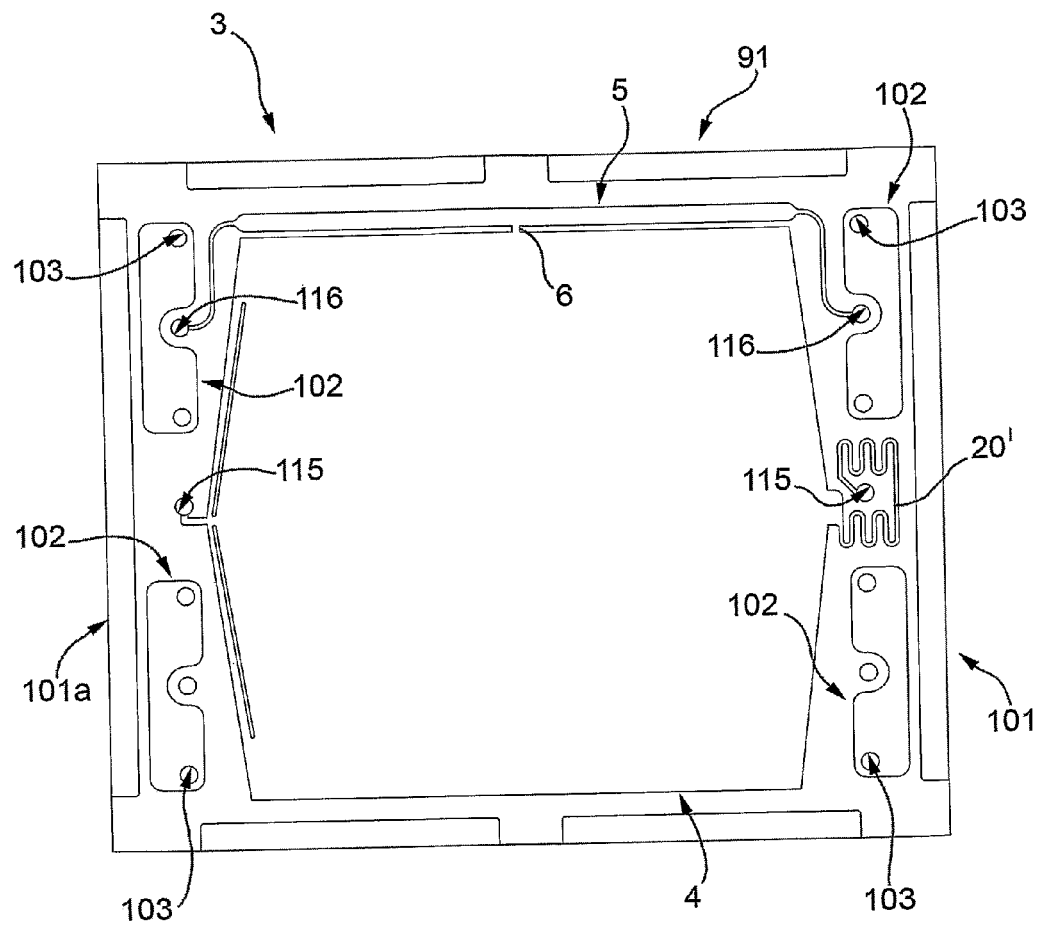
FIG. 9 is a top plan view of the component of FIG. 8.

At this point, an amount of 1 μL of paint containing silver was introduced into each of four chambers 102 (FIG. 9) that were arranged at the corners of the chip 91 through four of the holes of the lid 94 (said holes are designated in FIGS. 8 and 9 by the number 103). The paint was used for creating an electrical connection between the silicon substrate 92 and the lid 94.

Figure 30:
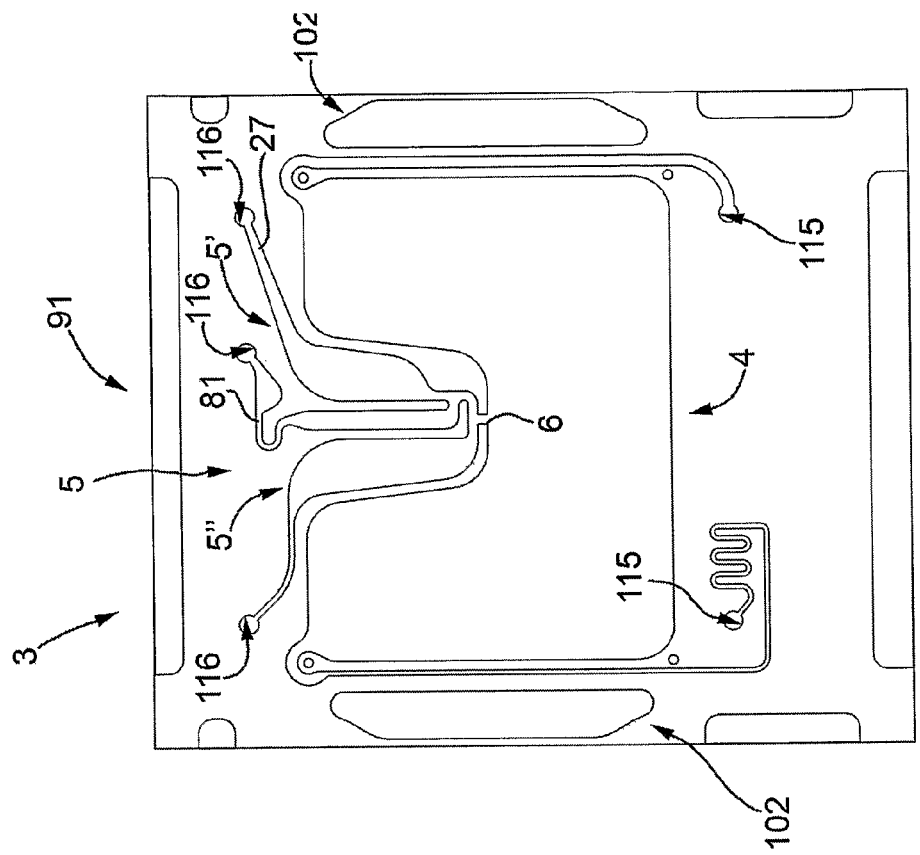
FIG. 30 is a top plan view of the component of FIG. 29.
Figure 29:
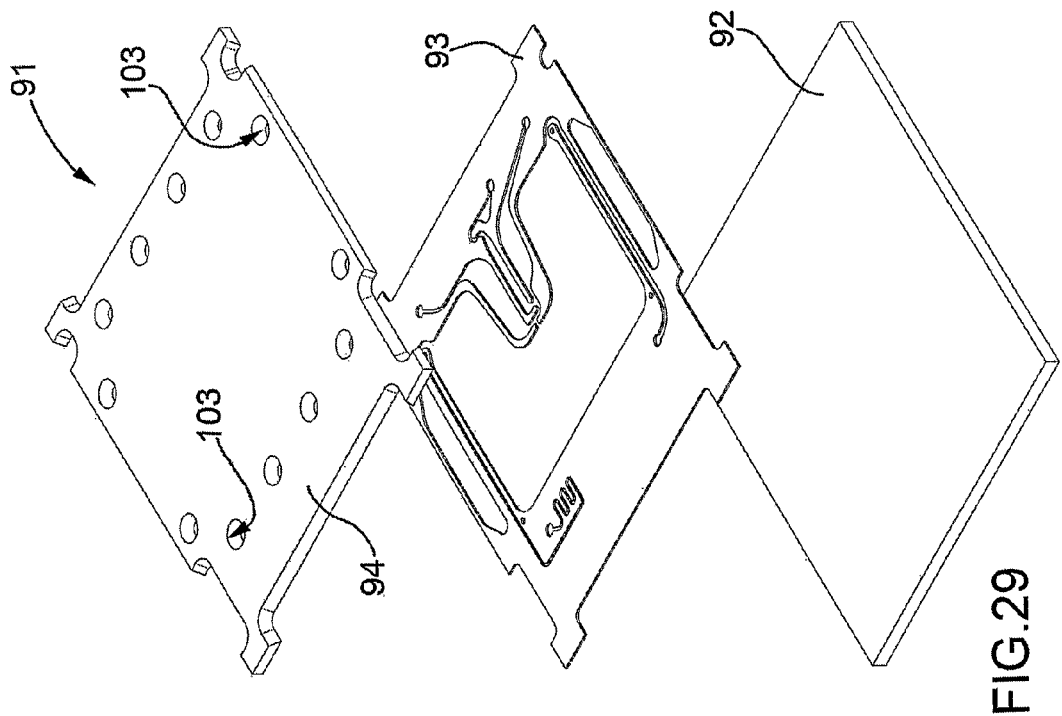
FIG. 29 is an exploded perspective view of a component of the device of FIG. 31.

FIGS. 29 and 30 illustrate a variant of the chip 91. Said variant can be produced and assembled so as to obtain the device 73 illustrated in FIG. 31 in a way similar to what has been described in Examples 1 to 3.

EXAMPLE 4

This example describes production of an intermediate plate 104 made of PMMA, a top plate 105 made of Plexiglas, and a supporting plate 106 made of Plexiglas (FIG. 4).

The plates 104, 105 and 106 had a thickness of approximately 1 mm and were obtained by milling. After milling, a satin finish was carried out for removing the burrs deriving from milling. The plates 104, 105 and 106 were then washed with ultrasound bath.

Figure 5:
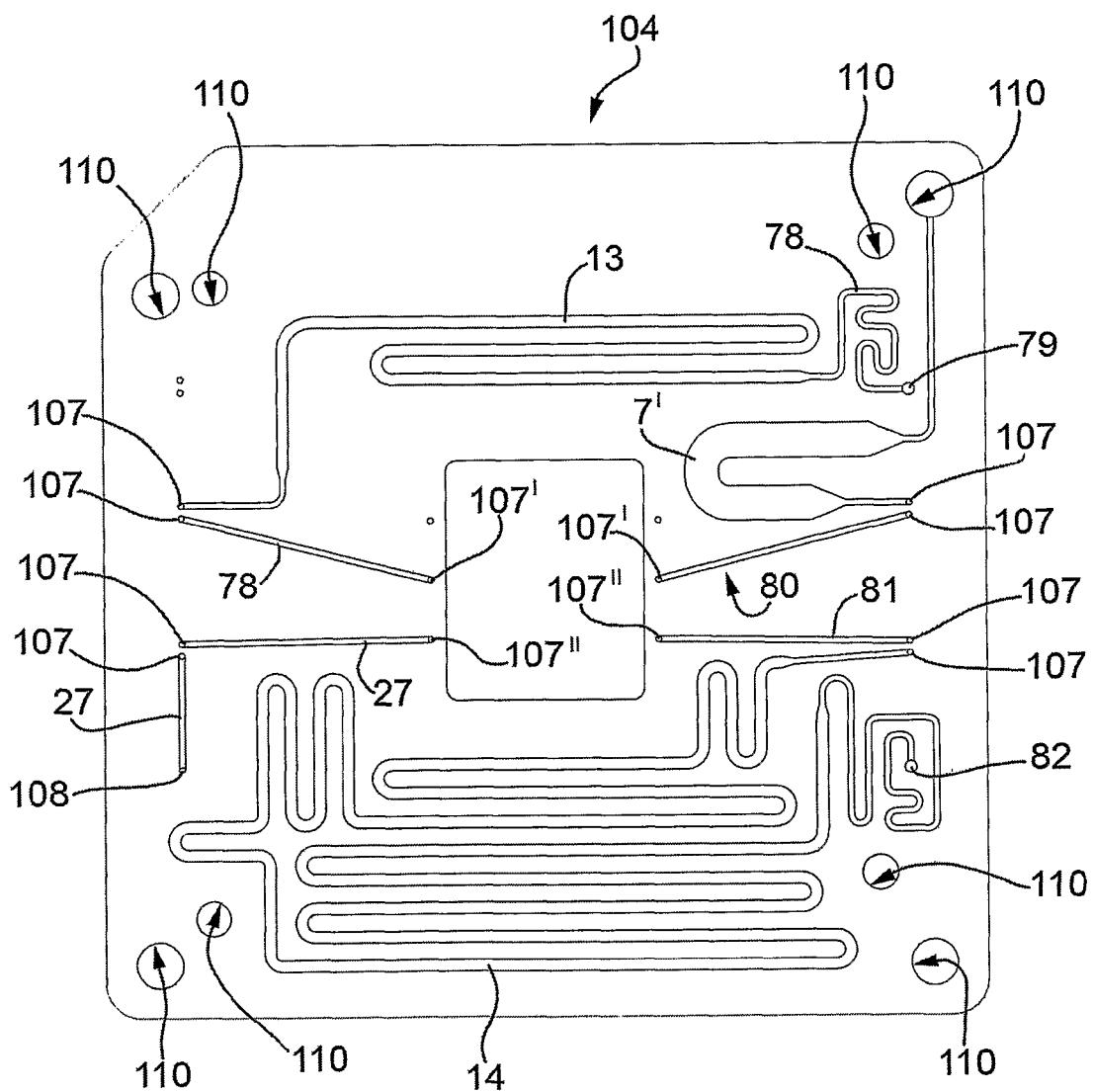
FIG. 5 is a top plan view of a component of the device of FIG. 4.
Figure 6:
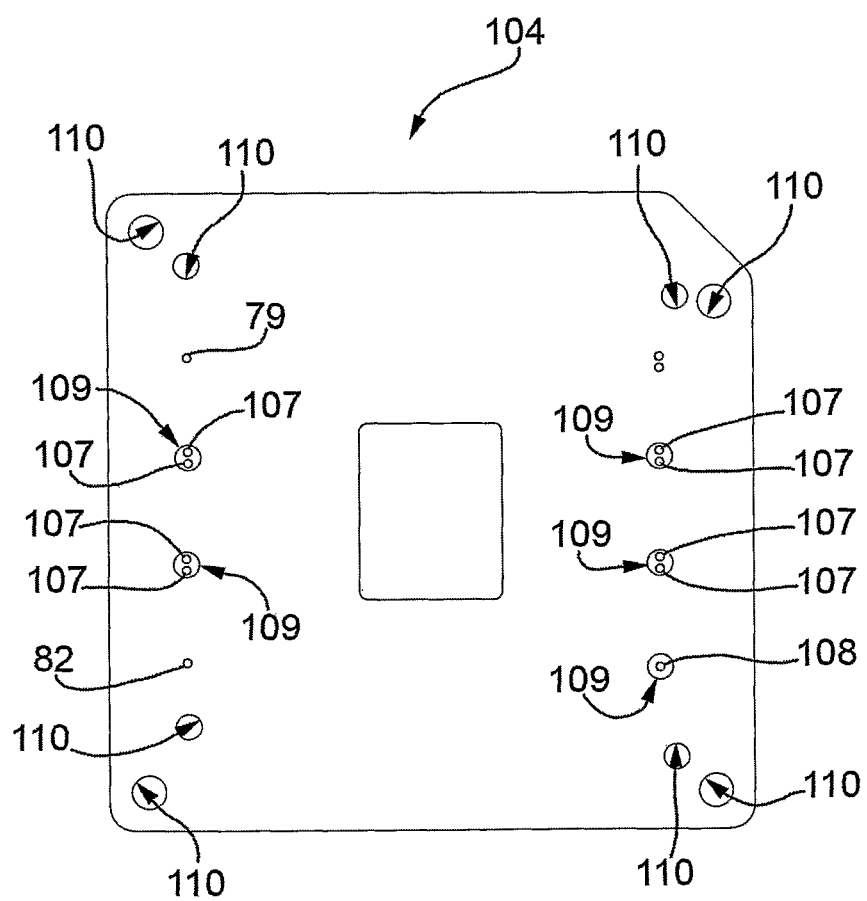
FIG. 6 is a plan view from beneath of the component of FIG. 5.

The plate 104 is illustrated in top plan view in FIG. 5 and in plan view from beneath in FIG. 6. As may be readily noted, on the top surface of the plate 104 (FIG. 5) part of the channels (for example, 78, 80, 81), the reservoirs (for example, 13, 7' and 14) and the holes (for example, 79, 82, 107, 107', 107" and 108) of the device 73 were obtained. The holes 107 were through holes that traverse the entire thickness of the plate 104 and were in pairs component elements of the valve portions 74, 75, 76 and 77 (FIG. 21).

The hole 108 was set at the outlet 8; through the hole 108, in use, the carrier liquid flows away together with the particles C2. The holes 107' and 107" were through holes for connection to the chip 91.

On the bottom surface of the plate 104 around each pair of the holes 107 and around the hole 108 a respective cavity 109 was set. Each cavity had an annular shape and had a diameter of approximately 0.5 mm and a depth of approximately 0.25 mm. The presence of the cavity 109 reduced the area that the closing elements 30 and the seal ring 70 had to press to remain in fluid-tight contact (as regards the closing elements 30 for closing the holes 107).

The plates 104, 105 and 106 had respective through holes 109. During assembly of the device 75, the plates 104, 105 and 106 were arranged in such a way that fixed linear rods extended through the holes 110; in this way, it was possible to align the plates 104, 105 and 106 precisely. The plates 104, 105 and 106 had respective central openings through which, once the device 73 was assembled, it was possible to observe the contents of the chambers 4 and 5.

The plate 106 had openings 111, which, once the device 73 was assembled, enabled the closing elements 30 and the seal rings 66 and 70 to be exposed outwards. Set around each opening 111 was a respective annular cavity, which enabled a better positioning and a better seal of the closing elements 30 and of the seal rings 66 and 70. In practice, said cavities functioned as housings for the closing elements 30 and the seal rings 66 and 70.

Also the aforementioned channels, reservoirs, cavities, openings and holes were obtained by micro-milling.

FIGS. 32 and 33 illustrate a variant of the plate 104. In this case, each cavity 109 has a perimetral channel 119, which is, in particular, substantially circular. For each valve portion 74, 75, 76 and 77, a hole 107 is set in a position corresponding to the channel 119 and a hole 107 is set in the cavity 109 outside the channel 119. This particular configuration enables reduction of the perturbations (in particular, movement—suction—of fluid) during opening of the valve V (FIGS. 14 and 15). Opening of the valve V is relatively gradual and, hence, the negative pressure that is created at the valve V itself during opening is relatively low.

EXAMPLE 5

The closing elements 30, the seal rings 66 and 70, and a connection element 112 were obtained by means of injection-moulding techniques in themselves known. The material used was Elastosil® treated so as to obtain a degree of hardness of 60 shore for the closing elements 30 and 50 shore for the seal rings 66 and 70 and the connection element 112.

The connection element 112 had a central opening 113 and through holes 114, which, once the device 73 had been assembled, connected the chip 91 to the plate 104. In particular, the holes 114 connected the holes 107' with holes 115 of the substrate 92 and the holes 107" with holes 116 of the substrate 92.

EXAMPLE 6

This example describes assembly of the various components described above to obtain the device 73. As has already been mentioned, to align the various components fixed linear rods were used.

The plates 104 and 105 were connected with ethanol bond. A bi-adhesive layer 117 (Duplobond® manufactured by Elcom S.p.A.—thickness: 0.325 mm) was applied on the top face of the plate 106. The bi-adhesive layer 117 adequately shaped (in particular, with a central opening and holes corresponding to the holes 110) was, for example, obtained from a continuous tape, which was cut by means of laser or a dinking machine.

The closing elements 30, the seal rings 66 and 70, and the connection element 111 were mounted on the plate 106. At this point, an organosilane layer was deposited on the bottom surface of the plate 104 and was removed selectively by means of plasma to form a bond only where necessary (a method for selective bonding between the silicone elements and PMMA—polymethyl methacrylate—is described in the patent application No. IT BO2007A000588, the contents of which are completely recalled herein for completeness of description). In particular, the organosilane was removed or was not applied in areas corresponding to the supply holes 79 and 82 and the holes 107, 107' and 107". The closing elements 30, the seal rings 66 and 70, and the connection element 111 were activated by means of plasma. The plates 104 and 106 were brought into contact and pressed against one another.

At this point, a further bi-adhesive layer 118 (Duplobond® manufactured by Lohmann S.p.A.—thickness: 0.325 mm) was applied on the bottom face of the plate 106.

The plate 106 was then pressed against the top face of the PCB 95, the chip 91 having already been mounted on said face.

EXAMPLE 7

This example describes tests conducted for optimizing operation of the system 1.

The sedimentation of the particles C1 and/or C2 represents one of the causes of adhesion of the particles in the reservoir 13 and/or in the duct 78.

Usually, before the sample is introduced into the chamber 4, the sample itself remains in the reservoir 13 for quite a long time (in particular, approximately half an hour). During this period, the particles C1 and C2 deposit on the bottom of the reservoir. To detach the particles from the bottom a strong force is usually necessary. Furthermore, the particles C1 and C2 displace generally more slowly than the liquid part of the sample within the chamber 4. Consequently, the particles C1 and C2 enter the chamber 4 when the chamber 4 has already been at least in part occupied by the liquid part of the sample and manage to distribute only in the central part of the chamber 4 and not uniformly (they do not manage to reach the peripheral corner parts of the chamber 4). It may be noted that there is also the marked risk of not all the particles C1 and C2 reaching the chamber 4.

The non-uniform distribution of the particles C1 and C2 within the chamber 4 renders more problematical separation of the particles C1 from the particles C2 and transfer of the particles C1 themselves into the chamber 5.

Two tests of charging of the chamber 4 were, consequently, conducted keeping the vibration device 17 (comprising a micropump Thinxxs® MDP2205 short-circuited) turned off during the first test and operated (at a frequency of 30 Hz) during the second test.

The samples used were prepared using a K562 cell culture (the concentration of the samples was of approximately 1250 particles/µL) labelled with DAPI.

Figure 22:
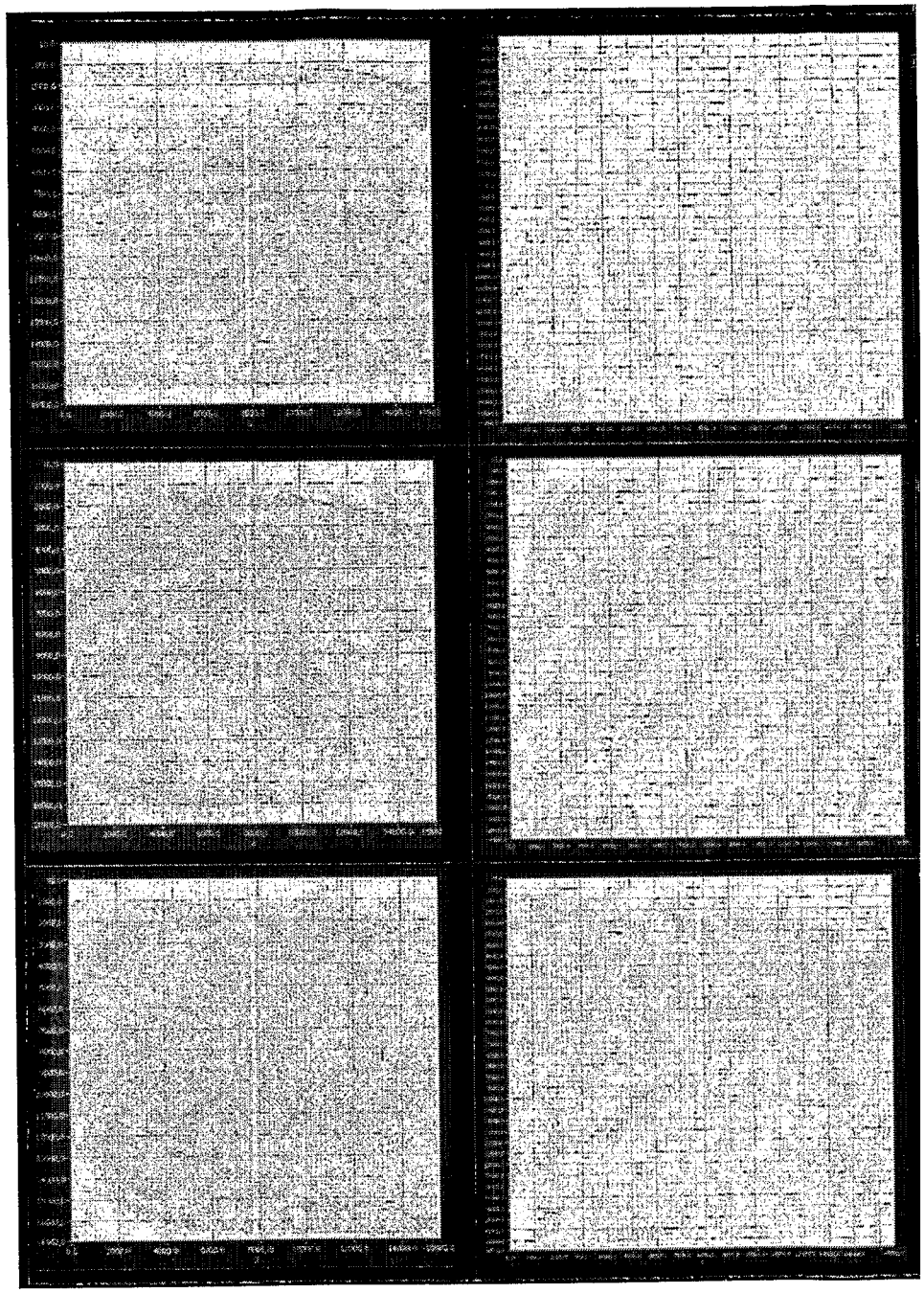
FIG. 22 illustrates photographs of tests conducted using the system of FIG. 1.
Figure 23:
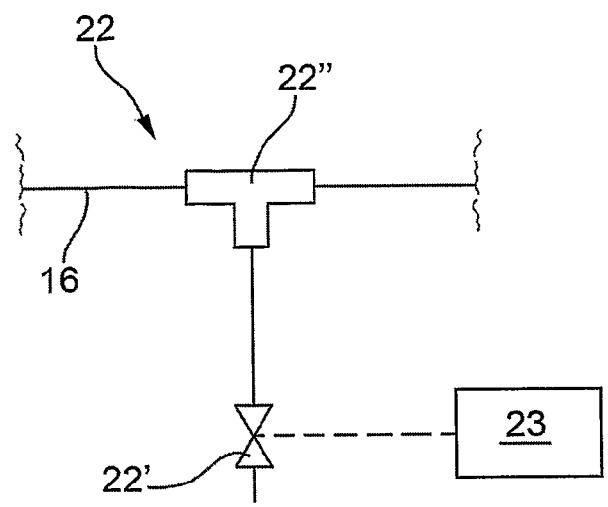
FIG. 23 illustrates at an enlarged scale an embodiment of a detail of FIGS. 1 and 2.

The results of the tests with the vibration device 17 deactivated are illustrated in the photographs of the left-hand column of FIG. 22. The results of the tests with the vibration device 17 activated are illustrated in the photographs of the right-hand column of FIG. 22. The photographs were taken in different optical conditions.

As may be readily noted, when the vibration device 17 was activated, the particles C1 and C2 distributed in a more homogeneous way also within the corners of the chamber 4, thus leading to a significant reduction of the unused volumes.

The invention claimed is:

1. A microfluidic device for isolation of particles (C1) of at least one given type from a sample; the device (73) being designed to be connected to an apparatus (72); the microfluidic device (73) comprising: electrical connectors for connecting the device (73) itself to the apparatus; a first inlet (2), through which, in use, the sample is introduced into the microfluidic device (73); a separation unit (3), which is connected to the first inlet (2), comprises a main chamber (4) and a recovery chamber (5), and is designed to transfer at least part of the particles (C1) of the given type from the main chamber (4) to the recovery chamber (5) in a substantially selective way with respect to further particles (C2) of the sample, wherein the main chamber is separated from the recovery chamber by at least one chamber wall and the main chamber is fluidly coupled and connected to the recovery chamber by a channel; a first outlet (7), connected to the main chamber (4); a second outlet (8), which is connected to the recovery chamber (5), and through which, in use, at least part of the particles (C1) of the given type collected in the recovery chamber (5) exit from the microfluidic device (73); a first valve portion (74) designed to form part of a first valve (9), said first valve portion (74) being set upstream of the main chamber (4) between the first inlet (2) and the main chamber (4); a second valve portion (75), designed to form part of a second valve (10), said second valve portion (75) being set between the main chamber (4) and the first outlet (7); a third valve portion (76), designed to form part of a third valve (11), said third valve portion (76) being connected to the recovery chamber (5); and a fourth valve portion (77), designed to form part of a fourth valve (12), said fourth valve portion (77) being set between the recovery chamber (5) and the second outlet (8); wherein: the recovery chamber (5) is set between the main chamber (4) on one side and the third and fourth valve portions (76, 77) on the other side;

the main chamber (4) is set between the recovery chamber (5) on one side and the first and second valve portions (74, 75) on the other side; at least one of said valve portions (74, 75, 76, 77) comprises a closing element (30), which is designed to pass between a blocking position, in which the closing element (30) is set so as to separate two stretches (31, 32) of a respective channel of the microfluidic device (73), and an opening position, in which the closing element (30) is set in such a way that the two stretches (31, 32) are connected to one another; at least one of the closing elements (30) being operable by a respective actuator external to the microfluidic device (73), the actuator belonging to said apparatus (72).

2. The device according to claim 1, wherein the closing elements (30) are at least partially exposed and set facing the outside of the device; the channel (6), has dimensions smaller than those of the main chamber (4) and of the recovery chamber (5).

3. The device according to claim 1, the separation unit (3) comprises at least part of a dielectrophoresis system.

4. The device according to claim 1, wherein the closing element (30) comprises a substantially elastic material.

5. The device according to claim 1, wherein the closing element (30) has a membrane portion (44), which comprises a substantially elastic material.

6. The device according to claim 1, wherein at least one of said valve portions (74, 75, 76, 77) comprises a diaphragm (33), which is set between two stretches (31, 32) of a channel of the microfluidic device (73); in the blocking position, the closing element (30) is in contact with the diaphragm (33); in the opening position, the closing element (30) is set at a distance from the diaphragm (33).

7. The device according to claim 1, wherein at least one, of said valve portions (74, 75, 76, 77) comprises at least one hole in a channel of the microfluidic device (73).

8. The device according to claim 1, and comprising: a first reservoir (13), which is set between the first inlet (2) and the first valve portion (74) and is designed to collect the sample introduced through the first inlet (2); and a first channel (78), which connects the first reservoir (13) to the main chamber (4) and along which the first valve portion (74) is set.

9. The device according to claim 8, and comprising a first supply hole (79); the first reservoir (13) being set between the first supply hole (79) and the main chamber (4); the first channel (78) connecting the first supply hole (79) to the main chamber (4).

10. The device according to claim 8, and comprising a first seal ring (66) comprising elastic material, said seal ring (66) surrounding outwards the first supply hole (79) and being designed to couple with a respective pressure-supply nozzle (61).

11. The device according to claim 8, and comprising a second channel (80), which is set between the main chamber (4) and the first outlet (7) and has a cross section smaller, by at least 100μm, than the cross section of the first channel (78).

12. The device according to claim 11, wherein the first channel (78) has a cross section of equivalent diameter ranging from 0.9 mm to 50 μm; the second channel (80) has a width of less than 150 μm, a depth of less than 110 μm, and a length greater than 2 mm.

13. The device according to claim 12, wherein the second channel (80) has a width greater than 100 μm, a depth greater than 30 μm, and, a length of less than 6 mm.

14. The device according to claim 1, and comprising: a second reservoir (14), which is designed to contain the carrier liquid; and a third channel (81), which connects the second reservoir (14) to the recovery chamber (5) and along which the third valve portion (76) is set.

15. The device according to claim 14, and comprising a second supply hole (82); the second reservoir (14) being set between the second supply hole (82) and the recovery chamber (5); the third channel (81) connecting the second supply hole (82) to the recovery chamber (5).

16. The device according to claim 14, and comprising a second seal ring (66a), which comprises an elastic material and surrounds outwards the second supply hole (82) and is designed to couple with a further respective pressure-supply nozzle (61 a).

17. The device according to claim 1, and comprising: a third outlet; and a fifth valve portion (29') designed to form a part of a fifth valve (29), said valve portion (29') being set between the recovery chamber (5) and the third outlet; optionally, the third outlet corresponding to the first outlet.

18. The device according to claim 1, and comprising electrical connectors (83) having an electrical circuit, for electrically connecting the microfluidic device (73) itself to an apparatus (72) comprising a control assembly (23) designed to govern the separation unit (3).

19. A microfluidic system for isolation of particles (C1) of at least one given type from a sample; the system (1) comprising:

a first inlet (2), through which, in use, the sample is introduced into the system (1);

a separation unit (3), which is connected to the first inlet (2), comprises a main chamber (5) and a recovery chamber (4), and is designed to transfer at least part of the particles (C1) of the given type from the main chamber (4) to the recovery chamber (5) in a substantially selective way with respect to further particles (C2) of the sample, wherein the main chamber is separated from the recovery chamber by at least one chamber wall and the main chamber is fluidly coupled and connected to the recovery chamber by a channel fluidly coupled to the recovery chamber by a channel;

a first outlet (7), connected to the main chamber (4); and a second outlet (8), which is connected to the recovery chamber (5), and, through which, in use, at least part of the particles (C1) of the given type collected in the recovery chamber (5) exit from the system (1):

a first valve (9), set upstream of the main chamber (4), namely between the first inlet (2) and the main chamber (4);

a second valve (10), set between the main chamber (4) and the first outlet (7);

a third valve (11), which is connected to the recovery chamber (5) and is set between the recovery chamber (5) and a source of a carrier liquid; and a fourth valve (12), set between the recovery chamber (5) and the second outlet (8);

wherein: the recovery chamber (5) is set between the main chamber (4) on one side and the third and fourth valves (11, 12) on the other side; and the main chamber (4) is set between the recovery chamber (5) on one side and the first and second valves (9, 10) on the other side.

20. The system according to claim 19, and comprising a dielectrophoresis system; the separation unit (3) comprises at least part of the dielectrophoresis system; the first and second valves (9, 10) being designed to regulate inflow of the sample into the main chamber (4); the third and fourth valves (11, 12) being designed to regulate inflow of carrier liquid to the recovery chamber (5) and outflow of the carrier liquid together with the particles (C1) of the given type from the recovery chamber (5) through the second outlet (8); the first outlet (7) is connected to the main chamber (4) to enable the sample to enter freely within the main chamber (4), thus functioning as a breather.

21. A microfluidic system for isolation of particles (C1) of at least one given type from a sample, comprising two separable portions: a substantially fixed apparatus (72) and a device (73) as defined in claim 1.

22. The system according to claim 19, wherein the channel dimensions smaller than those of the main chamber (4) and of the recovery chamber (5).

23. The system according to claim 19, and comprising a first reservoir (13), which is set between the first inlet (2) and the first valve (9) and is designed to collect the sample introduced through the first inlet (2).

24. The system according to claim 19, wherein the first valve (9) is set between the first inlet (2) and the main chamber (4), between the first reservoir (13) and the main chamber (4), and is designed to connect or isolate the first inlet (2) and the main chamber (4) with respect to one another.

25. The system according to claim 19, and comprising a second reservoir (14) for containing the carrier liquid, which is designed to fill the recovery chamber (5).

26. The system according to claim 25, and comprising a second inlet (24); the second reservoir (14) being set between the second inlet (24) and the third valve (11) and being designed to collect the carrier liquid introduced through the second inlet (24).

27. The system according to claim 25, wherein the third valve (11) is set between the second reservoir (14) and the recovery chamber (5) and is designed to connect or isolate the second reservoir (14) and the recovery chamber (5) with respect to one another.

28. The system according to claim 19, and comprising: a first reservoir (13), which is set between the first inlet (2) and the first valve (9) and is designed to collect the sample introduced through the first inlet (2); and a second reservoir (14) for containing the carrier liquid, which is designed to fill the recovery chamber (5); the system (1) comprising a first pressure source (15) for imposing a pressure difference between the first reservoir (13) and the main chamber (4), and a second pressure source (25) for imposing a pressure difference between the second reservoir (14) and the recovery chamber (5).

29. The system according to claim 28, wherein the first reservoir (13) is set between the first pressure source (15) and the first valve (9); the second reservoir (14) being set between the second pressure source (25) and the third valve (11).

30. The system according to claim 28, wherein the first pressure source (15) is set between the first reservoir (13) and the main chamber (4) and comprises the first valve (9) and a fifth valve, said first and fifth valves (9) being set one after the other and being, in use, actuated in succession so as to enable entry of the sample into the main chamber (4).

31. The system according to claim 28, and comprising: a first duct (16), which connects the first pressure source (15) to the main chamber (4) and set along which are the first reservoir (13) and the first valve (9); and a second duct (26), which connects the second pressure source (25) to the recovery chamber (5) and set along which are the second reservoir (14) and the third valve (11).

32. The system according to claim 28, and comprising a vibration device (17), which is designed to impose a vibration on the sample at least in an area from the first inlet (2) to the main chamber (4) and is set between the first pressure source (15) and the first reservoir (13).

33. The system according to claim 29, and comprising: a first reservoir (13), which is set between the first inlet (2) and the first valve (9) and is designed to collect the sample introduced through the first inlet (2); a first duct (16) for connecting the first reservoir (13) to the main chamber (4); and a third duct (20), which is set between the main chamber (4) and the first outlet (7) and has a cross section smaller, by at least 100 µm, than the cross section of the first duct (16).

34. The system according to claim 33, wherein the first duct (16) has a cross section of equivalent diameter measuring from 2 mm to 50 µm; the third duct (20) has a width of less than 150 µm, a depth of less than 110 µm, and a length greater than 2 mm.

35. The system according to claim 34, wherein the third duct (20) has a width greater than 100 µm, a depth greater than 30 µm, and, a length of less than 6 mm.

36. The system according to claim 33, and comprising: a sensor (21) for detecting directly or indirectly when the sample starts to enter the third duct (20); a blocking device (22; 9) for blocking inflow of the sample towards the main chamber (4); and a control assembly (23), connected to the sensor (21) and to the blocking device (22; 9) for actuating the blocking device (22; 9) as a function of what has been detected by the sensor (21).

37. The system according to claim 36, and comprising a first pressure source (15) for imposing a pressure from the first reservoir (13) towards the main chamber (4); the first reservoir (13) being set between the first pressure source (15) and the first valve (9); the blocking device (22) comprising a relief valve (22') set between the first pressure source (15) and the first reservoir (13), said relief valve (22') being actuated by the control assembly (23) and being designed, when actuated, to set in communication the pressure source (15) with the outside world so as to bring substantially to zero the pressure from the first reservoir (13) towards the main chamber (4).

38. The system according to claim 19, and comprising: a third outlet; and a sixth valve (29), which is set between the recovery chamber (5) and the third outlet; optionally the third outlet coinciding with the first outlet (7).

39. The system according to claim 19, comprising a vibration device (17), which is designed to cause variation in an oscillating way of the pressure at least in an area from the first inlet (2) to the main chamber (4).

40. The system according to claim 39, wherein the vibration device (17) comprises an oscillating diaphragm.

41. The system according to claim 19, wherein at least one of the valves (9; 10; 11; 12) comprises: a diaphragm (33), which is set between two stretches (31, 32) of a duct; a closing element (30), which comprises a substantially elastic material and is designed to pass between a blocking position, in which the closing element (30) is in contact with the diaphragm (33) so as to separate the two stretches (31, 32), and an opening position, in which the closing element (30) is set at a distance from the diaphragm (33) and the two stretches are connected to one another; a first mechanical-pressure element (34) for pushing the closing element (30) towards the diaphragm (33) so as to keep the closing element (30) in the blocking position; and a fluid-dynamic actuator (35) for bringing the closing element from the blocking position to the opening position.

42. The system according to claim 41, wherein the closing element (30) has a membrane portion (44), which comprises a substantially elastic material.

43. The system according to claim 41, wherein the first mechanical-pressure element (34) comprises a spring.

44. The system according to claim 41, wherein the fluid-dynamic actuator (35) comprises a suction unit (41) comprising a pump (43).

45. The system according to claim 41, and comprising a hollow element (37) for housing the first mechanical-pressure element (34) and for connecting the suction unit (41) with the closing element (30); the hollow element (37) having an open end set in contact with the closing element (30); the system comprising a second mechanical-pressure element (46) for pushing the hollow element (37) towards the closing element (30).

46. The system according to claim 19, and comprising a cooling assembly (50), which is designed to cool at least part of the separation unit (3).

47. The system according to claim 46, wherein the cooling assembly (50) comprises a cooling plate (51) having: an active surface (52) designed to absorb heat from the separation unit (3); and a discharging surface (53) for yielding heat; the active surface (52) having dimensions smaller than the discharging surface (53).

48. The system according to claim 46, and comprising a third mechanical-pressure element (60) for pushing the cooling assembly (50) towards the separation unit (3).

49. The system according to claim 19, comprising a control assembly (23) connected to said valves (9, 10, 11, 12) for opening and closing the valves (9, 10, 11, 12) themselves.

50. The system according to claim 49, and comprising a collection unit for collecting the carrier liquid containing at least part of the particles (C1) of the given type coming out from the second outlet.

51. The system according to claim 50, and comprising a detector for detecting when at least one drop of said carrier liquid enters the collection unit; the control assembly (23) being connected to the detector and being designed to close the third valve (11) and/or the fourth valve (12) when the drop is detected.

52. The system according to claim 19, comprising a second vibration device (17a), which is designed to cause variation in an oscillating way of the pressure at least in one area of the recovery chamber (5).

53. A method for isolation of particles (C1) of at least one given type from a sample by means of a microfluidic system (1); the method comprising:
a step of introduction of the sample into the system (1) through a first inlet (2) of the system (1) itself;
a separation step, during which at least part of the particles (C1) of the given type are transferred from a main chamber (4) to a recovery chamber (5) of a separation unit (3) of the system (1), through a channel fluidly coupling the main chamber and the recovery chamber, in a substantially selective way with respect to further particles (C2) of the sample; a first outlet (7) and a second outlet (8) being connected to the main chamber (4) and to the recovery chamber (5), respectively, wherein the main chamber is separated from the recovery chamber by at least one chamber wall and the channel connects the main chamber and the recovery chamber;
a first supply step, which at least partially precedes the separation step and during which at least part of the sample is fed into the main chamber (4);
a second supply step, which at least partially precedes the separation step and during which carrier liquid is fed into the recovery chamber (5); and
a recovery step, which is at least partially subsequent to the separation step and during which the carrier liquid together with at least part of the particles (C1) of the given type flow out of the recovery chamber (5) through the second outlet (8);
the method being characterized in that the system (1) comprises: a first valve (9), which is set upstream of the main chamber (4); a second valve (10), set downstream of the main chamber (4); a third valve (11), set upstream of the recovery chamber (5); and a fourth valve (12), set downstream of the recovery chamber (5);
during the separation step the first, second, third, and fourth valves (9, 10, 11, 12) are closed.

54. The method according to claim 53, wherein during the first supply step the first valve and the second valve (9, 10) are open; said second valve (10) being set between the main chamber (4) and the outlet (7);
during the second supply step the third and fourth valves (11, 12) are open; said fourth valve (12) being set between the recovery chamber (5) and the outlet (8); and
during the recovery step the third and fourth valves (11, 12) are open;
during the separation step the first, second, third, and fourth valves (9, 10, 11, 12) are closed so as to isolate the main chamber (4) and the recovery chamber (5) with respect to the outside.

55. The method according to claim 53, wherein the system is defined in accordance with claim 19.

56. The method according to one to claim 53, and comprising a discharging step, which is at least partially subsequent to the separation step and at least partially prior to the recovery step and during which at least part of the further particles (C2) of the sample are made to flow out of the main chamber (4) through the first outlet (7).

57. The method according to claim 56, wherein, during the discharging step, the second and third valves (10, 11) are open so as to feed the carrier liquid to the main chamber (4).

58. The method according to claim 56, wherein the particles (C1) of the given type are arranged within the recovery chamber (5) in such a way that, during the discharging step, they remain at least in part inside the recovery chamber (5) itself.

59. The method according to claim 53, wherein a first pressure is imposed for feeding the sample to the main chamber (4).

60. The method according to claim 53, wherein, during the introduction step at least part of the sample is introduced into a first reservoir (13) of the system (1).

61. The method according to claim 60, wherein a first pressure is imposed for feeding the sample into the main chamber (4); the first pressure carrying the sample from the first reservoir towards the main chamber (4).

62. The method according to claim 59, wherein the first pressure is exerted at least before and during the first supply step.

63. The method according to claim 53, wherein, during the first supply step, the sample passes through the first valve (9).

64. The method according to claim 53, wherein a second pressure is imposed for feeding the carrier liquid into the recovery chamber (5).

65. The method according to claim 64, wherein the second pressure pushes the carrier liquid from a second reservoir (14) of the system (1) towards the recovery chamber (5).

66. The method according to claim 65, wherein the second pressure is exerted at least before and during the second supply step.

67. The method according to claim 53, wherein, during the second supply step, the carrier liquid passes through the third valve (11).

68. The method according to claim 53, wherein, during the first supply step, the sample is subjected to vibration.

69. The method according to claim 53, wherein the system (1) comprises: a first duct (16) for connecting the first inlet (2) to the main chamber (4); and a second duct (20), which is set between the main chamber (4) and the first outlet (7) and has a cross section smaller, by at least 100 μm, than the cross section of the first duct (16); during the first supply step, the pressure of the sample being detected; feeding of the sample being interrupted as a function of the detected pressure when a pressure greater than a given value is detected.

70. The method according to claim 53, wherein the separation step occurs by dielectrophoresis.

71. The method according to claim 53, wherein, at least during the separation step, the separation unit (3) is cooled.

72. The method according to claim 53, wherein the system (1) comprises: a third outlet; and a fifth valve (29), which is set between the recovery chamber and the third outlet; during the second filling step, the third and fourth valves (11, 12) being open so as to fill a first area (5') of the recovery chamber (5) that connects the third and fourth valves (11, 12), the third and fifth valves (11, 29) being open for filling a second area (5") of the recovery chamber (5) that connects the third and fifth valves (11, 29); optionally the third outlet coinciding with the first outlet (7).

73. The method according to claim 72, wherein, during the separation step, at least part of the particles (C1) of the given type and at least part of particles (C3) of at least one second given type are transferred into the recovery chamber (5); the recovery step comprising a first recovery substep, during which at least part of the particles (C1) of the given type is brought in a substantially selective way into the first area (5') and, subsequently, at least part of the particles (C1) of the given type is made to flow out of the first area (5') through the second outlet (8), feeding further carrier liquid into the recovery chamber (5).

74. The method according to claim 73, and comprising a second recovery substep, during which at least part of the particles (C3) of the second given type is brought into the first area (5') and, subsequently, is made to flow out of the recovery chamber (5) through the second outlet (8). feeding further carrier liquid into the recovery chamber (5).

75. The method according to claim 72, wherein, during the recovery step, the fifth valve (29) is closed.

76. The method according to claim 53, wherein, during the recovery step the contents of the recovery chamber (5) are subjected to vibration.

77. The method according to claim 53, wherein, during the recovery step, the first drop of carrier liquid that exits from the second outlet (8) together with at least part of the particles (C1) of the given type is detected; when the first drop is detected, outflow from the recovery chamber (5) is blocked.

78. The method according to claim 53, wherein, prior to the step of introduction of the sample, carbon dioxide is conveyed into the system (1).

79. The device according to claim 1, wherein the channel has dimensions smaller than those of the main chamber (4) and the of the recovery chamber (5).

* * * * *